US 11,976,109 B2

(12) United States Patent
Sullivan et al.

(10) Patent No.: US 11,976,109 B2
(45) Date of Patent: May 7, 2024

(54) NEUTRALIZING ANTIBODIES TO EBOLA VIRUS GLYCOPROTEIN AND THEIR USE

(71) Applicant: The U.S.A., as represented by the Secretary, Department of Health and Human Services, Bethesda, MD (US)

(72) Inventors: Nancy Sullivan, Kensington, MD (US); Kendra Leigh, Frankfurt am Main (DE); John Misasi, Kensington, MD (US); Alberto Cagigi, Stockholm (SE)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 892 days.

(21) Appl. No.: 16/959,644

(22) PCT Filed: Dec. 31, 2018

(86) PCT No.: PCT/US2018/068198
§ 371 (c)(1),
(2) Date: Jul. 1, 2020

(87) PCT Pub. No.: WO2019/136029
PCT Pub. Date: Jul. 11, 2019

(65) Prior Publication Data
US 2021/0079067 A1   Mar. 18, 2021

Related U.S. Application Data

(60) Provisional application No. 62/612,982, filed on Jan. 2, 2018.

(51) Int. Cl.
| *C07K 16/10* | (2006.01) |
| *A61K 39/00* | (2006.01) |
| *A61K 48/00* | (2006.01) |
| *A61P 31/14* | (2006.01) |
| *G01N 33/569* | (2006.01) |

(52) U.S. Cl.
CPC .............. *C07K 16/10* (2013.01); *A61P 31/14* (2018.01); *G01N 33/56983* (2013.01); *A61K 2039/505* (2013.01); *A61K 2039/507* (2013.01); *A61K 48/005* (2013.01); *C07K 2317/33* (2013.01); *C07K 2317/565* (2013.01); *C07K 2317/567* (2013.01); *C07K 2317/72* (2013.01); *C07K 2317/76* (2013.01); *C07K 2317/92* (2013.01); *C07K 2317/94* (2013.01); *G01N 2333/08* (2013.01); *G01N 2400/02* (2013.01); *G01N 2469/10* (2013.01)

(58) Field of Classification Search
None
See application file for complete search history.

(56) References Cited

FOREIGN PATENT DOCUMENTS

| CA | 2 995 922 | 2/2017 |
| WO | WO 2016/075546 | 5/2016 |
| WO | WO 2016/077789 | 5/2016 |
| WO | WO 2016/123019 | 8/2016 |
| WO | WO 2016/128349 | 8/2016 |
| WO | WO 2016/154572 | 9/2016 |
| WO | WO 2016/196343 | 12/2016 |

OTHER PUBLICATIONS

Corti et al., "Protective monotherapy against lethal Ebola virus infection by a potently neutralizing antibody," *Science* 351(6279): 1339-1342, 2016.

Misasi et al., "Structural and Molecular Basis for Ebola Virus Neutralization by Protective Human Antibodies," *Science* 351(6279): 1343-1346, 2016.

The Prevail II Writing Group, for the Multi-National Prevail IiIStudy Team, A Randomized, Controlled Trial of ZMapp for Ebola Virus Infection, *N Engl J Med* 375: 1448-1456, 2016.

*Primary Examiner* — Karen A. Canella
(74) *Attorney, Agent, or Firm* — Klarquist Sparkman, LLP

(57) ABSTRACT

Antibodies and antigen binding fragments that specifically bind to ebolavirus glycoprotein and neutralize ebolavirus infection are disclosed. Nucleic acids encoding these antibodies, vectors, and host cells are also provided. The disclosed antibodies, antigen binding fragments, nucleic acids and vectors can be used, for example, to inhibit an ebolavirus infection in a subject.

36 Claims, 15 Drawing Sheets
Specification includes a Sequence Listing.

FIG. 6

|  | | Analyte | | | | |
|---|---|---|---|---|---|---|
|  | | VRC01 | mAb114 | KZ52 | mAb100 | S1-4-A09 |
| Competitor | VRC01 | NB | -0.1% | 8.1% | -2.9% | 6.3% |
| | mAb114 | NB | 95.7% | 16.4% | -8.2% | -0.7% |
| | KZ52 | NB | 8.8% | 96.4% | 80.7% | 83.0% |
| | mAb100 | NB | 13.5% | 98.3% | 100.2% | 99.9% |
| | S1-4-A09 | NB | 12.3% | 98.6% | 101.3% | 100.8% |

% inhibition of binding

FIG. 9

EBOV Challenge Day 0

Study End Day 28 mAb Administration: Day 1, Day 2, Day 3

| # of Animals | Antibody Administered | Dosage | Administrations |
|---|---|---|---|
| 3 | S1-4-A09 | 50 mg/kg/dose | 3 |
| 1 | none | N/A | none |

1 — A09
2 — No Treatment

| # of Animals | Antibody Administered | mAb114:S1-4A09 | Dosage | Administrations |
|---|---|---|---|---|
| 3 | mAb114 & S1-4-A09 | 50%:50% | 50 mg/kg/dose | 3 |
| 3 | mAb114 & S1-4-A09 | 92%:8% | 50 mg/kg/dose | 3 |
| 1 | none | N/A | N/A | none |

NEUTRALIZING ANTIBODIES TO EBOLA VIRUS GLYCOPROTEIN AND THEIR USE

CROSS REFERENCE TO RELATED APPLICATIONS

This application is the U.S. National Stage of Internal Application No. PCT/US2018/068198, filed Dec. 31, 2018, which was published in English under PCT Article 21(2), which claims the benefit of U.S. Provisional Application No. 62/612,982, filed Jan. 2, 2018, which is herein incorporated by reference in its entirety.

FIELD

This relates to monoclonal antibodies and antigen binding fragments that specifically bind to ebolavirus glycoprotein (GP) and their use, for example, in methods of inhibiting ebolavirus infection or ebolavirus disease (EVD) in a subject.

BACKGROUND

EVD is a disease in humans, chimpanzees, and monkeys, caused by infection with an ebolavirus. The prototypic member of this genus, *Zaire ebolavirus*, was first identified in the Democratic Republic of Congo (formerly known as the Republic of Zaire) in 1976. Ebolaviruses are members of the Filoviridae family of RNA viruses and cause a severe hemorrhagic fever with a high mortality rate. For example, infection with *Zaire ebolavirus* is associated with a mortality rate of up to 90% in humans.

While prior outbreaks of EVD have been localized to regions of Africa, the potential threat of dissemination to other countries has been exacerbated by the frequency of international travel. The 2014 outbreak in West Africa was first recognized in March 2014, and as of Apr. 13, 2016, the number of cases far exceeded the largest prior EVD outbreak with a combined total (suspected, probable, and laboratory-confirmed) 28616 cases and 11310 deaths (case fatality rate=39.5%). The largest previous outbreak of an ebolavirus occurred in Uganda in 2000-2001 with 425 cases and 224 deaths (case-fatality rate=53%).

During infection, proteases of the host cell cleave a precursor of GP, termed $GP_0$, into $GP_1$ and $GP_2$. $GP_2$ is an integral membrane protein, while $GP_1$ protrudes from the mature virus. Three copies of the $GP-GP_2$ heterodimer make up the ebolavirus envelope spike, which is a target for neutralizing antibodies.

Although certain neutralizing antibodies that bind to ebolavirus GP have been identified, there is a need to develop additional neutralizing antibodies with varying ebolavirus GP recognition profiles and increased neutralization potency. The challenges of a large outbreak and the failure of traditional quarantine and contact tracing measures to control an outbreak of this scale highlights the urgency for therapies.

SUMMARY

Isolated antibodies and antigen binding fragments that specifically bind to ebolavirus GP and neutralize ebolavirus are provided herein.

In some embodiments, the antibody or antigen binding fragment comprises a heavy chain variable region ($V_H$) comprising a heavy chain complementarity determining region (HCDR)1, a HCDR2, and a HCDR3 of the $V_H$ set forth as SEQ ID NO: 1 (S1-4-A09 $V_H$) and a light chain variable region ($V_L$) comprising a light chain complementarity determining region (LCDR)1, a LCDR2, and a LCDR3 of the $V_L$ set forth as SEQ ID NO: 2 (S1-4-A09 $V_L$). In some embodiments, the HCDR1, the HCDR2, the HCDR3, the LCDR1, the LCDR2, and the LCDR3 comprise the amino acids sequences set forth as SEQ ID NOs: 7-12, respectively. In some embodiments, the antibody or antigen binding fragment comprises a $V_H$ and a $V_L$ comprising the amino acid sequences set forth as SEQ ID NOs: 1 and 2, respectively. In some embodiments, the antibody or antigen binding fragment comprises a $V_H$ and a $V_L$ comprising the amino acid sequences set forth as SEQ ID NOs: 3 and 2, respectively.

In some embodiments, the $V_H$ of the antibody does not contain an N-linked glycan sequon beginning at any of Kabat residues 58-60. For example, the $V_H$ of the antibody comprises one or more amino acid substitutions to remove an N-linked glycan sequon beginning at any of Kabat residues 58-60. In some embodiments, the $V_H$ of the antibody does not contain an N-linked glycan sequon beginning at Kabat residue 60. For example, the $V_H$ of the antibody comprises an A61P substitution (Kabat numbering) to remove an N-linked glycan sequon beginning at Kabat position 60.

Also disclosed are compositions including the antibodies and antigen binding fragments, nucleic acids encoding the antibodies and antigen binding fragments, expression vectors comprising the nucleic acids, and isolated host cells that comprise the nucleic acids. In several embodiments, the nucleic acid molecule encoding a disclosed antibody or antigen binding fragment can be a cDNA molecule that encodes the antibody or antigen binding fragment. In additional embodiments, the nucleic acid molecule can be a bicistronic expression construct encoding the $V_H$ and $V_L$ of the antibody or antigen binding fragment.

Surprisingly, the disclosed antibodies and antigen binding fragments potently neutralize ebolavirus and inhibit ebolavirus infection in accepted in vitro and in vivo models. Accordingly, a method is disclosed for inhibiting (including preventing) ebolavirus infection in a subject. The method comprises administering an effective amount (that is, an amount effective to inhibit ebolavirus infection in a subject) of one or more of the disclosed antibodies, antigen binding fragments, nucleic acid molecules, vectors, or compositions, to the subject, such as a subject at risk of or having an ebolavirus infection.

The antibodies, antigen binding fragments, nucleic acid molecules, vectors, and compositions disclosed herein can be used for a variety of additional purposes, such as for diagnosing ebolavirus infection in a subject, or detecting ebolavirus in a sample.

The foregoing and other features and advantages of this disclosure will become more apparent from the following detailed description of several embodiments, which proceeds with reference to the accompanying figures.

BRIEF DESCRIPTION OF THE FIGURES

FIG. 6. S1-4-A09 competition group as determined by biolayer interferometry. The order of addition to the biosensors was mucin-domain-deleted GP (antigen), competitor mAb, analyte mAb. VRC01 is an isotype control mAb that does not bind GP. mAb114 binds the GP trimer at its membrane distal apex. KZ52 and mAb100 are two survivor-isolated mAbs that bind at the base (membrane-proximal) of the GP trimer.

FIG. 9. In vivo neutralization of Zaire ebolavirus (EBOV) infection by S1-4-A09 IgG. Top, schematic of Zaire ebolavirus challenge and S1-4-A09 dosing timeline for in vivo efficacy studies. Middle, dosage of S1-4-A09 administered intravenously to macaques for in vivo efficacy studies. Bottom, Kaplan-Meier curves for survival in the in vivo efficacy study for S1-4-A09 alone. Animals in the A09 group received three doses of S1-4-A09 at 50 mg/kg/dose. The "No Treatment" group did not receive any antibody.

SEQUENCE LISTING

Figure 1:
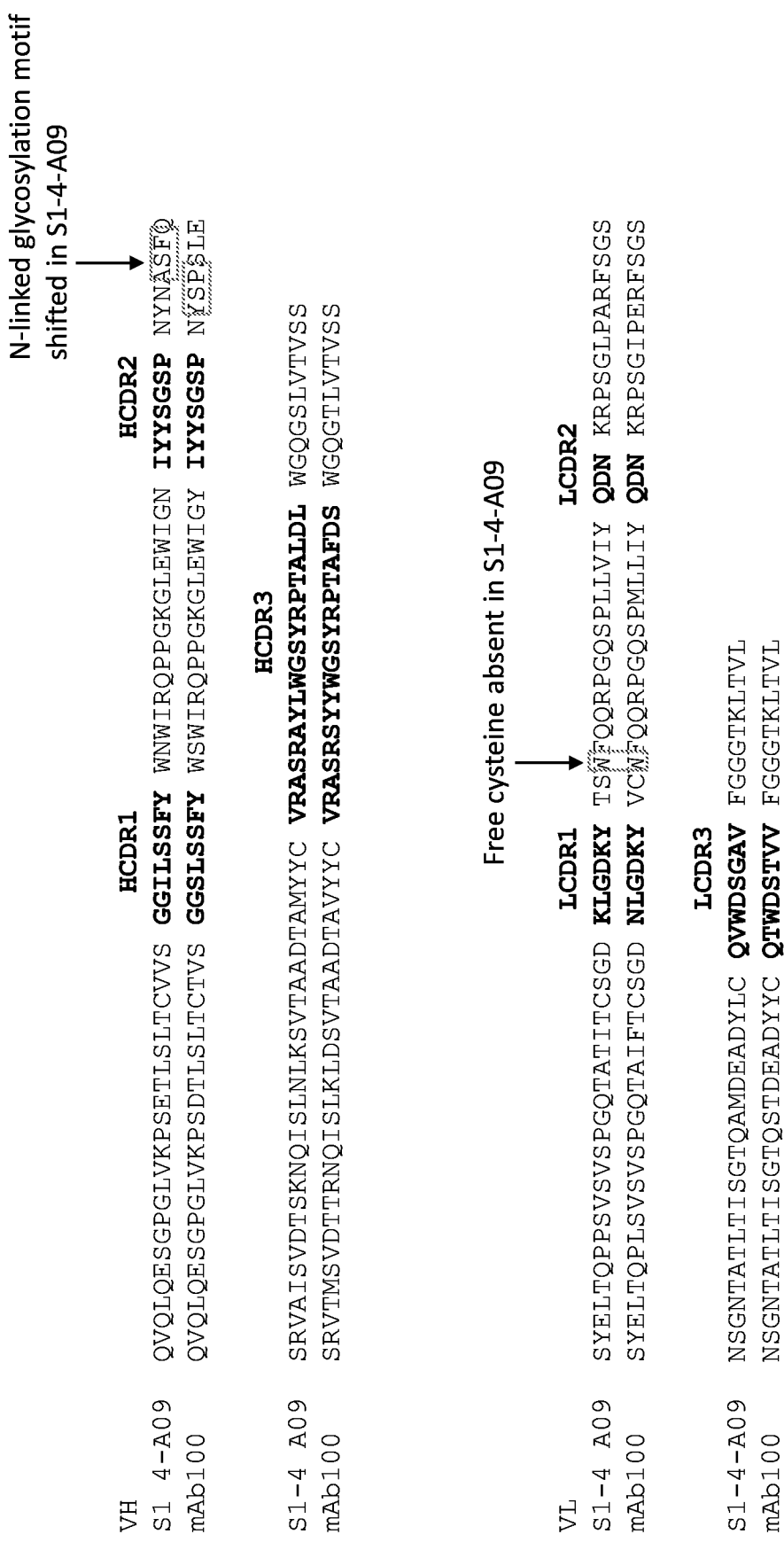
FIG. 1. Sequences of S1-4-A09 $V_H$ (SEQ ID NO: 1) and $V_L$ (SEQ ID NO: 2) showing CDRs (IMGT) and comparison with mAb100 $V_H$ (SEQ ID NO: 23) and $V_L$ (SEQ ID NO: 24) sequences.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jun. 16, 2020, 58.1 KB, which is incorporated by reference herein. In the accompanying sequence listing:

SEQ ID NO: 1 is the amino acid sequence of the S1-4-A09 V$_H$.
QVQLQESGPGLVKPSETLSLTCVVSggilssfyWNWIRQPPGKGLEWIGNiyysgspNYNASFQSRVAISVDTSKNQIS
LNLKSVTAADTAMYYCvrasraylwgsyrptaldlWGQGSLVTVSS SEQ ID NO: 2 is the amino acid sequence of the S1-4-A09 V$_L$.
SYELTQPPSVSVSPGQTATITCSGDklgdkyTSWFQQRPGQSPLLVIYqdnKRPSGLPARFSGSNSGNTATLTISGTQA
MDEADYLCqvwdsgavFGGGTKLTVL SEQ ID NO: 3 is the amino acid sequence of the S1-4-A09 A61P V$_H$.
QVQLQESGPGLVKPSETLSLTCVVSggilssfyWNWIRQPPGKGLEWIGNiyysgspNYNPSFQSRVAISVDTSKNQIS
LNLKSVTAADTAMYYCvrasraylwgsyrptaldlWGQGSLVTVSS SEQ ID NO: 4 is the amino acid sequence of an IgG1 heavy chain including the
S1-4-A09 V$_H$.
QVQLQESGPGLVKPSETLSLTCVVSggilssfyWNWIRQPPGKGLEWIGNiyysgspNYNASFQSRVAISVDTSKNQIS
LNLKSVTAADTAMYYCvrasraylwgsyrptaldlWGQGSLVTVSSASTKGPSVFPLAPSSKSTSGGTAALGCLVKDYF
PEPVTVSWNSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK SEQ ID NO: 5 is the amino acid sequence of an IgG1 light chain including the
S1-4-A09 V$_L$.
SYELTQPPSVSVSPGQTATITCSGDklgdkyTSWFQQRPGQSPLLVIYqdnKRPSGLPARFSGSNSGNTATLTISGTQA
MDEADYLCqvwdsgavFGGGTKLTVLGQPKAAPSVTLFPPSSEELQANKATLVCLISDFYPGAVTVAWKADSSPVKAGV
ETTTPSKQSNNKYAASSYLSLTPEQWKSHRSYSCQVTHEGSTVEKTVAPTECS SEQ ID NO: 6 is the amino acid sequence of an IgG1 heavy chain including the
S1-4-A09 A61P V$_H$.
QVQLQESGPGLVKPSETLSLTCVVSggilssfyWNWIRQPPGKGLEWIGNiyysgspNYNPSFQSRVAISVDTSKNQIS
LNLKSVTAADTAMYYCvrasraylwgsyrptaldlWGQGSLVTVSSASTKGPSVFPLAPSSKSTSGGTAALGCLVKDYF
PESPVTVSWKSGALTSGVHTFPAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVKGFYPSDIAVEWESNGQP
ENNYKTTPPVLDSDGSFFLYSKLTVDKSRWQQGNVFSCSVMHEALHNHYTQKSLSLSPGK SEQ ID NOs: 7-12 are the amino acid sequences of antibody CDRs.

SEQ ID NO: 13 is an exemplary nucleic acid sequence encoding the S1-4-A09 V$_H$.
atgggatggtcatgtatcatcctttttctagtagcaactgcaaccggtgtacattctcaggtgcagctgcaggagtcgg
gaccaggactggtgaagccttcggagaccctgtccctcacctgcgttgtctctggtggcatcctcagtagtttttactg
gaactggatccggcagccccaggaaagggactggagtggattggaaacatctattacagtgggagccccaactataat
gcctccttccagagtcgagtcgccatttcggtggacacgtccaagaaccagatctccctgaacctcaagtctgtgaccg
ctgcggacacggccatgtattactgtgtgagagcctcccgcgcttacctttggggagttatcgtccaacggctcttga
cctctggggccagggatccctggtcaccgtctcctca SEQ ID NO: 14 is an exemplary nucleic acid sequence encoding the S1-4-A09 V$_L$.
atgggatggtcatgtatcatcctttttctagtagcaactgcaaccggtgtccatgcttcctatgggtgactcagccac
cctcagtgtccgtgtccccaggacagacagccaccatcacgtgctctggagataaattgggtgataaatatacttcctg
gttccagcagaggccaggccagtcccctctactggtcatctatcaggataataagcggccctcagggctccctgcgcga
ttttctggctccaactctgggaacacagccactctgaccatcagcggcacccaggctatggatgaggctgactatttgt
gtcaggtgtgggacagcggtgcggtgttcggcggagggaccaagctgaccgtccta SEQ ID NO: 15 is an exemplary nucleic acid sequence encoding the S1-4-A09 A61P
V$_H$.
atgggatggtcatgtatcatcctttttctagtagcaactgcaaccggtgtacattctcaggtgcagctgcaggagtcgg
gaccaggactggtgaagccttcggagaccctgtccctcacctgcgttgtctctggtggcatcctcagtagtttttactg
gaactggatccggcagccccaggaaagggactggagtggattggaaacatctattacagtgggagccccaactataat
cccctccttccagagtcgagtcgccatttcggtggacacgtccaagaaccagatctccctgaacctcaagtctgtgaccg
ctgcggacacggccatgtattactgtgtgagagcctcccgcgcttacctttggggagttatcgtccaacggctcttga
cctctggggccagggatccctggtcaccgtctcctca SEQ ID NO: 16 is an exemplary nucleic acid sequence encoding the amino acid
sequence of an IgG1 heavy chain including the S1-4-A09 V$_H$.
atgggatggtcatgtatcatcctttttctagtagcaactgcaaccggtgtacattctcaggtgcagctgcaggagtcgg
gaccaggactggtgaagccttcggagaccctgtccctcacctgcgttgtctctggtggcatcctcagtagtttttactg
gaactggatccggcagccccaggaaagggactggagtggattggaaacatctattacagtgggagccccaactataat
gcctccttccagagtcgagtcgccatttcggtggacacgtccaagaaccagatctccctgaacctcaagtctgtgaccg
ctgcggacacggccatgtattactgtgtgagagcctcccgcgcttacctttggggagttatcgtccaacggctcttga
cctctggggccagggatccctggtcaccgtctcctcagctcgaccaagggcccatcggtcttccccctggcaccctcc
tccaagagcacctctgggggcacagcggccctgggctgcctggtcaaggactacttccccgaacccgtgacggtgtcgt
ggaactcaggcgccctgaccagcggcgtgcacaccttcccggctgtcctacagtcctcaggactctactccctcagcag
cgtggtgaccgtgccctccagcagcttgggcacccagacctacatctgcaacgtgaatcacaagcccagcaacaccaag
gtggacaagaaagttgagcccaaatcttgtgacaaaactcacacatgcccaccgtgcccagcacctgaactcctggggg
gaccgtcagtcttcctcttccccccaaaacccaaggacaccctcatgatctcccggacccctgaggtcacatgcgtggt
ggtggacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatg
gcaaggagtacaagtgcaaggtctccaacaaagccctcccagcccccatcgagaaaaccatctccaaagccaaaggca
gccccgagaaccacaggtgtacaccctgcccccatcccgggatgagctgaccaagaaccaggtcagcctgacctgcctg -continued gtcaaaggcttctatcccagcgacatcgccgtggagtgggagagcaatgggcagccggagaacaactacaagaccacgc
ctcccgtgctggactccgacggctccttcttcctctacagcaagctcaccgtggacaagagcaggtggcagcagggaa
cgtcttctcatgctccgtgatgcatgaggctctgcacaaccactacacgcagaagagcctctccctgtctccgggtaaa
tga SEQ ID NO: 17 is an exemplary nucleic acid sequence encoding the amino acid
sequence of an IgG1 light chain including the S1-4-A09 V$_L$.
atgggatggtcatgtatcatcctttttctagtagcaactgcaaccggtgtccatgcttcctatgagctgactcagccac
cctcagtgtccgtgtccccaggacagacagccaccatcacgtgctctggagataaattgggtgataaatatacttcctg
gttccagcagaggccaggccagtcccctctactggtcatctatcaggatagaaagcggccctcagggctccctgcgcga
ttttctggctccaactctgggaacacagccactctgaccatcagcggcacccaggctatggatgaggctgactatttgt
gtcaggtgtgggacagcggtcggtgttcggcggagggaccaagctgaccgtcctaggtcagcccaaggctgccccctc
ggtcactctgttcccaccctcgagtgaggagcttcaagccaacaaggccacactggtgtgtctcataagtgacttctac
ccgggagccgtgacagtggcctggaaggcagatagcagccccgtcaaggcgggagtggagaccacacccctccaaac
aaagcaacaacaagtacgcggccagcagctacctgagcctgacgcctgagcagtggaagtcccacagaagctacagctg
ccaggtcacgcatgaagggagcaccgtggagaagacagtggcccctacagaatgttcatag SEQ ID NO: 18 is an exemplary nucleic acid sequence encoding the amino acid
sequence of an IgG1 heavy chain including the S1-4-A09 A6IP V$_H$.
atgggatggtcatgtatcatcctttttctagtagcaactgcaaccggtgtacattctcaggtgcagctgcaggagtcgg
gaccaggactggtgaagccttcggagaccctgtccctcacctgcgttgtctctggtggcatcctcagtagttttactg
gaactggatccggcagcccccaggaaagggactggagtggattggaaacatctattacagtgggagccccaactataat
ccctccttccagagtcgagtcgccatttcggtggacacgtccaagaaccagatctccctgaacctcaagtctgtgaccg
ctgcggacacggccatgtattactgtgtgagagcctcccgcgcttacctttgggggagttatcgtccaacggctcttga
cctctggggccagggatccctggtcaccgtctcctcagcgtcgaccaagggcccatcggtcttccccctggcaccctcc
tccaagagcacctctgggggcacagcggccctgggctgcctggtcaaggactacttccccgaaccggtgacggtgtcgt
ggaactcaggcgccctgaccagcggcgtgcacaccttcccggctgtcctacagtcctcaggactctactccctcagcag
cgtggtgaccgtgccctccagcagcttgggcacccagacctacatctgcaacgtgaatcacaagcccagcaacaccaag
gtggacaagaaagttgagcccaaatcttgtgacaaaactcacacatgcccaccgtgcccagcacctgaactcctggggg
gaccgtcagtcttcctcttccccccaaaacccaaggacaccctcatgatctcccggacccctgaggtcacatgcgtggt
ggtgacgtgagccacgaagaccctgaggtcaagttcaactggtacgtggacggcgtggaggtgcataatgccaagaca
aagccgcgggaggagcagtacaacagcacgtaccgtgtggtcagcgtcctcaccgtcctgcaccaggactggctgaatg
gcaaggagtacaagtgcaaggtctccaacaaagcctcccagccccatcgagaaaaccatctccaaagccaaaggca
gccccgagaaccacaggtgtacaccctgccccctcccgggatgagctgaccaagaaccaggtcagcctgacctgcctg
gtcaaaggcttctatcccagcgacatcgccgtggagtgggagagcaatgggcagccggagaacaactacaagaccacgc
ctcccgtgctggactccgacggctccttcttcctctacagcaagctcaccgtggacaagagcaggtggcagcagggaa
cgtcttctcatgctccgtgatgcatgaggctctgcacaaccactacacgcagaagagcctctccctgtctccgggtaaa
tga SEQ ID NO: 19 is an exemplary signal peptide amino acid sequence for an
antibody heavy chain or heavy chain variable region as described herein.
MGWSCIILFLVATATGVHS SEQ ID NO: 20 is an exemplary signal peptide amino acid sequence for an
antibody light chain or light chain variable region as described herein.
MGWSCIILFLVATATGVHA SEQ ID NO: 21 is the amino acid sequence of the V$_H$ of the EVB114 mAb.
EVQLVESGGGLIQPGGSLRLSCAASgfalrmydMHWVRQTIDKRLEWVSAvgpsgdtYYADSVKGRFAVSRENAKNSLS
LQMNSLTAGDTAIYYCvrsdrgvaglfdsWGQGILVTVSS SEQ ID NO: 22 is the amino acid sequence of the V$_L$ of the EVB114 mAb.
DIQMTQSPSSLSASVGDRITITCRASqafdnyVAWYQQRPGKVPKLLISaasALHAGVPSRFSGSGSGTHFTLTISSLQ
PEDVATYYCqnynsapltFGGGTKVEIK SEQ ID NO: 23 is the amino acid sequence of the V$_H$ of the EVB100 mAb.
QVQLQESGPGLVKPSDTLSLTCTVSggslssfyWSWIRQPPGKGLEWIGYiyysgspNYSPSLESRVTMSVDTTRNQIS
LKLDSVTAADTAVYYCvrasrsyywgsyrptafdsWGQGTLVTVSS SEQ ID NO: 24 is the amino acid sequence of the V$_L$ of the EVB100 mAb.
SYELTQPLSVSVSPGQTAIFTCSGDnlgdkyVCWFQQRPGQSPMLLIYqdnKRPSGIPERFSGSNSGNTATLTISGTQS
TDEADYYCqtwdstvvFGGGTKLTVL SEQ ID NO: 25 is an exemplary amino acid sequence of a precursor of the GP from
*Butidibugyo ebolavirus* (GENBANK Acc. No. ACI28624.1, which is incorporated by
reference herein in its entirety).
MVTSGILQLPRERFRKTSFFVWVIILFHKVFPIPLGVVHNNTLQVSDIDKLVCRDKLSSTSQLKSVGLNLEGNGVATDV
PTATKRWGFRAGVPPKVVNYEAGEWAENCYNLDIKKADGSECLPEAPEGVRGFPPRCRYVHKVSGTGPCPEGYAFHKEGA
FFLYDRLASTIIYRSTTFSEGVVAFLILPETKKDFFQSPPLHEPANMTTDPSSYYHTVTLNYVADNFGTNMTNFLFQVD
HLTYVQLEPRFTPQFLVQLNETIYTNGRRSNTTGTLIWKVNPTVDTGVGEWAFWENKKNFTKTLSSEELSVIFVPRAQD
PGSNQKTKVTPTSFANNQTSKNHEDLVPEDPASVVQVRDLQRENTVPTPPPDTVPTTLIPQTMEEQTTSHYEPPNISRN
HQERNNTAHPETLANNPPDNTTPSTPPQDGERTSSHTTPSPRPVPTSTIHPTTRETHIPTTMTTSHDTDSNRPNPIDIS
ESTEPGPLTNTTRGAANLLTGSRRTRREITLRTQAKCNPNLHYWTTQDEGAAIGLAWIPYFGPAAEGIYTEGIMHNQNG
LICGLRQLANETTQALQLFLRATTELRTFSILNRKAIDFLLQRWGGTCHILGPDCCIEPHDWTKNITDKIDQIIHDFID
KPLPDQTDNDNWWTGWRQWVPAGIGITGVIIAVIALLCICKFLL SEQ ID NO: 26 is an exemplary amino acid sequence of a precursor of the GP from
*Sudan ebolavirus* (GENBANK Acc. No. ACR33190.1, which is incorporated by
reference herein in its entirety).
MEGLSLLQLPRDKFRKSSFFVWVIILFQKAFSMPLGVVTNSTLEVTEIDQLVCKDHLASTDQLKSVGLNLEGSGVSTDI
PSATKRWGFRSGVPPKVFSYEAGEWAENCYNLEIKKPDGSECLPPPPDGVRGFPRCRYVHKAQGTGPCPGDYAFHKDGA -continued

```
FFLYDRLASTVIYRGVNFAEGVIAFLILAKPKETFLQSPPIREAVNYTENTSSYYATSYLEYEIENFGAQHSTTLFKIN
NNTFVLLDRPHTPQFLFQLNDTIHLHQQLSNTTGKLIWTLDANINADIGEWAFWENKKNLSEQLRGEELSFETLSLNET
EDDDATSSRTTKGRISDRATRKYSDLVPKDSPGMVSLHVPEGETTLPSQNSTEGRRVDVNTQETITETTATIIGTNGNN
MQISTIGTGLSSSQILSSSPTMAPSPETQTSTTYTPKLPVMTTEESTTPPRNSPGSTTEAPTLTTPENITTAVKTVLPQ
ESTSNGLITSTVTGILGSLGLRKRSRRQVNTRATGKCNPNLHYWTAQEQHNAAGIAWIPYFGPGAEGIYTEGLMHNQNA
LVCGLRQLANETTQALQLFLRATTELRTYTILNRKAIDFLLRRWGGTCRILGPDCCIEPHDWTKNITDKINQIIHDFID
NPLPNQDNDDNWWTGWRQWIPAGIGITGIIIAIIALLCVCKLLC

SEQ ID NO: 27 is an exemplary amino acid sequence of a precursor of the GP from
Zaire ebolavirus (GENBANK Acc. No. AIO11753.1, which is incorporated by
reference herein in its entirety).
MGVTGILQLPRDRFKKTSFFLWVIILFQRTFSIPLGVIHNSTLQVSDVDKLVCRDKLSSTNQLRSVGLNLEGNGVATDV
PSATKRWGFRSGVPPKVVNYEAGEWAENCYNLEIKKPDGSECLPAAPDGIRGFPRCRYVHKVSGTGPCAGDFAFHKEGA
FFLYDRLASTVIYRGTTFAEGVVAFLILPQAKKDFFSSHPLREPVNATEDPSSGYYSTTIRYQATGFGTNETEYLFEVD
NLTYVQLESRFTPQFLLQLNETIYTSGKRSNTTGKLIWKVNPEIDTTIGEWAFWETKKNLTRKIRSEELSFTAVSNRAK
NISGQSPARTSSDPGTNTTTEDHKIMASENSSAMVQVHSQGREAAVSHLTTLATISTSPQPPTTKPGPDNSTHNTPVYK
LDISEATQAEQHHRRTDNDSTTSDTPPAMTAAGPPKAENTNTSKGTDLPDPATTTSPQNHSETAGNNKTHHQDTGEESA
SSGKLGLITNTIAGVAGLITGGRRTRREAIVNAQPKCNPKLHYWTTQDEGAAIGLAWIPYFGPAAEGIYTEGLMHNQDG
LICGLRQLANETTQALQLFLRATTELRTFSILNRKAIDFLLQRWGGTCHILGPDCCIEPHDWTKNITDKIDQIIHDFVD
KTLPDQGDNDNWWTGWRQWIPAGIGVTGVIIAVIALFCICKFVF SEQ ID NO: 28 is an exemplary amino acid sequence of a precursor of the GP from
Reston ebolavirus (GENBANK Acc. No. AAC54891.1, which is incorporated by
reference herein in its entirety).
MGSGYQLLQLPRERFRKTSFLVWVIILFQRAISMPLGIVTNSTLKATEIDQLVCRDKLSSTSQLKSVGLNLEGNGIATD
VPSATKRWGFRSGVPPKVVSYEAGEWAENCYNLEIKKSDGSECLPLPPDGVRGFPRCRYVHKVQGTGPCPGDLAFHKNG
AFFLYDRLASTVIYRGTTFTEGVVAFLILSEPKKHFWKATPAHEPVNTTDDSTSYYMTLTLSYEMSNFGGKESNTLFKV
DNHTYVQLDRPHTPQFLVQLNETLRRNNRLSNSTGRLTWTLDPKIEPDVGEWAFWETKKKFSQQLHGENLHFQILSTHT
NNSSDQSPAGTVQGKISYHPPTNNSELVPTDSPPVVSVLTAGRTEEMSTQGLTNGETITGFTANPMTTTIAPSPTMTSE
VDNNVPSEQPNNTASIEDSPPSASNETIDHSEMNPIQGSNNSAQSPQTKTTPAPTASPMTQDPQETANSSKLGTSPGSA
AEPSQPGFTINTVSKVADSLSPTRKQKRSVRQNTANKCNPDLHYWTAVDEGAAVGLAWIPYFGPAAEGIYIEGVMHNQN
GLICGLRQLANETTQALQLFLRATTELRTYSLLNRKAIDFLLQRWGGTCRILGPSCCIEPHDWTKNITDEINQIKHDFI
DNPLPDHGDDLNLWTGWRQWIPAGIGIIGVIIAIIALLCICKILC SEQ ID NO: 29 is an exemplary amino acid sequence of a precursor of the GP from
Taï Forest ebolavirus (GENBANK Acc. No. ACI28632.1, which is incorporated by
reference herein in its entirety).
MGASGILQLPRERFRKTSFFVWVIILFHKVFSIPLGVVHNNTLQVSDIDKFVCRDKLSSTSQLKSVGLNLEGNGVATDV
PTATKRWGFRAGVPPKVVNCEAGEWAENCYNLAIKKVDGSECLPEAPEGVRDFPRCRYVHKVSGTGPCPGGLAFHKEGA
FFLYDRLASTIIYRGTTFAEGVIAFLILPKARKDFFQSPPLHEPANMTTDPSSYYHTTTINYVVDNFGTNTTEFLFQVD
HLTYVQLEARFTPQFLVLLNETIYSDNRRSNTTGKLIWKINPTVDTSMGEWAFWENKKNFTKTLSSEELSFVPVPETQN
QVLDTTATVSPPISAHNHAAEDHKELVSEDSTPVVQMQNIKGKDTMPTTVTGVPTTTPSPFPINARNTDHTKSFIGLEG
PQEDHSTTQPAKTTSQPTNSTESTTLNPTSEPSSRGTGPSSPTVPNTTESHAELGKTTPTTLPEQHTAASAIPRAVHPD
ELSGPGFLTNTIRGVTNLLTGSRRKRRDVTPNTQPKCNPKLHYWTALDEGAAIGLAWIPYFGPAAEGIYTEGIMENQNG
LICGLRQLANETTQALQLFLRATTELRTFSILNRKAIDFLLQRWGGTCHILGPDCCIEPQDWTKNITDKIDQIIHDFVD
NNLPNQNDGSNWWTGWKQWVPAGIGITGVIIAIIALLCICKFML SEQ ID NO: 30 is an exemplary amino acid sequence of a precursor of the soluble
form of GP from Zaire ebolavirus (GENBANK Acc. No. AAD14584.1, which is
incorporated by reference herein in its entirety).
MGVTGILQLPRDRFKRTSFFLWVIILFQRTFSIPLGVIHNSTLQVSDVDKLVCRDKLSSTNQLRSVGLNLEGNGVATDV
PSATKRWGFRSGVPPKVVNYEAGEWAENCYNLEIKKPDGSECLPAAPDGIRGFPRCRYVHKVSGTGPCAGDFAFHKEGA
FFLYDRLASTVIYRGTTFAEGVVAFLILPQAKKDFFSSHPLREPVNATEDPSSGYYSTTIRYQATGFGTNETEYLFEVD
NLTYVQLESRFTPQFLLQLNETIYTSGKRSNTTGKLIWKVNPEIDTTIGEWAFWETKKTSLEKFAVKSCLSQLYQTEPK
TSVVRVRRELLPTQGPTQQLKTTKSWLQKIPLQWFKCTVKEGKLQCRI SEQ ID NO: 31 is the amino acid sequence of a region of the mAb100 UCA heavy
chain (see FIG. 11).
```

DETAILED DESCRIPTION

I. Summary of Terms

Unless otherwise noted, technical terms are used according to conventional usage. Definitions of many common terms in molecular biology may be found in Krebs et al. (eds.), *Lewin's genes XII*, published by Jones & Bartlett Learning, 2017. As used herein, the singular forms "a," "an," and "the," refer to both the singular as well as plural, unless the context clearly indicates otherwise. For example, the term "an antigen" includes singular or plural antigens and can be considered equivalent to the phrase "at least one antigen." As used herein, the term "comprises" means "includes." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described herein. In case of conflict, the present specification, including explanations of terms, will control. In addition, the materials, methods, and examples are illustrative only and not intended to be limiting. To facilitate review of the various embodiments, the following explanations of terms are provided:

Administration: The introduction of a composition into a subject by a chosen route. Administration can be local or systemic. For example, if the chosen route is intravenous, the composition is administered by introducing the composition into a vein of the subject. Exemplary routes of administration include, but are not limited to, oral, injection (such as subcutaneous, intramuscular, intradermal, intraperitoneal, and intravenous), sublingual, rectal, transdermal (for example, topical), intranasal, vaginal, and inhalation routes.

Antibody and Antigen Binding Fragment: An immunoglobulin, antigen-binding fragment, or derivative thereof, that specifically binds and recognizes an analyte (antigen) such as Ebolavirus GP. The term "antibody" is used herein in the broadest sense and encompasses various antibody structures, including but not limited to monoclonal antibodies, polyclonal antibodies, multispecific antibodies (e.g., bispecific antibodies), and antibody fragments, so long as they exhibit the desired antigen-binding activity.

Non-limiting examples of antibodies include, for example, intact immunoglobulins and variants and fragments thereof known in the art that retain binding affinity for the antigen. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Antibody fragments include antigen binding fragments either produced by the modification of whole antibodies or those synthesized de novo using recombinant DNA methodologies (see, e.g., Kontermann and Dübel (Eds.), *Antibody Engineering*, Vols. 1-2, $2^{nd}$ ed., Springer-Verlag, 2010).

A single-chain antibody (scFv) is a genetically engineered molecule containing the $V_H$ and $V_L$ domains of one or more antibody(ies) linked by a suitable polypeptide linker as a genetically fused single chain molecule (see, for example, Bird et al., *Science,* 242(4877):423-426, 1988; Huston et al., *Proc. Natl. Acad. Sci. U.S.A.,* 85(16):5879-5883, 1988; Ahmad et al., *Clin. Dev. Immunol.,* 2012, doi:10.1155/2012/980250; Marbry and Snavely, *IDrugs,* 13(8):543-549, 2010). The intramolecular orientation of the $V_H$-domain and the $V_L$-domain in a scFv, is typically not decisive for scFvs. Thus, scFvs with both possible arrangements ($V_H$-domain-linker domain-$V_L$-domain; $V_L$-domain-linker domain-$V_H$-domain) may be used.

In a dsFv the $V_H$ and $V_L$ have been mutated to introduce a disulfide bond to stabilize the association of the chains. Diabodies also are included, which are bivalent, bispecific antibodies in which $V_H$ and $V_L$ domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., *Proc. Natl. Acad. Sci. U.S.A.,* 90(14):6444-6448, 1993; Poljak et al., *Structure,* 2(12):1121-1123, 1994).

Antibodies also include genetically engineered forms such as chimeric antibodies (such as humanized murine antibodies) and heteroconjugate antibodies (such as bispecific antibodies).

Typically, a naturally occurring immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda ($\lambda$) and kappa ($\kappa$). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain). In several embodiments, the $V_H$ and $V_L$ combine to specifically bind the antigen. In additional embodiments, only the $V_H$ is required. For example, naturally occurring camelid antibodies consisting of a heavy chain only are functional and stable in the absence of light chain. Any of the disclosed antibodies can include a heterologous constant domain. For example the antibody can include constant domain that is different from a native constant domain, such as a constant domain including one or more modifications (such as the "LS" mutations) to increase half-life.

References to "$V_H$" or "$V_H$" refer to the variable region of an antibody heavy chain, including that of an antigen binding fragment, such as Fv, scFv, dsFv or Fab. References to "$V_L$" or "VL" refer to the variable domain of an antibody light chain, including that of an Fv, scFv, dsFv or Fab.

The $V_H$ and $V_L$ contain a "framework" region interrupted by three hypervariable regions, also called "complementarity-determining regions" or "CDRs" (see, e.g., Kabat et al., *Sequences of Proteins of Immunological Interest,* $5^{th}$ ed., NIH Publication No. 91-3242, Public Health Service, National Institutes of Health, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. (Sequences of Proteins of Immunological Interest, $5^{th}$ ed., NIH Publication No. 91-3242, Public Health Service, National Institutes of Health, U.S. Department of Health and Human Services, 1991; "Kabat" numbering scheme), Al-Lazikani et al., ("Standard conformations for the canonical structures of immunoglobulins," *J. Mol. Bio.,* 273(4):927-948, 1997; "Chothia" numbering scheme), and Lefranc et al. ("IMGT unique numbering for immunoglobulin and T cell receptor variable domains and Ig superfamily V-like domains," *Dev. Comp. Immunol.,* 27(1):55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the $V_H$ of the antibody in which it is found, whereas a $V_L$ CDR1 is the CDR1 from the $V_L$ of the antibody in which it is found. Light chain CDRs are sometimes referred to as LCDR1, LCDR2, and LCDR3. Heavy chain CDRs are sometimes referred to as HCDR1, HCDR2, and HCDR3.

A "monoclonal antibody" is an antibody obtained from a population of substantially homogeneous antibodies, that is, the individual antibodies comprising the population are identical and/or bind the same epitope, except for possible variant antibodies, for example, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein. In some examples monoclonal antibodies are isolated from a subject. Monoclonal antibodies can have conservative amino acid substitutions which have substantially no effect on antigen binding or other immunoglobulin functions. (See, for example, Greenfield (Ed.), *Antibodies: A Laboratory Manual*, $2^{nd}$ ed. New York: Cold Spring Harbor Laboratory Press, 2014.)

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. *Phage display: A Laboratory Manuel.* $1^{st}$ ed. New York: Cold Spring Harbor Laboratory Press, 2004; Lonberg, *Nat. Biotechnol.*, 23(9): 1117-1125, 2005; Lonberg, *Curr. Opin. Immunol.* 20(4):450-459, 2008)

Antibody or antigen binding fragment that neutralizes an ebolavirus: An antibody or antigen binding fragment that specifically binds to an ebolavirus GP (such as *Zaire ebolavirus* GP) in such a way as to inhibit a biological function associated with the ebolavirus GP (such as binding to its target receptor). In several embodiments, an antibody or antigen binding fragment that neutralizes an ebolavirus reduces the infectious titer of the ebolavirus. In some embodiments, an antibody or antigen binding fragment that specifically binds to an ebolavirus GP can neutralize two or more (such as three, four, five, or more) species of Ebolavirus.

Antibody self-reactivity or autoreactivity: A property of an antibody, whereby the antibody reacts with self-epitopes, that is epitopes of proteins and/or lipids that are produced by the subject. An antibody that does not have self-reactivity does not substantially bind to epitopes or lipids present on the membrane of a cell from a subject. Methods of determining if an antibody reacts with self-epitopes are known to the person of ordinary skill in the art. In one example, antibody self-reactivity is evaluated using HEp-2 cell staining, a cardiolipin binding assay, or an anti-nuclear antigen (ANA) assay. The anti-ANA assay can include an anti-ANA LUMINEX® assay or an ANA cell-staining assay, for example. In several embodiments, a disclosed antibody is not self-reactive (or autoreactive), or is minimally self-reactive. In one non-limiting example, a disclosed antibody is less self-reactive that the mAb100 and/or mAb114 antibody. For example, the disclosed antibody or antigen binding fragment can have no more than 90% autoreactivity when compared to the mAb100 and/or mAb114 antibody, for example as measured using HEp-2 cell staining, cardiolipin binding, an anti-ANA LUMINEX® assay, or an ANA cell-staining assay. In another non-limiting example, a disclosed antibody does not have self-reactivity above background levels, for example, as measured using an anti-ANA LUMINEX® assay or an ANA cell-staining assay.

Biological sample: A sample obtained from a subject. Biological samples include all clinical samples useful for detection of disease or infection (for example, ebolavirus infection) in subjects, including, but not limited to, cells, tissues, and bodily fluids, such as blood, derivatives and fractions of blood (such as serum), cerebrospinal fluid; as well as biopsied or surgically removed tissue, for example tissues that are unfixed, frozen, or fixed in formalin or paraffin. In a particular example, a biological sample is obtained from a subject having or suspected of having an ebolavirus infection.

Bispecific antibody: A recombinant molecule composed of two different antigen binding domains that consequently binds to two different antigenic epitopes. Bispecific antibodies include chemically or genetically linked molecules of two antigen-binding domains. The antigen binding domains can be linked using a linker. The antigen binding domains can be monoclonal antibodies, antigen-binding fragments (e.g., Fab, scFv), or combinations thereof. A bispecific antibody can include one or more constant domains, but does not necessarily include a constant domain.

Conditions sufficient to form an immune complex: Conditions which allow an antibody or antigen binding fragment to bind to its cognate epitope to a detectably greater degree than, and/or to the substantial exclusion of, binding to substantially all other epitopes. Conditions sufficient to form an immune complex are dependent upon the format of the binding reaction and typically are those utilized in immunoassay protocols or those conditions encountered in vivo. See Greenfield (Ed.), *Antibodies: A Laboratory Manual,* $2^{nd}$ ed. New York: Cold Spring Harbor Laboratory Press, 2014, for a description of immunoassay formats and conditions. The conditions employed in the methods are "physiological conditions" which include reference to conditions (e.g., temperature, osmolarity, pH) that are typical inside a living mammal or a mammalian cell. While it is recognized that some organs are subject to extreme conditions, the intra-organismal and intracellular environment normally lies around pH 7 (e.g., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

The formation of an immune complex can be detected through conventional methods, for instance immunohistochemistry (IHC), immunoprecipitation (IP), flow cytometry, immunofluorescence microscopy, ELISA, immunoblotting (for example, Western blot), magnetic resonance imaging (MRI), computed tomography (CT) scans, radiography, and affinity chromatography. Immunological binding properties of selected antibodies may be quantified using known methods.

Conjugate: A complex of two molecules linked together, for example, linked together by a covalent bond. In one embodiment, an antibody is linked to an effector molecule; for example, an antibody that specifically binds to ebolavirus GP covalently linked to an effector molecule. The linkage can be by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because conjugates can be prepared from two molecules with separate functionalities, such as an antibody and an effector molecule, they are also sometimes referred to as "chimeric molecules."

Conservative amino acid substitution: "Conservative" amino acid substitutions are those substitutions that do not substantially affect a function of a protein, such as the ability of the protein to interact with a target protein.

In some embodiments, a conservative amino acid substitution in an ebolavirus GP-specific antibody is one that does not reduce binding of the antibody to ebolavirus GP by more than 10% (such as by more than 5%) compared to the ebolavirus GP binding of the corresponding antibody lacking the conservative amino acid substitution. In some embodiments, the ebolavirus GP-specific antibody can include up to 1, 2, 3, 4, 5, 6, 7, 8, 9, or up to 10 conservative substitutions compared to a reference antibody and retain specific binding activity for GP, and/or ebolavirus neutralization activity.

Typically, individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form, which can take place either in vivo or in vitro. Contacting includes contact between one molecule and another molecule, for example the amino acid on the surface of one polypeptide, such as an antigen, that contacts another polypeptide, such as an antibody. Contacting can also include contacting a cell for example by placing an antibody in direct physical association with a cell.

Control: A reference standard. In some embodiments, the control is a negative control, such as sample obtained from a healthy patient not infected with an ebolavirus. In other embodiments, the control is a positive control, such as a tissue sample obtained from a patient diagnosed with an ebolavirus infection. In still other embodiments, the control is a historical control or standard reference value or range of values (such as a previously tested control sample, such as a group of EVD patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, or at least about 500%.

Degenerate variant: In the context of the present disclosure, a "degenerate variant" refers to a polynucleotide encoding a protein (for example, an antibody that specifically binds ebolavirus GP or a variable region thereof) that comprises a sequence that is degenerate as a result of the genetic code. There are twenty natural amino acids, most of which are specified by more than one codon. Therefore, all degenerate nucleotide sequences are included as long as the amino acid sequence of the antibody that binds ebolavirus GP encoded by the nucleotide sequence is unchanged.

Detectable marker: A detectable molecule (also known as a label) that is conjugated directly or indirectly to a second molecule, such as an antibody, to facilitate detection of the second molecule. For example, the detectable marker can be capable of detection by ELISA, spectrophotometry, flow cytometry, microscopy or diagnostic imaging techniques (such as CT scans, MRIs, ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). Methods for using detectable markers and guidance in the choice of detectable markers appropriate for various purposes are discussed for example in Green and Sambrook (*Molecular Cloning: A Laboratory Manual,* 4$^{th}$ ed., New York: Cold Spring Harbor Laboratory Press, 2012) and Ausubel et al. (Eds.) (*Current Protocols in Molecular Biology,* New York: John Wiley and Sons, including supplements, 2017).

Detecting: To identify the existence, presence, or fact of something.

Ebolavirus: A genus of enveloped, non-segmented, negative-sense, single-stranded RNA viruses that causes EVD, formerly known as Ebola hemorrhagic fever (EHF), in humans. Ebolaviruses spread through human-to-human transmission, with infection resulting from direct contact with blood, secretions, organs or other bodily fluids of infected people, and indirect contact with environments contaminated by such fluids.

The symptoms of ebolavirus infection and EVD are well-known. Briefly, in humans, ebolaviruses have an initial incubation period of 2 to 21 days (7 days on average, depending on the Ebolavirus species) followed by rapid onset of non-specific symptoms such as fever, extreme fatigue, gastrointestinal complaints, abdominal pain, anorexia, headache, myalgias and/or arthralgias. These initial symptoms last for about 2 to 7 days after which more severe symptoms related to hemorrhagic fever occur, including hemorrhagic rash, epistaxis, mucosal bleeding, hematuria, hemoptysis, hematemesis, melena, conjunctival hemorrhage, tachypnea, confusion, somnolence, and hearing loss. In general, the symptoms last for about 7 to 14 days after which recovery may occur. Death can occur 6 to 16 days after the onset of symptoms. People are infectious as long as their blood and secretions contain the virus, which in some instances can be more than 60 days.

Immunoglobulin M (IgM) antibodies to the virus appear 2 to 9 days after infection whereas immunoglobulin G (IgG) antibodies appear approximately 17 to 25 days after infection, which coincides with the recovery phase. In survivors of EVD, both humoral and cellular immunity are detected, however, their relative contribution to protection is unknown.

Five distinct species of Ebolavirus are known, including *Bundibugyo ebolavirus, Reston ebolavirus, Sudan ebolavirus, Taï Forest ebolavirus*, and *Zaire ebolavirus*. Bundibugyo ebolavirus, Sudan ebolavirus, and *Zaire ebolavirus* have been associated with large outbreaks of EVD in Africa and reported case fatality rates of up to 90%. Exemplary amino acid sequences of GP from *Bundibugyo ebolavirus, Reston ebolavirus, Sudan ebolavirus, Taï Forest ebolavirus*, and *Zaire ebolavirus* are set forth as SEQ ID NOs: 25-29.

The ebolavirus genome includes about 19 kb, which encode seven structural proteins including NP (a nucleoprotein), VP35 (a polymerase cofactor), VP30 (a transcriptional activator), VP24, L (a RNA polymerase), and GP (a glycoprotein).

Ebolavirus glycoprotein (GP): The virion-associated transmembrane glycoprotein of *Ebolavirus* is initially synthesized as a precursor protein of about 676 amino acids in size, designated $GP_0$. Individual $GP_0$ polypeptides form a homotrimer and undergo glycosylation and processing to remove the signal peptide, as well as cleavage by a cellular protease between approximately positions 501/502 (from the initiating methionine) to generate separate $GP_1$ and $GP_2$ polypeptide chains, which remain associated via disulfide bonds as $GP_1/GP_2$ protomers within the homotrimer. The extracellular $GP_1$ trimer (approx. 153 kDa) is derived from the amino-terminal portion of the $GP_0$ precursors, and the $GP_2$ trimer (approx. 59 kDa), which includes extracellular, transmembrane, and cytosolic domains, is derived from the carboxyl-terminal portion of the $GP_0$ precursors. $GP_1$ is responsible for attachment to new host cells while $GP_2$ mediates fusion with those cells.

A variant transcript of the gene encoding ebolavirus GP encodes a soluble glycoprotein (sGP) that is secreted from the viral host cell. The transcript for sGP is created via stuttering of the polymerase on a slippery sequence composed of 7U's resulting in either transcript with 7A's, which codes for sGP, or 8A's, which codes for GP. sGP and $GP_1$ are identical in their first 295 N-terminal amino acids, whereas the remaining 69 C-terminal amino acids of sGP and 206 amino acids of $GP_1$ are encoded by different reading frames. It has been suggested that secreted sGP may effectively bind antibodies that might otherwise be protective (see, e.g., Sanchez et al., *Proc. Natl. Acad. Sci. U.S.A.*, 93(8): 3602-3607, 1996; and Volchkov et al., *Virology*, 245(1): 110-119, 1998, each of which is incorporated by reference herein in its entirety).

Comparisons of the predicted amino acid sequences for the GPs of the different ebolaviruses show conservation of amino acids in the amino-terminal and carboxy-terminal regions with a highly variable region in the middle of the protein (Sanchez et al., *Virus Res.* 29(3): 215-240, 1993; Sanchez et al. *Proc. Natl. Acad. Sci. U.S.A.*, 93(8): 3602-3607, 1996). The GPs of the ebolaviruses are highly glycosylated and contain both N-linked and O-linked carbohydrates that contribute up to 50% of the molecular weight of the protein. Most of the glycosylation sites are found in the central variable region of GP.

The numbering used in the disclosed ebolavirus GPs and fragments thereof is relative to the *Zaire ebolavirus* GP protein set forth as SEQ ID NO: 27, unless context indicates otherwise.

Effective amount: A quantity of a specific substance sufficient to achieve a desired effect in a subject to whom the substance is administered. For instance, this can be the amount necessary to inhibit an infection with one or more ebolaviruses or to measurably alter outward symptoms of the infection.

In some embodiments, administration of an effective amount of a disclosed antibody or antigen binding fragment that binds to ebolavirus GP can reduce or inhibit an ebolavirus infection (for example, as measured by infection of cells, or by number or percentage of subjects infected by the ebolavirus, or by an increase in the survival time of infected subjects, or by reduction in symptoms associated with ebolavirus infection) by a desired amount, for example by at least 10%, at least 20%, at least 50%, at least 60%, at least 70%, at least 80%, at least 90%, at least 95%, at least 98%, or even at least 100% (elimination or prevention of detectable ebolavirus infection), as compared to a suitable control.

The effective amount of an antibody or antigen binding fragment that specifically binds ebolavirus GP that is administered to a subject to inhibit ebolavirus infection will vary depending upon a number of factors associated with that subject, for example the overall health and/or weight of the subject. An effective amount can be determined by varying the dosage and measuring the resulting response, such as, for example, a reduction in pathogen titer. Effective amounts also can be determined through various in vitro, in vivo or in situ immunoassays.

An effective amount encompasses a fractional dose that contributes in combination with previous or subsequent administrations to attaining an effective response. For example, an effective amount of an agent can be administered in a single dose, or in several doses, for example daily, during a course of treatment lasting several days or weeks. However, the effective amount can depend on the subject being treated, the severity and type of the condition being treated, and the manner of administration. A unit dosage form of the agent can be packaged in an amount, or in multiples of the effective amount, for example, in a vial (e.g., with a pierceable lid) or syringe having sterile components.

Effector molecule: A molecule intended to have or produce a desired effect; for example, a desired effect on a cell to which the effector molecule is targeted. Effector molecules can include, for example, polypeptides and small molecules. In one non-limiting example, the effector molecule is a toxin. Some effector molecules may have or produce more than one desired effect.

Epitope: An antigenic determinant. These are particular chemical groups or peptide sequences on a molecule that are antigenic, i.e. that elicit a specific immune response. An antibody specifically binds a particular antigenic epitope on a polypeptide. In some examples, a disclosed antibody specifically binds to an epitope on GP from ebolavirus.

Expression: Transcription or translation of a nucleic acid sequence. For example, an encoding nucleic acid sequence (such as a gene) can be expressed when its DNA is transcribed into RNA or an RNA fragment, which in some examples is processed to become mRNA. An encoding nucleic acid sequence (such as a gene) may also be expressed when its mRNA is translated into an amino acid sequence, such as a protein or a protein fragment. In a particular example, a heterologous gene is expressed when it is transcribed into RNA. In another example, a heterologous gene is expressed when its RNA is translated into an amino acid sequence. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcriptional terminators, a start codon (ATG) in front of a protein-encoding gene, splice signals for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

Expression vector: A vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Fc region: The constant region of an antibody excluding the first heavy chain constant domain. Fc region generally refers to the last two heavy chain constant domains of IgA, IgD, and IgG, and the last three heavy chain constant domains of IgE and IgM. An Fc region may also include part or all of the flexible hinge N-terminal to these domains. For IgA and IgM, an Fc region may or may not include the tailpiece, and may or may not be bound by the J chain. For IgG, the Fc region is typically understood to include immunoglobulin domains Cγ2 and Cγ3 and optionally the lower part of the hinge between Cγ1 and Cγ2. Although the boundaries of the Fc region may vary, the human IgG heavy chain Fc region is usually defined to include residues following C226 or P230 to the Fc carboxyl-terminus, wherein the numbering is according to Kabat. For IgA, the Fc region includes immunoglobulin domains Cα2 and Cα3 and optionally the lower part of the hinge between Cα1 and Cα2.

IgA: A polypeptide belonging to the class of antibodies that are substantially encoded by a recognized immunoglobulin alpha gene. In humans, this class or isotype comprises $IgA_1$ and $IgA_2$. IgA antibodies can exist as monomers, polymers (referred to as pIgA) of predominantly dimeric form, and secretory IgA. The constant chain of wild-type IgA contains an 18-amino-acid extension at its C-terminus called the tail piece (tp). Polymeric IgA is secreted by plasma cells with a 15-kDa peptide called the J chain linking two monomers of IgA through the conserved cysteine residue in the tail piece.

IgG: A polypeptide belonging to the class or isotype of antibodies that are substantially encoded by a recognized immunoglobulin gamma gene. In humans, this class comprises IgG1, IgG2, $IgG_3$, and IgG4.

Immune complex: The binding of antibody or antigen binding fragment (such as a scFv) to a soluble antigen forms an immune complex. The formation of an immune complex can be detected through conventional methods, for instance immunohistochemistry, immunoprecipitation, flow cytometry, immunofluorescence microscopy, ELISA, immunoblotting (for example, Western blot), magnetic resonance imaging, CT scans, radiography, and affinity chromatography.

Inhibiting a disease or condition: Reducing the full development of a disease or condition in a subject, for example, reducing the full development of EVD in a subject who has an ebolavirus infection, and/or reducing ebolavirus infection in a subject or population of subjects at risk thereof. This includes neutralizing, antagonizing, prohibiting, preventing, restraining, slowing, disrupting, stopping, or reversing progression or severity of the disease or condition.

Inhibiting a disease or condition refers to a prophylactic intervention administered before the disease or condition has begun to develop (for example a treatment initiated in a subject at risk of an ebolavirus infection, but not infected by an ebolavirus) that reduces subsequent development of the disease or condition, and also to amelioration of one or more signs or symptoms of the disease or condition following development. The term "ameliorating," with reference to inhibiting a disease or condition refers to any observable beneficial effect of the intervention intended to inhibit the disease or condition. The beneficial effect can be evidenced, for example, by a delayed onset of clinical symptoms of the disease or condition in a susceptible subject, a reduction in severity of some or all clinical symptoms of the disease or condition, a slower progression of the disease or condition, an improvement in the overall health or well-being of the subject, a reduction in infection, or by other parameters well known in the art that are specific to the particular disease or condition.

In some embodiments, an antibody or antigen binding fragment that specifically binds to ebolavirus GP and is neutralizing inhibits infection of a human subject by an ebolavirus (such as *Zaire ebolavirus*), for example, by at least 50% (such as at least 60%, at least 70%, at least 80%, at least 90%, or more) compared to a control antibody or antigen binding fragment.

Isolated: A biological component (such as a nucleic acid, peptide, protein or protein complex, for example an antibody) that has been substantially separated, produced apart from, or purified away from other biological components in the cell of the organism in which the component naturally occurs, that is, other chromosomal and extra-chromosomal DNA and RNA, and proteins. Thus, isolated nucleic acids, peptides and proteins include nucleic acids and proteins purified by standard purification methods. The term also embraces nucleic acids, peptides and proteins prepared by recombinant expression in a host cell, as well as, chemically synthesized nucleic acids. An isolated nucleic acid, peptide or protein, for example an antibody, can be at least 50%, at least 60%, at least 70%, at least 80%, at least 90%, at least 95%, at least 96%, at least 97%, at least 98%, or at least 99% pure.

Kabat position: A position of a residue in an amino acid sequence that follows the numbering convention delineated by Kabat et al. (*Sequences of Proteins of Immunological Interest*, 5$^{th}$ ed., NIH Publication No. 91-3242, Public Health Service, National Institutes of Health, U.S. Department of Health and Human Services, 1991).

Linker: A bi-functional molecule that can be used to link two molecules into one contiguous molecule, for example, to link an effector molecule to an antibody. Non-limiting examples of peptide linkers include glycine-serine linkers.

The terms "conjugating," "joining," "bonding," or "linking" can refer to making two molecules into one contiguous molecule; for example, linking two polypeptides into one contiguous polypeptide, or covalently attaching an effector molecule or detectable marker radionuclide or other molecule to a polypeptide, such as an scFv. The linkage can be either by chemical or recombinant means. "Chemical means" refers to a reaction between the antibody moiety and the effector molecule such that there is a covalent bond formed between the two molecules to form one molecule.

Nucleic acid (molecule or sequence): A deoxyribonucleotide or ribonucleotide polymer or combination thereof including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides.

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and the non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

Operably linked A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Pharmaceutically acceptable carriers: The pharmaceutically acceptable carriers of use are conventional. *Remington: The Science and Practice of Pharmacy*, 22$^{nd}$ ed., London, UK: Pharmaceutical Press, 2013, describes compositions and formulations suitable for pharmaceutical delivery of the disclosed agents.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, added preservatives (such as non-natural preservatives), and pH buffering agents and the like, for example sodium acetate or sorbitan monolaurate. In particular examples, the pharmaceutically acceptable carrier is sterile and suitable for parenteral administration to a subject for example, by injection. In some embodiments, the active agent and pharmaceutically acceptable carrier are provided in a unit dosage form such as a pill or in a selected quantity in a vial. Unit dosage forms can include one dosage or multiple dosages (for example, in a vial from which metered dosages of the agents can selectively be dispensed).

Polypeptide: A polymer in which the monomers are amino acid residues that are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. A polypeptide includes both naturally occurring proteins, as well as those that are recombinantly or synthetically produced. A polypeptide has an amino terminal (N-terminal) end and a carboxy-terminal (C-terminal) end. In some embodiments, the polypeptide is a disclosed antibody or a fragment thereof.

Purified: The term purified does not require absolute purity; rather, it is intended as a relative term. Thus, for example, a purified peptide preparation is one in which the peptide or protein (such as an antibody) is more enriched than the peptide or protein is in its natural environment within a cell. In one embodiment, a preparation is purified such that the protein or peptide represents at least 50% of the total peptide or protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence. In several embodiments, a recombinant protein is encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences are. Homologs and variants of a $V_L$ or a $V_H$ of an antibody that specifically binds a target antigen are typically characterized by possession of at least about 75%, for example at least about 80%, 85%, 90%, 91%, 92%, 93%, 94%, 95%, 96%, 97%, 98% or 99% sequence identity counted over the full-length alignment with the amino acid sequence of interest.

Methods of alignment of sequences for comparison are well known in the art. Various programs and alignment algorithms are described in: Smith and Waterman, *Adv. Appl. Math.* 2(4):482-489, 1981; Needleman and Wunsch, *J. Mol. Biol.* 48(3):443-453, 1970; Pearson and Lipman, *Proc. Natl. Acad. Sci. U.S.A.* 85(8):2444-2448, 1988; Higgins and Sharp, *Gene*, 73(1):237-244, 1988; Higgins and Sharp, *Bioinformatics*, 5(2):151-3, 1989; Corpet, *Nucleic Acids Res.* 16(22):10881-10890, 1988; Huang et al. *Bioinformatics*, 8(2):155-165, 1992; and Pearson, *Methods Mol. Biol.* 24:307-331, 1994. Altschul et al., *J. Mol. Biol.* 215(3):403-410, 1990, presents a detailed consideration of sequence alignment methods and homology calculations. The NCBI Basic Local Alignment Search Tool (BLAST) (Altschul et al., *J. Mol. Biol.* 215(3):403-410, 1990) is available from several sources, including the National Center for Biological Information and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

Specifically bind: When referring to an antibody or antigen binding fragment, refers to a binding reaction which determines the presence of a target protein in the presence of a heterogeneous population of proteins and other biologics. Thus, under designated conditions, an antibody binds preferentially to a particular target protein, peptide or polysaccharide (such as an antigen present on the surface of a pathogen, for example ebolavirus GP) and does not bind in a significant amount to other proteins present in the sample or subject. Specific binding can be determined by methods known in the art. See Greenfield (Ed.), *Antibodies: A Laboratory Manual*, $2^{nd}$ ed. New York: Cold Spring Harbor Laboratory Press, 2014, for a description of immunoassay formats and conditions that can be used to determine specific immunoreactivity.

With reference to an antibody-antigen complex, specific binding of the antigen and antibody has a $K_D$ of less than about $10^{-7}$ Molar, such as less than about $10^{-8}$ Molar, $10^{-9}$, or even less than about $10^{-10}$ Molar. $K_D$ refers to the dissociation constant for a given interaction, such as a polypeptide-ligand interaction or an antibody-antigen interaction. For example, for the bimolecular interaction of an antibody or antigen binding fragment and an antigen it is the concentration of the individual components of the bimolecular interaction divided by the concentration of the complex.

An antibody that specifically binds to an epitope on ebolavirus GP is an antibody that binds substantially to ebolavirus GP, including cells or tissue expressing ebolavirus GP, substrate to which the ebolavirus GP is attached, or ebolavirus GP in a biological specimen. It is, of course, recognized that a certain degree of non-specific interaction may occur between an antibody or conjugate including an antibody (such as an antibody that specifically binds ebolavirus GP or conjugate including such antibody) and a non-target (such as a cell that does not express ebolavirus GP). Typically, specific binding results in a much stronger association between the antibody and protein or cells bearing the antigen than between the antibody and protein or cells lacking the antigen. Specific binding typically results in greater than 2-fold, such as greater than 5-fold, greater than 10-fold, or greater than 100-fold increase in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein.

Subject: Living multicellular vertebrate organisms, a category that includes human and non-human mammals. In an example, a subject is a human. In an additional example, a subject is selected that is in need of inhibiting an ebolavirus infection. For example, the subject is uninfected and at risk of ebolavirus infection.

Transformed: A transformed cell is a cell into which a nucleic acid molecule has been introduced by molecular biology techniques. As used herein, the term transformed and the like (e.g., transformation, transfection, transduction, etc.) encompasses all techniques by which a nucleic acid molecule might be introduced into such a cell, including transduction with viral vectors, transformation with plasmid vectors, and introduction of DNA by electroporation, lipofection, and particle gun acceleration.

Vector: An entity containing a nucleic acid molecule (such as a DNA or RNA molecule) bearing a promoter(s) that is operationally linked to the coding sequence of a protein of interest and can express the coding sequence. Non-limiting examples include a naked or packaged (lipid and/or protein) DNA, a naked or packaged RNA, a subcomponent of a virus or bacterium or other microorganism that may be replication-incompetent, or a virus or bacterium or other microorganism that may be replication-competent. A vector is sometimes referred to as a construct. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant nucleic acid vectors having at least some nucleic acid sequences derived from one or more viruses. In some embodiments, a viral vector comprises a nucleic acid molecule encoding a disclosed antibody or antigen binding fragment that specifically binds to ebolavirus GP and neutralizes an ebolavirus. In some embodiments, the viral vector can be an adeno-associated virus (AAV) viral vector.

II. Description of Several Embodiments

A. Neutralizing Monoclonal Antibodies and Antigen Binding Fragments to Ebolavirus GP Isolated monoclonal antibodies and antigen binding fragments that specifically bind an epitope on ebolavirus GP are provided. The antibodies and antigen binding fragments can be fully human. The antibodies and antigen binding fragments can neutralize neutralizes an ebolavirus. Also disclosed herein are compositions including the antibodies and antigen binding fragments and a pharmaceutically acceptable carrier. Nucleic acids encoding the antibodies or antigen binding fragments, expression vectors (such as (AAV) viral vectors) including these nucleic acids are also provided. The antibodies, antigen binding fragments, nucleic acid molecules, host cells, and compositions can be used for research, diagnostic and prophylactic purposes. For example, the disclosed antibodies and antigen binding fragments can be used to diagnose a subject with an ebolavirus infection, or can be administered prophylactically to inhibit ebolavirus infection in a subject.

In several embodiments, the antibody or antigen binding fragment includes heavy and light chain variable regions including the HCDR1, HCDR2, and HCDR3, and LCDR1, LCDR2, and LCDR3, respectively, of the S1-4-A09 antibody, and specifically binds to ebolavirus GP and neutralizes ebolaviruses.

The discussion of monoclonal antibodies below refers to isolated monoclonal antibodies that include heavy and/or light chain variable domains (or antigen binding fragments thereof) including a CDR1, CDR2, and/or CDR3 with reference to the Kabat numbering scheme (unless the context indicates otherwise). Various CDR numbering schemes (such as the Kabat, Chothia or IMGT numbering schemes) can be used to determine CDR positions. The amino acid sequence and positions of the heavy and light chain CDRs of the S1-4-A09 antibody according to the IMGT numbering scheme are shown in Table 1.

TABLE 1

IMGT CDR sequences of ebolavirus GP-specific antibodies

A09 $V_H$

| $V_H$ | SEQ ID NO: 1 residues | A.A. Sequence | CDR SEQ ID NO |
|---|---|---|---|
| HCDR1 | 26-33 | GGILSSFY | 7 |
| HCDR2 | 51-57 | IYYSGSP | 8 |
| HCDR3 | 96-114 | VRASRAYLWGSYRPTALDL | 9 |

A09 $V_L$

| $V_L$ | SEQ ID NO: 2 residues | A.A. Sequence | CDR SEQ ID NO |
|---|---|---|---|
| LCDR1 | 26-31 | KLGDKY | 10 |
| LCDR2 | 49-51 | QDN | 11 |
| LCDR3 | 88-95 | QVWDSGAV | 12 |

In some embodiments, the antibody or antigen binding fragment can be based on or derived from the S1-4-A09 antibody, and specifically binds to ebolavirus GP and neutralizes an ebolavirus. For example, the antibody or antigen binding fragment comprises a $V_H$ and a $V_L$ comprising the HCDR1, the HCDR2, and the HCDR3, and the LCDR1, the LCDR2, and the LCDR3, respectively (for example, according to IMGT or Kabat), of the S1-4-A09 antibody, and specifically binds to ebolavirus GP and neutralizes an ebolavirus.

In some embodiments, the antibody or antigen binding fragment comprises a $V_H$ comprising the HCDR1, the HCDR2, and the HCDR3 of the S1-4-A09 $V_H$ as set forth in Table 1, and specifically binds to ebolavirus GP and neutralizes an ebolavirus. In some embodiments, the antibody or antigen binding fragment comprises a $V_L$ comprising the LCDR1, the LCDR2, and the LCDR3 of the S1-4-A09 $V_L$ as set forth in Table 1, and specifically binds to ebolavirus GP and neutralizes an ebolavirus. In some embodiments, the antibody or antigen binding fragment comprises a $V_H$ and a $V_L$ comprising the HCDR1, the HCDR2, the HCDR3, the LCDR1, the LCDR2, and the LCDR3 of the S1-4-A09 $V_H$ and $V_L$ as set forth in Table 1, and specifically binds to ebolavirus GP and neutralizes an ebolavirus.

In some embodiments, the antibody or antigen binding fragment includes a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-57, and 96-114, respectively, of SEQ ID NO: 1, and specifically binds to ebolavirus GP and neutralizes an ebolavirus. In some embodiments, the antibody or antigen binding fragment comprises a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-31, 49-51, and 88-95, respectively, of SEQ ID NO: 2, and specifically binds to ebolavirus GP and neutralizes an ebolavirus. In additional embodiments, the antibody or antigen binding fragment comprises a $V_H$ comprising a HCDR1, a HCDR2, and a HCDR3 comprising amino acid sequences at least 90% (such as at least 95%, at least 96%, at least 97%, at least 98%, or at least 99%) identical to amino acids 26-33, 51-57, and 96-114, respectively, of SEQ ID NO: 1, and a $V_L$ comprising a LCDR1, a LCDR2, and a LCDR3 comprising amino acid sequences at least 90% (such as at least 95%, at least 96%, at least 97%, at least 98%, or at least 99%) identical to amino acids amino acids 26-31, 49-51, and 88-95, respectively, of SEQ ID NO: 2, and specifically binds to ebolavirus GP and neutralizes an ebolavirus.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 1, and specifically binds to ebolavirus GP and neutralizes an ebolavirus. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 2, and specifically binds to ebolavirus GP and neutralizes an ebolavirus. In additional embodiments, the antibody or antigen binding fragment comprises a $V_H$ and a $V_L$ independently comprising amino acid sequences at least 90% (such as at least 95%, at least 96%, at least 97%, at least 98%, or at least 99%) identical to the amino acid sequences set forth as SEQ ID NOs: 1 and 2, respectively, and specifically binds to ebolavirus GP and neutralizes an ebolavirus.

The $V_H$ of the S1-4-A09 antibody contains an N-linked glycan sequon beginning at Kabat position 60. As disclosed herein, it is believed that removal of this N-linked glycan sequon leads to improved antibody characteristics, such as improved solubility, autoreactivity, and/or neutralization. Accordingly, in some embodiments, the $V_H$ of the antibody or antigen binding fragment provided herein does not comprise an N-linked glycan sequon beginning at Kabat position 60. In some embodiments, the $V_H$ of the antibody or antigen binding fragment provided herein does not comprise an N-linked glycan sequon beginning at any of Kabat positions 58-60. In some embodiments, the $V_H$ of the antibody or antigen binding fragment provided herein does not comprise an N-linked glycan sequon in the framework region 3 of the antibody. N-linked glycan sequons are defined by the sequence NX(S/T), where X is any amino acid except proline. Accordingly, removal of an N-linked glycan sequon at any of the positions noted above can be accomplished by appropriate amino acid substitution, for example, by substitution to replace the serine or threonine of the sequon with an amino acid that is not serine or threonine, or by substitution of a proline at the "X" position. In some embodiments, the N-linked glycan sequon beginning at Kabat position 60 of the $V_H$ of the S1-4-A09 antibody is removed by an A61P substitution.

In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 3, and does not contain an N-linked glycan sequon beginning at Kabat position 60 (for example by A61P substitution), and specifically binds to ebolavirus GP and neutralizes an ebolavirus. In more embodiments, the antibody or antigen binding fragment comprises a $V_L$ comprising an amino acid sequence at least 90% (such as at least 95%, at least 96%, at least 97%, at least 98%, or at least 99%) identical to the amino acid sequence set forth as SEQ ID NO: 2, and specifically binds to ebolavirus GP and neutralizes an ebolavirus. In some embodiments, the antibody or antigen binding fragment comprises a $V_H$ comprising an amino acid sequence at least 90% (such as at least 95%, at least 96%, at least 97%, at least 98%, or at least 99%) identical to the amino acid sequence set forth as SEQ ID NO: 3, does not contain an N-linked glycan sequon beginning at Kabat position 60 (for example by A61P substitution), comprises a $V_L$ comprising an amino acid sequence at least 90% (such as at least 95%, at least 96%, at least 97%, at least 98%, or at least 99%) identical to the amino acid sequence set forth as SEQ ID NO: 2, and specifically binds to ebolavirus GP and neutralizes an ebolavirus.

In additional embodiments, the antibody or antigen binding fragment comprises a $V_H$ comprising the amino acid sequence set forth as one of SEQ ID NO: 1 or SEQ ID NO: 3, and specifically binds to ebolavirus GP and neutralizes an ebolavirus. In more embodiments, the antibody or antigen binding fragment comprises a $V_L$ comprising the amino acid sequence set forth as SEQ ID NO: 2, and specifically binds to ebolavirus GP and neutralizes an ebolavirus. In some embodiments, the antibody or antigen binding fragment comprises a $V_H$ and a $V_L$ comprising the amino acid sequences set forth as SEQ ID NOs: 1 and 2, respectively, or SEQ ID NOs: 3 and 2, respectively, and specifically binds to ebolavirus GP and neutralizes an ebolavirus.

Additional Description of Antibodies and Antigen Binding Fragments

The antibody or antigen binding fragment can be a human antibody or fragment thereof. Chimeric antibodies are also provided. The antibody or antigen binding fragment can include any suitable framework region, such as (but not limited to) a human framework region. Human framework regions, and mutations that can be made in human antibody framework regions, are known in the art (see, for example, in U.S. Pat. No. 5,585,089, which is incorporated herein by reference). Alternatively, a heterologous framework region, such as, but not limited to a mouse or monkey framework region, can be included in the heavy or light chain of the antibodies. (See, for example, Jones et al., *Nature,* 321 (6069):522-525, 1986; Riechmann et al., *Nature,* 332(6162): 323-327, 1988; Verhoeyen et al., *Science* 239(4847):1534-1536, 1988; Carter et al., *Proc. Natl. Acad. Sci. U.S.A.* 89(10):4285-4289, 1992; Sandhu, *Crit. Rev. Biotechnol.* 12(5-6):437-462, 1992; and Singer et al., *J. Immunol.* 150 (7):2844-2857, 1993.)

The antibody can be of any isotype. The antibody can be, for example, an IgM or an IgG antibody, such as $IgG_1$, $IgG_2$, $IgG_3$, or $IgG_4$. The class of an antibody that specifically binds ebolavirus GP can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. A nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds ebolavirus GP, that was originally IgG may be class switched to an IgM. Class switching can be used to convert one IgG subclass to another, such as from $IgG_1$ to $IgG_2$, $IgG_3$, or $IgG_4$.

In some examples, the disclosed antibodies are oligomers of antibodies, such as dimers, trimers, tetramers, pentamers, hexamers, septamers, octomers and so on.

(a) Binding Affinity

In several embodiments, the antibody or antigen binding fragment specifically binds ebolavirus GP with an affinity (e.g., measured by $K_D$) of no more than $1.0 \times 10^{-8}$ M, no more than $5.0 \times 10^{-8}$ M, no more than $1.0 \times 10^{-9}$ M, no more than $5.0 \times 10^{-9}$ M, no more than $1.0 \times 10^{-10}$ M, no more than $5.0 \times 10^{-10}$ M, or no more than $1.0 \times 10^{-11}$ M. $K_D$ can be measured, for example, by a radiolabeled antigen binding assay (RIA) performed with the Fab version of an antibody of interest and its antigen using known methods. In one assay, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293(4):865-881, 1999). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc™ Catalog #269620), 100 µM or 26 µM [$^{125}$I]-antigen are mixed with serial dilutions of a Fab of interest (e.g., consistent with assessment of the anti-VEGF antibody, Fab-12, in Presta et al., *Cancer Res.* 57(20):4593-4599, 1997). The Fab of interest is then incubated overnight;

however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MicroScint™-20; PerkinEmler) is added, and the plates are counted on a TOPCOUNT™ gamma counter (PerkinEmler) for ten minutes. Concentrations of each Fab that give less than or equal to 20% of maximal binding are chosen for use in competitive binding assays.

(b) Multispecific Antibodies

In some embodiments, the antibody or antigen binding fragment is included on a multispecific antibody, such as a bi-specific antibody. Such multispecific antibodies can be produced by known methods, such as crosslinking two or more antibodies, antigen binding fragments (such as scFvs) of the same type or of different types. Exemplary methods of making multispecific antibodies include those described in PCT Pub. No. WO2013/163427, which is incorporated by reference herein in its entirety. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are commercially available, for example, from Thermo Fisher Scientific, Waltham, Mass., and MilliporeSigma Corporation, St. Louis, Mo.

Various types of multi-specific antibodies are known. Bispecific single chain antibodies can be encoded by a single nucleic acid molecule. Examples of bispecific single chain antibodies, as well as methods of constructing such antibodies are known in the art (see, e.g., U.S. Pat. Nos. 8,076,459, 8,017,748, 8,007,796, 7,919,089, 7,820,166, 7,635,472, 7,575,923, 7,435,549, 7,332,168, 7,323,440, 7,235,641, 7,229,760, 7,112,324, 6,723,538, incorporated by reference herein). Additional examples of bispecific single chain antibodies can be found in PCT application No. WO 99/54440; Mack et al., *J. Immunol.*, 158(8):3965-3970, 1997; Mack et al., *Proc. Natl. Acad. Sci. U.S.A.*, 92(15): 7021-7025, 1995; Kufer et al., *Cancer Immunol. Immunother.*, 45(3-4):193-197, 1997; Loffler et al., *Blood*, 95(6): 2098-2103, 2000; and Brühl et al., *J. Immunol.*, 166(4): 2420-2426, 2001. Production of bispecific Fab-scFv ("bibody") molecules are described, for example, in Schoonjans et al. (*J. Immunol.*, 165(12):7050-7057, 2000) and Willems et al. (*J. Chromatogr, B Analyt. Technol. Biomed Life Sci.* 786(1-2):161-176, 2003). For bibodies, a scFv molecule can be fused to one of the VL-CL (L) or VH-CH1 chains, e.g., to produce a bibody one scFv is fused to the C-term of a Fab chain.

(c) Fragments

Antigen binding fragments are encompassed by the present disclosure, such as Fab, F(ab')$_2$, and Fv which include a heavy chain and V$_L$ and specifically bind ebolavirus GP. These antibody fragments retain the ability to selectively bind with the antigen and are "antigen-binding" fragments. Non-limiting examples of such fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain;

(3) $(Fab')_2$, the fragment of the antibody that can be obtained by treating whole antibody with the enzyme pepsin without subsequent reduction; $F(ab')_2$ is a dimer of two Fab' fragments held together by two disulfide bonds;

(4) Fv, a genetically engineered fragment containing the $V_L$ and $V_L$ expressed as two chains; and (5) Single chain antibody (such as scFv), defined as a genetically engineered molecule containing the $V_H$ and the $V_L$ linked by a suitable polypeptide linker as a genetically fused single chain molecule (see, e.g., Ahmad et al., *Clin. Dev. Immunol.,* 2012, doi:10.1155/2012/980250; Marbry and Snavely, *IDrugs,* 13(8):543-549, 2010). The intramolecular orientation of the $V_H$-domain and the $V_L$-domain in a scFv, is not decisive for the provided antibodies (e.g., for the provided multi-specific antibodies). Thus, scFvs with both possible arrangements ($V_H$-domain-linker domain-$V_L$-domain; $V_L$-domain-linker domain-$V_H$-domain) may be used.

(6) A dimer of a single chain antibody ($scFV_2$), defined as a dimer of a scFV. This has also been termed a "miniantibody."

Methods of making these fragments are known in the art (see for example, Greenfield (Ed.), *Antibodies: A Laboratory Manual,* 2nd ed. New York: Cold Spring Harbor Laboratory Press, 2014).

In some embodiments, the antigen binding fragment can be an Fv antibody, which is typically about 25 kDa and contains a complete antigen-binding site with three CDRs per each heavy chain and each light chain. To produce $F_v$ antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the $V_H$ and the $V_L$ are chemically linked by disulfide bonds. In an additional example, the Fv fragments include $V_H$ and $V_L$ chains connected by a peptide linker. These single-chain antigen binding proteins (scFv) can be prepared by constructing a nucleic acid molecule encoding the $V_H$ and $V_L$ domains connected by an oligonucleotide. The nucleic acid molecule is inserted into an expression vector, which is subsequently introduced into a host cell such as a mammalian cell. The recombinant host cells synthesize a single polypeptide chain with a linker peptide bridging the two V domains. Methods for producing scFvs are known in the art (see Whitlow and Filpula, *Methods,* 2(2): 97-105, 1991; Bird et al., *Science,* 242 (4877):423-426, 1988; U.S. Pat. No. 4,946,778; Pack et al., *Biotechnology* (*N.Y.*), 11(11):1271-1277, 1993; Ahmad et al., *Clin. Dev. Immunol.,* 2012, doi:10.1155/2012/980250; Marbry and Snavely, *IDrugs,* 13(8):543-549, 2010). Dimers of a single chain antibody ($scFV_2$), are also contemplated.

Antigen binding fragments can be prepared by proteolytic hydrolysis of the antibody or by expression in a host cell (such as an *E. coli* cell) of DNA encoding the fragment. Antigen binding fragments can also be obtained by pepsin or papain digestion of whole antibodies by conventional methods. For example, antigen binding fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. In some examples, the antibody heavy chain can include an engineered protease cleave site (such as an HRV3C protease cleavage site) in place of or in addition to the typical papain cleavage site to facilitate cleavage by proteases other than papain.

Antigen binding single $V_H$ domains, called domain antibodies (dAb), have also been identified from a library of murine $V_H$ genes amplified from genomic DNA of immunized mice (Ward et al. *Nature,* 341(6242):544-546, 1989). Human single immunoglobulin variable domain polypeptides capable of binding antigen with high affinity have also been described (see, for example, PCT Publication Nos. WO 2005/035572 and WO 2003/002609). The CDRs disclosed herein can also be included in a dAb.

In some embodiments, one or more of the heavy and/or light chain complementarity determining regions (CDRs) from a disclosed antibody (such as the S1-4-A09 antibody) is expressed on the surface of another protein, such as a scaffold protein. The expression of domains of antibodies on the surface of a scaffolding protein are known in the art (see e.g., Liu et al., *J. Virology,* 85(17): 8467-8476, 2011). Such expression creates a chimeric protein that retains binding for ebolavirus GP. In some specific embodiments, one or more of the heavy chain CDRs is grafted onto a scaffold protein, such as one or more of heavy chain CDR1, CDR2, and/or CDR3. One or more CDRs can also be included in a diabody or another type of single chain antibody molecule.

(d) Variants

In some embodiments, amino acid sequence variants of the antibodies provided herein are provided. For example, it may be desirable to improve the binding affinity and/or other biological properties of the antibody Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

In some embodiments, antibody variants having one or more amino acid substitutions are provided. Sites of interest for substitutional mutagenesis include the CDRs and the framework regions Amino acid substitutions may be introduced into an antibody of interest and the products screened for a desired activity, e.g., retained/improved antigen binding, decreased immunogenicity, or improved antibody dependent cellular cytotoxicity (ADCC) or complement dependent cytotoxicity (CDC).

The variants typically retain amino acid residues necessary for correct folding and stabilizing between the $V_H$ and the $V_L$ regions, and will retain the charge characteristics of the residues in order to preserve the low pI and low toxicity of the molecules Amino acid substitutions can be made in the $V_H$ and the $V_L$ regions to increase yield.

In some embodiments, the $V_H$ of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as SEQ ID NOs: 1 or 3. In some embodiments, the $V_L$ of the antibody comprises up to 10 (such as up to 1, up to 2, up to 3, up to 4, up to 5, up to 6, up to 7, up to 8, or up to 9) amino acid substitutions (such as conservative amino acid substitutions) compared to the amino acid sequence set forth as SEQ ID NO: 2.

In some embodiments, the antibody or antigen binding fragment can include up to 10 (such as up to 1, up to 2, up to 3, up to 4, up to 5, up to 6, up to 7, up to 8, or up to 9) amino acid substitutions (such as conservative amino acid substitutions) in the framework regions of the heavy chain of the antibody, or the light chain of the antibody, or the heavy and light chains of the antibody compared to the framework regions of the S1-4-A09 antibody, and maintain the specific binding activity for ebolavirus GP.

In some embodiments, substitutions, insertions, or deletions may occur within one or more CDRs so long as such alterations do not substantially reduce the ability of the antibody to bind antigen. For example, conservative alterations (e.g., conservative substitutions as provided herein) that do not substantially reduce binding affinity may be made in CDRs. In some embodiments of the variant $V_H$ and $V_L$ sequences provided above, each CDR either is unaltered, or contains no more than one, no more than two, or no more than three amino acid substitutions.

To increase binding affinity of the antibody, the $V_L$ and $V_H$ segments can be randomly mutated, such as within the HCDR3 region or the LCDR3 region, in a process analogous to the in vivo somatic mutation process responsible for affinity maturation of antibodies during a natural immune response. Thus in vitro affinity maturation can be accomplished by amplifying $V_H$ and $V_L$ regions using PCR primers complementary to the HCDR3 or LCDR3, respectively. In this process, the primers have been "spiked" with a random mixture of the four nucleotide bases at certain positions such that the resultant PCR products encode $V_H$ and $V_L$ segments into which random mutations have been introduced in the $V_H$ and/or $V_L$ CDR3 regions. These randomly mutated $V_H$ and $V_L$ segments can be tested to determine the binding affinity for ebolavirus GP. In particular examples, the $V_H$ amino acid sequence is one of SEQ ID NOs: 1 or 3. In other examples, the $V_L$ amino acid sequence is SEQ ID NO: 2. Methods of in vitro affinity maturation are known (see, e.g., Chowdhury, *Methods Mol. Biol.,* 207:179-196, 2003, and Hoogenboom, *Methods Mol. Biol.,* 178:1-37, 2002.)

In some embodiments, an antibody or antigen binding fragment is altered to increase or decrease the extent to which the antibody or antigen binding fragment is glycosylated. Addition or deletion of glycosylation sites may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the $CH_2$ domain of the Fc region. See, e.g., Wright et al. *Trends Biotechnol.* 15(1):26-32, 1997. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region; however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO 2002/031140; Okazaki et al., J. Mol. Biol., 336(5):1239-1249, 2004; Yamane-Ohnuki et al., Biotechnol. Bioeng. 87(5):614-622, 2004. Examples of cell lines capable of producing defucosylated antibodies include Lec 13 CHO cells deficient in protein fucosylation (Ripka et al., Arch. Biochem. Biophys. 249(2):533-545, 1986; US Pat. Appl. No. US 2003/0157108 and WO 2004/056312, especially at Example 11), and knockout cell lines, such as alpha-1,6-fucosyltransferase gene, FUT8, knockout CHO cells (see, e.g., Yamane-Ohnuki et al., Biotechnol. Bioeng., 87(5): 614-622, 2004; Kanda et al., Biotechnol. Bioeng., 94(4): 680-688, 2006; and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087; WO 1998/58964; and WO 1999/22764.

In several embodiments, the constant region of the antibody comprises one or more amino acid substitutions to optimize in vivo half-life of the antibody. The serum half-life of IgG Abs is regulated by the neonatal Fc receptor (FcRn). Thus, in several embodiments, the antibody comprises an amino acid substitution that increases binding to the FcRn. Several such substitutions are known, such as substitutions at IgG constant regions T250Q and M428L (see, e.g., Hinton et al., J Immunol., 176(1):346-356, 2006); M428L and N434S (the "LS" mutation, see, e.g., Zalevsky, et al., Nature Biotechnol., 28(2):157-159, 2010); N434A (see, e.g., Petkova et al., Int. Immunol., 18(12):1759-1769, 2006); T307A, E380A, and N434A (see, e.g., Petkova et al., Int. Immunol., 18(12):1759-1769, 2006); and M252Y, S254T, and T256E (see, e.g., Dall'Acqua et al., J. Biol. Chem., 281(33):23514-23524, 2006). The disclosed antibodies and antigen binding fragments can be linked to or comprise a Fc polypeptide including any of the substitutions listed above, for example, the Fc polypeptide can include the M428L and N434S substitutions.

In some embodiments, the constant region of the antibody comprises one or more amino acid substitutions to optimize ADCC. ADCC is mediated primarily through a set of closely related Fcy receptors. In some embodiments, the antibody comprises one or more amino acid substitutions that increase binding to FcγRIIIa. Several such substitutions are known, such as substitutions at IgG constant regions S239D and I332E (see, e.g., Lazar et al., Proc. Natl., Acad. Sci. U.S.A., 103(11):4005-4010, 2006); and S239D, A330L, and I332E (see, e.g., Lazar et al., Proc. Natl., Acad. Sci. U.S.A., 103(11):4005-4010, 2006).

Combinations of the above substitutions are also included, to generate an IgG constant region with increased binding to FcRn and FcγRIIIa. The combinations increase antibody half-life and ADCC. For example, such combinations include antibodies with the following amino acid substitutions in the Fc region: (1) S239D/I332E and T250Q/M428L; (2) S239D/I332E and M428L/N434S; (3) S239D/I332E and N434A; (4) S239D/I332E and T307A/E380A/N434A; (5) S239D/I332E and M252Y/S254T/T256E; (6) S239D/A330L/I332E and 250Q/M428L; (7) S239D/A330L/I332E and M428L/N434S; (8) S239D/A330L/I332E and N434A; (9) S239D/A330L/I332E and T307A/E380A/N434A; or (10) S239D/A330L/I332E and M252Y/S254T/T256E. In some examples, the antibodies, or an antigen binding fragment thereof is modified such that it is directly cytotoxic to infected cells, or uses natural defenses such as complement, ADCC, or phagocytosis by macrophages.

In some embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in an application under defined conditions, etc.

The antibody or antigen binding fragment can be derivatized or linked to another molecule (such as another peptide or protein). In general, the antibody or antigen binding fragment is derivatized such that the binding to ebolavirus GP is not affected adversely by the derivatization or labeling. For example, the antibody or antigen binding fragment can be functionally linked (by chemical coupling, genetic fusion, noncovalent association or otherwise) to one or more other molecular entities, such as another antibody (for example, a bi-specific antibody or a diabody), a detectable marker, an effector molecule, or a protein or peptide that can mediate association of the antibody or antibody portion with another molecule (such as a streptavidin core region or a polyhistidine tag).

B. Conjugates

The antibodies and antigen binding fragments that specifically bind to ebolavirus GP can be conjugated to an agent, such as an effector molecule or detectable marker. Both covalent and noncovalent attachment means may be used. Various effector molecules and detectable markers can be conjugated to the antibody or antigen binding fragment, including (but not limited to) toxins and radioactive agents such as $^{125}$I, $^{32}$P, $^{14}$C, $^{3}$H and $^{35}$S and other labels, target moieties and ligands, etc. The choice of a particular effector molecule or detectable marker depends on the particular target molecule or cell, and the desired biological effect.

The procedure for attaching an effector molecule or detectable marker to an antibody or antigen binding fragment varies according to the chemical structure of the effector. Polypeptides typically contain a variety of functional groups, such as carboxyl (—COOH), free amine (—NH$_2$) or sulfhydryl (—SH) groups, which are available for reaction with a suitable functional group on a polypeptide to result in the binding of the effector molecule or detectable marker. Alternatively, the antibody or antigen binding fragment is derivatized to expose or attach additional reactive functional groups. The derivatization may involve attachment of any of a number of known linker molecules, such as those available from Thermo Fisher Scientific, Waltham, Mass. and MilliporeSigma Corporation, St. Louis, Mo. The linker is capable of forming covalent bonds to both the antibody or antigen binding fragment and to the effector molecule or detectable marker. Suitable linkers include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side chains (such as through a disulfide linkage to cysteine) or the alpha carbon, or through the amino, and/or carboxyl groups of the terminal amino acids.

In view of the large number of methods that have been reported for attaching a variety of radiodiagnostic compounds, radiotherapeutic compounds, labels (such as enzymes or fluorescent molecules), toxins, and other agents to antibodies, a suitable method for attaching a given agent to an antibody or antigen binding fragment or other polypeptide can be determined.

In some embodiments, the antibody or antigen binding fragment can be conjugated with effector molecules such as small molecular weight drugs such as Monomethyl Auristatin E (MMAE), Monomethyl Auristatin F (MMAF), maytansine, maytansine derivatives, including the derivative of maytansine known as DM1 (also known as mertansine), or other agents to make an antibody drug conjugate (ADC). In several embodiments, conjugates of an antibody or antigen binding fragment and one or more small molecule toxins, such as a calicheamicin, maytansinoids, dolastatins, auristatins, a trichothecene, and CC1065, and the derivatives of these toxins that have toxin activity, are provided.

The antibody or antigen binding fragment can be conjugated with a detectable marker; for example, a detectable marker capable of detection by ELISA, spectrophotometry, flow cytometry, microscopy or diagnostic imaging techniques (such as CT, computed axial tomography (CAT), MRI, magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP), and yellow fluorescent protein (YFP). An antibody or antigen binding fragment can also be conjugated with enzymes that are useful for detection, such as horseradish peroxidase, β-galactosidase, luciferase, alkaline phosphatase, glucose oxidase and the like. When an antibody or antigen binding fragment is conjugated with a detectable enzyme, it can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. An antibody or antigen binding fragment may also be conjugated with biotin, and detected through indirect measurement of avidin or streptavidin binding. It should be noted that the avidin itself can be conjugated with an enzyme or a fluorescent label.

The antibody or antigen binding fragment can be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitope recognized by a secondary reporter (such as leucine zipper pair sequences, binding sites for secondary antibodies, metal binding domains, epitope tags).

The antibody or antigen binding fragment can be conjugated with a radiolabeled amino acid, for example, for diagnostic purposes. For instance, the radiolabel may be used to detect ebolavirus GP expressing cells by radiography, emission spectra, or other diagnostic techniques. Examples of labels for polypeptides include, but are not limited to, the following radioisotopes: $^{3}$H, $^{14}$C, $^{35}$S, $^{90}$Y, $^{99m}$Tc, $^{111}$In, $^{125}$I, $^{131}$I. The radiolabels may be detected, for example, using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

The average number of effector molecule or detectable marker moieties per antibody or antigen binding fragment in a conjugate can range, for example, from 1 to 20 moieties per antibody or antigen binding fragment. In some embodiments, the average number of effector molecules or detectable marker moieties per antibody or antigen binding fragment in a conjugate range from about 1 to about 2, from about 1 to about 3, about 1 to about 8; from about 2 to about 6; from about 3 to about 5; or from about 3 to about 4. The loading (for example, effector molecule per antibody ratio) of a conjugate may be controlled in different ways, for example, by: (i) limiting the molar excess of effector molecule-linker intermediate or linker reagent relative to antibody, (ii) limiting the conjugation reaction time or temperature, (iii) partial or limiting reducing conditions for cysteine thiol modification, (iv) engineering by recombinant techniques the amino acid sequence of the antibody such that the number and position of cysteine residues is modified for control of the number or position of linker-effector molecule attachments.

C. Polynucleotides and Expression

Nucleic acid molecules (for example, cDNA or RNA molecules) encoding the amino acid sequences of antibodies, antigen binding fragments, and conjugates that specifically bind to ebolavirus GP are provided. Nucleic acids encoding these molecules can readily be produced using the amino acid sequences provided herein (such as the CDR sequences and $V_H$ and $V_L$ sequences), sequences available in the art (such as framework or constant region sequences), and the genetic code. In several embodiments, nucleic acid molecules can encode the $V_H$, the $V_L$, or both the $V_H$ and $V_L$ (for example in a bicistronic expression vector) of a disclosed antibody or antigen binding fragment. In several embodiments, the nucleic acid molecules can be expressed in a host cell (such as a mammalian cell) to produce a disclosed antibody or antigen binding fragment.

The genetic code can be used to construct a variety of functionally equivalent nucleic acid sequences, such as nucleic acids which differ in sequence but which encode the same antibody sequence or a conjugate or fusion protein including the $V_L$ and/or $V_H$ of the antibody.

In a non-limiting example, an isolated nucleic acid molecule encodes the $V_H$ of a disclosed antibody or antigen binding fragment and comprises the nucleic acid sequence set forth as SEQ ID NO: 13 or 15. In a non-limiting example, an isolated nucleic acid molecule encodes the $V_L$ of a disclosed antibody or antigen binding fragment and comprises the nucleic acid sequence set forth as SEQ ID NO: 14. In a non-limiting example, an isolated nucleic acid molecule encodes the $V_H$ and $V_L$ of a disclosed antibody or antigen binding fragment and comprises the nucleic acid sequences set forth as any one of SEQ ID NOs: 13 and 14, respectively, or 15 and 14, respectively.

Nucleic acid molecules encoding the antibodies, antigen binding fragments, and conjugates that specifically bind to ebolavirus GP can be prepared by any suitable method including, for example, cloning of appropriate sequences or by direct chemical synthesis by standard methods. Chemical synthesis produces a single stranded oligonucleotide. This can be converted into double stranded DNA by hybridization with a complementary sequence or by polymerization with a DNA polymerase using the single strand as a template.

Exemplary nucleic acids can be prepared by cloning techniques. Examples of appropriate cloning and sequencing techniques can be found, for example, in Green and Sambrook (*Molecular Cloning: A Laboratory Manual*, 4$^{th}$ ed., New York: Cold Spring Harbor Laboratory Press, 2012) and Ausubel et al. (Eds.) (*Current Protocols in Molecular Biology*, New York: John Wiley and Sons, including supplements, 2017).

Nucleic acids can also be prepared by amplification methods. Amplification methods include the polymerase chain reaction (PCR), the ligase chain reaction (LCR), the transcription-based amplification system (TAS), and the self-sustained sequence replication system (3SR).

The nucleic acid molecules can be expressed in a recombinantly engineered cell such as bacteria, plant, yeast, insect and mammalian cells. The antibodies, antigen binding fragments, and conjugates can be expressed as individual proteins including the $V_H$ and/or $V_L$ (linked to an effector molecule or detectable marker as needed), or can be expressed as a fusion protein. Methods of expressing and purifying antibodies and antigen binding fragments are known and further described herein (see, e.g., Al-Rubeai (Ed.), *Antibody Expression and Production*, Dordrecht; New York: Springer, 2011). An immunoadhesin can also be expressed. Thus, in some examples, nucleic acids encoding a $V_H$ and $V_L$, and immunoadhesin are provided. The nucleic acid sequences can optionally encode a leader sequence.

To create a scFv the $V_H$- and $V_L$-encoding DNA fragments can be operatively linked to another fragment encoding a flexible linker, e.g., encoding the amino acid sequence $(Gly_4\text{-Ser})_3$, such that the $V_H$ and $V_L$ sequences can be expressed as a contiguous single-chain protein, with the $V_L$ and $V_H$ domains joined by the flexible linker (see, e.g., Bird et al., *Science*, 242(4877):423-426, 1988; Huston et al., *Proc. Natl. Acad. Sci. U.S.A.*, 85(16):5879-5883, 1988; McCafferty et al., *Nature*, 348:552-554, 1990; Kontermann and Dübel (Eds.), *Antibody Engineering*, Vols. 1-2, 2$^{nd}$ ed., Springer-Verlag, 2010; Greenfield (Ed.), *Antibodies: A Laboratory Manual*, 2$^{nd}$ ed. New York: Cold Spring Harbor Laboratory Press, 2014). Optionally, a cleavage site can be included in a linker, such as a furin cleavage site.

The single chain antibody may be monovalent, if only a single $V_H$ and $V_L$ are used, bivalent, if two $V_H$ and $V_L$ are used, or polyvalent, if more than two $V_H$ and $V_L$ are used. Bispecific or polyvalent antibodies may be generated that bind specifically to ebolavirus GP and another antigen. The encoded $V_H$ and $V_L$ optionally can include a furin cleavage site between the $V_H$ and $V_L$ domains.

One or more DNA sequences encoding the antibodies, antigen binding fragments, or conjugates can be expressed in vitro by DNA transfer into a suitable host cell. The cell may be prokaryotic or eukaryotic. Numerous expression systems available for expression of proteins including *E. coli*, other bacterial hosts, yeast, and various higher eukaryotic cells such as the COS, CHO, HeLa and myeloma cell lines, can be used to express the disclosed antibodies and antigen binding fragments. Methods of stable transfer, meaning that the foreign DNA is continuously maintained in the host, are known in the art. Hybridomas expressing the antibodies of interest are also encompassed by this disclosure.

The expression of nucleic acids encoding the antibodies and antigen binding fragments described herein can be achieved by operably linking the DNA or cDNA to a promoter (which is either constitutive or inducible), followed by incorporation into an expression cassette. The promoter can be any promoter of interest, including a cytomegalovirus promoter. Optionally, an enhancer, such as a cytomegalovirus enhancer, is included in the construct. The cassettes can be suitable for replication and integration in either prokaryotes or eukaryotes. Typical expression cassettes contain specific sequences useful for regulation of the expression of the DNA encoding the protein. For example, the expression cassettes can include appropriate promoters, enhancers, transcription and translation terminators, initiation sequences, a start codon (i.e., ATG) in front of a protein-encoding gene, splicing signals for introns, sequences for the maintenance of the correct reading frame of that gene to permit proper translation of mRNA, and stop codons. The vector can encode a selectable marker, such as a marker encoding drug resistance (for example, ampicillin or tetracycline resistance).

To obtain high level expression of a cloned gene, it is desirable to construct expression cassettes which contain, for example, a strong promoter to direct transcription, a ribosome binding site for translational initiation (e.g., internal ribosomal binding sequences), and a transcription/translation terminator. For *E. coli*, this can include a promoter such as the T7, tip, lac, or lambda promoters, a ribosome binding site, and preferably a transcription termination signal. For eukaryotic cells, the control sequences can include a promoter and/or an enhancer derived from, for example, an immunoglobulin gene, HTLV, SV40 or cytomegalovirus, and a polyadenylation sequence, and can further include splice donor and/or acceptor sequences (for example, CMV and/or HTLV splice acceptor and donor sequences). The cassettes can be transferred into the chosen host cell by well-known methods such as transformation or electroporation for *E. coli* and calcium phosphate treatment, electroporation or lipofection for mammalian cells. Cells transformed by the cassettes can be selected by resistance to antibiotics conferred by genes contained in the cassettes, such as the amp, GPt, neo, and hyg genes.

Modifications can be made to a nucleic acid encoding a polypeptide described herein without diminishing its biological activity. Some modifications can be made to facilitate the cloning, expression, or incorporation of the targeting molecule into a fusion protein. Such modifications include, for example, termination codons, sequences to create conveniently located restriction sites, and sequences to add a methionine at the amino terminus to provide an initiation site, or additional amino acids (such as poly His) to aid in purification steps.

Once expressed, the antibodies, antigen binding fragments, and conjugates can be purified according to standard procedures in the art, including ammonium sulfate precipitation, affinity columns, column chromatography, and the like (see, generally, Simpson et al. (Eds.), *Basic methods in Protein Purification and Analysis: A Laboratory Manual*, New York: Cold Spring Harbor Laboratory Press, 2009). The antibodies, antigen binding fragment, and conjugates need not be 100% pure. Once purified, partially or to homogeneity as desired, if to be used prophylatically, the polypeptides should be substantially free of endotoxin.

Methods for expression of antibodies, antigen binding fragments, and conjugates, and/or refolding to an appropriate active form, from mammalian cells, and bacteria such as *E. coli* have been described and are applicable to the antibodies disclosed herein. See, e.g., Greenfield (Ed.), *Antibodies: A Laboratory Manual*, 2$^{nd}$ ed. New York: Cold Spring Harbor Laboratory Press, 2014, Simpson et al. (Eds.), *Basic methods in Protein Purification and Analysis: A Laboratory Manual*, New York: Cold Spring Harbor Laboratory Press, 2009, and Ward et al., *Nature* 341(6242): 544-546, 1989.

D. Methods and Compositions

1. Inhibiting Ebolavirus Infection

Methods are disclosed herein for the inhibition of an ebolavirus infection (such as *Zaire ebolavirus* infection). The methods include administering to a subject an effective amount (that is, an amount effective to inhibit ebolavirus infection in a subject) of a disclosed antibody, antigen binding fragment, conjugate, or a nucleic acid encoding such an antibody, antigen binding fragment, or conjugate, to a subject at risk of ebolavirus infection (such as *Zaire ebolavirus* infection). The methods can be used pre-exposure or post-exposure.

The disclosed antibodies can be administered to the subject alone, or in combination with other antibodies that target ebolavirus antigens, such as GP, to inhibit ebolavirus infection in the subject. In some embodiments, a disclosed antibody (such as the S1-4-A09 or S1-4-A09-A61P antibody) is administered to the subject in combination with the mAb114 antibody to inhibit ebolavirus infection (such as *Zaire ebolavirus* infection) in the subject.

The ebolavirus infection does not need to be completely eliminated or inhibited for the method to be effective. For example, the method can decrease the ebolavirus infection by a desired amount, for example by at least 10%, at least 20%, at least 50%, at least 60%, at least 70%, at least 80%, at least 90%, at least 95%, at least 98%, or even at least 100% (elimination or prevention of detectable ebolavirus infection) as compared to ebolavirus infection in the absence of the treatment.

In some embodiments, administration of an effective amount of a disclosed antibody, antigen binding fragment, conjugate, or nucleic acid molecule, inhibits the establishment of ebolavirus infection and/or subsequent EVD progression in a subject, which can encompass any statistically significant reduction in ebolavirus activity or symptoms of ebolavirus infection in the subject.

Antibodies and antigen binding fragments thereof are typically administered by intravenous infusion. Doses of the antibody or antigen binding fragment vary, but generally range between about 0.5 mg/kg to about 50 mg/kg, such as a dose of about 1 mg/kg, about 5 mg/kg, about 10 mg/kg, about 20 mg/kg, about 30 mg/kg, about 40 mg/kg, or about 50 mg/kg. In some embodiments, the dose of the antibody or antigen binding fragment can be from about 0.5 mg/kg to about 5 mg/kg, such as a dose of about 1 mg/kg, about 2 mg/kg, about 3 mg/kg, about 4 mg/kg or about 5 mg/kg. The antibody or antigen binding fragment is administered according to a dosing schedule determined by a medical practitioner. In some examples, the antibody or antigen binding fragment is administered weekly, every two weeks, every three weeks or every four weeks.

In some examples, a subject is administered DNA or RNA encoding a disclosed antibody to provide in vivo antibody production, for example using the cellular machinery of the subject. Administration of nucleic acid constructs is known in the art and taught, for example, in U.S. Pat. Nos. 5,643,578, 5,593,972 and 5,817,637. U.S. Pat. No. 5,880,103 describes several methods of delivery of nucleic acids encoding proteins to an organism. One approach to administration of nucleic acids is direct administration with plasmid DNA, such as with a mammalian expression plasmid. The nucleotide sequence encoding the disclosed antibody, or antigen binding fragments thereof, can be placed under the control of a promoter to increase expression. The methods include liposomal delivery of the nucleic acids. Such methods can be applied to the production of an antibody, or antigen binding fragments thereof. In some embodiments, a disclosed antibody or antigen binding fragment is expressed in a subject using the pVRC8400 vector (described in Barouch et al., *J. Virol.*, 79(14), 8828-8834, 2005, which is incorporated by reference herein).

In some embodiments, a subject (such as a human subject at risk of ebolavirus infection) can be administered an effective amount of a viral vector comprising a nucleic acid molecule encoding a disclosed antibody or antigen binding fragment. A number of viral vectors are available that can be used to express the disclosed antibodies or antigen binding fragments, such as a retroviral vector, an adenoviral vector, or an AAV viral vector. In several examples, the viral vector can be replication-competent. For example, the viral vector can have a mutation in the viral genome that does not inhibit viral replication in host cells. The viral vector also can be conditionally replication-competent. In other examples, the viral vector is replication-deficient in host cells.

In several embodiments, a subject (such as a human subject at risk of ebolavirus infection) can be administered an effective amount of an AAV viral vector that includes one or more nucleic acid molecules encoding a disclosed antibody or antigen binding fragment. The AAV viral vector is designed for expression of the nucleic acid molecules encoding a disclosed antibody or antigen binding fragment, and administration of the effective amount of the AAV viral vector to the subject leads to expression of an effective amount of the antibody or antigen binding fragment in the subject. Non-limiting examples of AAV viral vectors that can be used to express a disclosed antibody or antigen binding fragment in a subject include those provided in Johnson et al., *Nat. Med.,* 15(8):901-906, 2009 and Gardner et al., *Nature,* 519(7541):87-91, 2015, each of which is incorporated by reference herein in its entirety.

In one embodiment, a nucleic acid encoding a disclosed antibody, or antigen binding fragment thereof, is introduced directly into tissue. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter.

Typically, the DNA is injected into muscle, although it can also be injected directly into other sites. Dosages for injection are usually around 0.5 µg/kg to about 50 mg/kg, and typically are about 0.005 mg/kg to about 5 mg/kg (see, e.g., U.S. Pat. No. 5,589,466).

Single or multiple administrations of a composition including a disclosed ebolavirus GP-specific antibody, antigen binding fragment, conjugate, or nucleic acid molecule encoding such molecules, can be administered depending on the dosage and frequency as required and tolerated by the patient. The dosage can be administered once, but may be applied periodically until either a desired result is achieved or until side effects warrant discontinuation of therapy. Generally, the dose is sufficient to inhibit ebolavirus infection without producing unacceptable toxicity to the patient.

Data obtained from cell culture assays and animal studies can be used to formulate a range of dosage for use in humans. The dosage normally lies within a range of circulating concentrations that include the $ED_{50}$, with little or minimal toxicity. The dosage can vary within this range depending upon the dosage form employed and the route of administration utilized. The effective dose can be determined from cell culture assays and animal studies.

The ebolavirus GP-specific antibody, antigen binding fragment, conjugate, or nucleic acid molecule encoding such molecules, or a composition including such molecules, can be administered to subjects in various ways, including local and systemic administration, such as, e.g., by injection subcutaneously, intravenously, intra-arterially, intraperitoneally, intramuscularly, intradermally, or intrathecally. In an embodiment, the antibody, antigen binding fragment, conjugate, or nucleic acid molecule encoding such molecules, or a composition including such molecules, is administered by a single subcutaneous, intravenous, intra-arterial, intraperitoneal, intramuscular, intradermal or intrathecal injection once a day. The antibody, antigen binding fragment, conjugate, or nucleic acid molecule encoding such molecules, or a composition including such molecules, can also be administered by direct injection at or near the site of disease. A further method of administration is by osmotic pump (e.g., an Alzet pump) or mini-pump (e.g., an Alzet mini-osmotic pump), which allows for controlled, continuous and/or slow-release delivery of the antibody, antigen binding fragment, conjugate, or nucleic acid molecule encoding such molecules, or a composition including such molecules, over a pre-determined period. The osmotic pump or mini-pump can be implanted subcutaneously, or near a target site.

2. Compositions

Compositions are provided that include one or more of the ebolavirus GP-specific antibody, antigen binding fragment, conjugate, or nucleic acid molecule encoding such molecules, that are disclosed herein in a carrier. The compositions are useful, for example, for the inhibition or detection of an ebolavirus infection. The compositions can be prepared in unit dosage forms for administration to a subject. The amount and timing of administration are at the discretion of the administering physician to achieve the desired purposes. The ebolavirus GP-specific antibody, antigen binding fragment, conjugate, or nucleic acid molecule encoding such molecules can be formulated for systemic or local administration. In one example, the ebolavirus GP-specific antibody, antigen binding fragment, conjugate, or nucleic acid molecule encoding such molecules, is formulated for parenteral administration, such as intravenous administration.

In some embodiments, the antibody, antigen binding fragment, or conjugate thereof, in the composition is at least 70% (such as at least 75%, at least 80%, at least 85%, at least 90%, at least 95%, at least 96%, at least 97%, at least 98% or at least 99%) pure. In some embodiments, the composition contains less than 10% (such as less than 5%, less than 4%, less than 3%, less than 2%, less than 1%, less than 0.5%, or even less) of macromolecular contaminants, such as other mammalian (e.g., human) proteins.

The compositions for administration can include a solution of the ebolavirus GP-specific antibody, antigen binding fragment, conjugate, or nucleic acid molecule encoding such molecules, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well-known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical composition for intravenous administration includes about 0.01 to about 30 mg/kg of antibody or antigen binding fragment or conjugate per subject per day (or the corresponding dose of a conjugate including the antibody or antigen binding fragment). Actual methods for preparing administrable compositions are known and are described in more detail in such publications as *Remington: The Science and Practice of Pharmacy,* 22$^{nd}$ ed., London, UK: Pharmaceutical Press, 2013. In some embodiments, the composition can be a liquid formulation including one or more antibodies, antigen binding fragments (such as an antibody or antigen binding fragment that specifically binds to ebolavirus GP), in a concentration range from about 0.1 mg/ml to about 20 mg/ml, or from about 0.5 mg/ml to about 20 mg/ml, or from about 1 mg/ml to about 20 mg/ml, or from about 0.1 mg/ml to about 10 mg/ml, or from about 0.5 mg/ml to about 10 mg/ml, or from about 1 mg/ml to about 10 mg/ml.

Antibodies, or an antigen binding fragment thereof or a conjugate or a nucleic acid encoding such molecules, can be provided in lyophilized form and rehydrated with sterile water before administration, although they are also provided in sterile solutions of known concentration. The antibody solution, or an antigen binding fragment or a nucleic acid encoding such antibodies or antigen binding fragments, can then be added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of Rituximab in 1997. Antibodies, antigen binding fragments, conjugates, or a nucleic acid encoding such molecules, can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30-minute period if the previous dose was well tolerated.

Controlled-release parenteral formulations can be made as implants, oily injections, or as particulate systems. For a broad overview of protein delivery systems see, Banga, *Therapeutic Peptides and Proteins: Formulation, Processing, and Delivery Systems*, Lancaster, PA: Technomic Publishing Company, Inc., 1995. Particulate systems include microspheres, microparticles, microcapsules, nanocapsules, nanospheres, and nanoparticles. Microcapsules contain the active protein agent, such as a cytotoxin or a drug, as a central core. In microspheres, the active protein agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly. See, for example, Kreuter, *Colloidal Drug Delivery Systems*, J. Kreuter (Ed.), New York, NY: Marcel Dekker, Inc., pp. 219-342, 1994; and Tice and Tabibi, *Treatise on Controlled Drug Delivery: Fundamentals, Optimization, Applications*, A. Kydonieus (Ed.), New York, NY: Marcel Dekker, Inc., pp. 315-339, 1992.

Polymers can be used for ion-controlled release of the antibody compositions disclosed herein. Various degradable and nondegradable polymeric matrices for use in controlled drug delivery are known in the art (Langer, *Acc. Chem. Res.* 26(10):537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.*, 9(3):425-434, 1992; and Pec et al., *J. Parent. Sci. Tech.*, 44(2):58-65, 1990). Alternatively, hydroxyapatite has been used as a microcarrier for controlled release of proteins (Ijntema et al., *Int. J. Pharm.* 112(3):215-224, 1994). In yet another aspect, liposomes are used for controlled release as well as drug targeting of the lipid-capsulated drug (Betageri et al., *Liposome Drug Delivery Systems*, Lancaster, PA: Technomic Publishing Co., Inc., 1993). Numerous additional systems for controlled delivery of active protein agent are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

3. Methods of Detection and Diagnosis

Methods are also provided for the detection of the presence of ebolavirus GP in vitro or in vivo. In one example, the presence of ebolavirus GP is detected in a biological sample from a subject, and can be used to identify a subject with ebolavirus infection. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. The method of detection can include contacting a cell or sample, with an antibody or antigen binding fragment that specifically binds to ebolavirus GP, or conjugate thereof (e.g. a conjugate including a detectable marker) under conditions sufficient to form an immune complex, and detecting the immune complex (e.g., by detecting a detectable marker conjugated to the antibody or antigen binding fragment).

In one embodiment, the antibody or antigen binding fragment is directly labeled with a detectable marker. In another embodiment, the antibody that binds ebolavirus GP (the primary antibody) is unlabeled and a secondary antibody or other molecule that can bind the primary antibody is utilized for detection. The secondary antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially. Suitable labels for the antibody, antigen binding fragment or secondary antibody are known and described above, and include various enzymes, prosthetic groups, fluorescent materials, luminescent materials, magnetic agents and radioactive materials.

In some embodiments, the disclosed antibodies or antigen binding fragments thereof are used to test vaccines. For example, to test if a vaccine composition including an ebolavirus GP or fragment thereof assumes a conformation including the epitope of a disclosed antibody. Thus, provided herein is a method for testing a vaccine, wherein the method includes contacting a sample containing the vaccine, such as an ebolavirus-GP immunogen, with a disclosed antibody or antigen binding fragment under conditions sufficient for formation of an immune complex, and detecting the immune complex, to detect the vaccine, such as an ebolavirus-GP immunogen including the epitope, in the sample. In one example, the detection of the immune complex in the sample indicates that the vaccine component, such as an ebolavirus-GP immunogen, assumes a conformation capable of binding the antibody or antigen binding fragment.

III. EXAMPLES

The following example is provided to illustrate particular features of certain embodiments, but the scope of the claims should not be limited to those features exemplified.

Example 1

*Ebolavirus* GP-Specific Monoclonal Antibodies

This example illustrates the identification and characterization of the S1-4-A09 antibody, which specifically binds to *Zaire ebolavirus* GP and can neutralize *Zaire ebolavirus*.

Isolation and Sequence of S1-4-A09

S1-4-A09 is a mAb whose variable domain was isolated through nested PCR of the heavy and light chain immunoglobulin genes from GP-probe+, single-cell-sorted B-cells from a human EVD survivor. Due to the experimental method of sequence isolation, the original IgG subclass of S1-4-A09 is unknown. For this example, nucleic acids encoding the S1-4-A09 heavy and light chain variable regions were cloned into a standard construct used for antibody expression that is IgG1 based. The nucleotide sequences for the heavy and light chains of the expressed version of S1-4-A09 are provided as SEQ ID NOs: 16 and 17, respectively. The amino acid sequences of the $V_H$ and $V_L$ regions of the S1-4-A09 antibody are provided as SEQ ID NOs: 1 and 2, respectively, and are shown in FIG. 1. Gene family identification of the heavy and light chain variable domains is as follows:

|  | V-gene Family | D-gene Family | J-gene Family |
| --- | --- | --- | --- |
| Heavy Chain | IGHV4-59*01 | IGHD3-16*02 | IGHJ4*02 |
| Light Chain | IGLV3-1*01 |  | IGLJ2*01 |

Analysis of the S1-4-A09 heavy and light chain variable domain sequences and comparison with the corresponding sequences of mAb100 revealed several differences that are believed to contribute to improved manufacturability properties of S1-4-A09 as compared to those of mAb100 (FIG. 1). For example, there are differences in the HCDR1, HCDR3, LCDR1, and LCDR3 of these two antibodies. Additionally, an N-linked glycan sequon found at Kabat position 58 of the mAb100 $V_H$ ( . . . $N_{58}YS$ . . . ) is not present in the S1-4-A09 $V_H$. Instead, the S1-4-A09 $V_H$ contains an N-linked glycan sequon beginning at Kabat position 60 ( . . . N60AS . . . ). The shift of the glycan sequon to position 60 places this glycan farther from the HCDR2 which may improve target binding. Further, a free cysteine found at Kabat position 34 of the mAb100 VL ( . . . $VC_{34}W$ . . . ) is not present in the S1-4-A09 $V_L$. Instead, the corresponding sequence of the S1-4-A09 VL ( . . . $TS_{34}W$ . . . ) contains a serine in place of the cysteine. The absence of the cysteine may improve manufacturability (such as solubility, stability, and purification) of the S1-4-A09 antibody.

Molecular and Functional Characterization

Several assays were used to determine mAb in vitro functionality, including reactivity with the *Zaire ebolavirus* surface glycoprotein GP. The mAbs were tested for binding to *Zaire ebolavirus* GP and mucin-domain-deleted *Zaire ebolavirus* GP by antigen-capture ELISA and by biolayer interferometry (BLI), and for inhibition of infection by single-round infection assays in cultured cells (293T). The mAbs were further tested for inhibition of *Zaire ebolavirus* GP cleavage by the protease thermolysin, which mimics cleavage by Cathepsin L, an event necessary for viral entry. mAbs were also evaluated for potential autoreactivity and manufacturability.

ELISA Binding to *Zaire ebolavirus* GP

Figure 2:
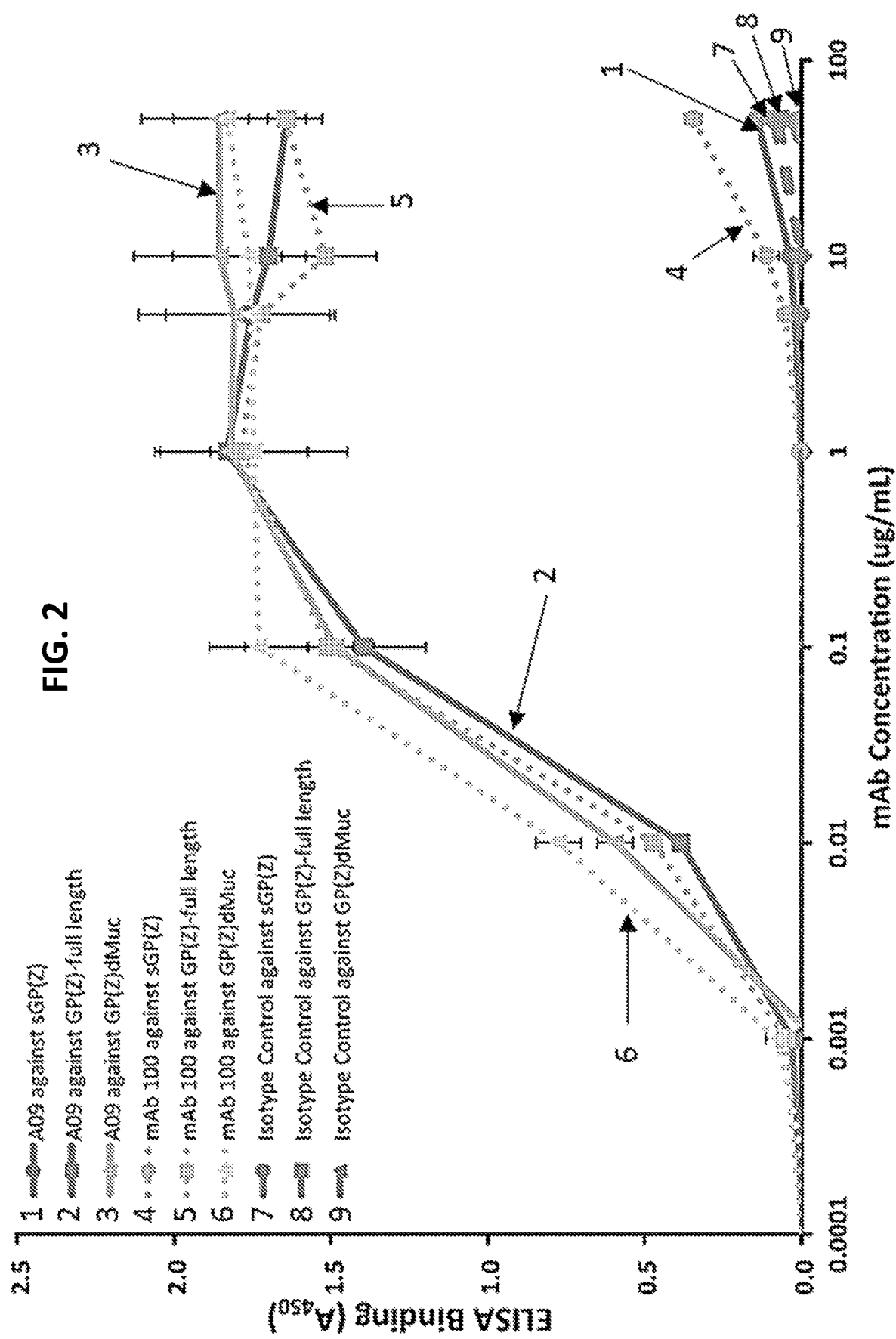
FIG. 2. Binding of S1-4-A09 to *Zaire ebolavirus* GP as assayed by enzyme-linked immunosorbent assay (ELISA). Shown are binding curves generated from S1-4-A09, mAb100 and an isotype control antibody binding to either Zaire ebolavirus sGP (sGP(Z)), full length GP (GP(Z)-full length) or mucin-domain-deleted GP (GP(Z)dMuc). Error bars shown represent the standard error of the mean of triplicate wells for each dilution point.

ELISA assays were performed using plates coated with bicarbonate buffer containing purified protein expressed from Expi293 cells (Invitrogen). Three forms of *Zaire ebolavirus* GP were evaluated: full-length GP, mucin-domain-deleted GP, and sGP. S1-4-A09 binding was evaluated in comparison to mAb100 and an isotype control. S1-4-A09 shows binding to all forms of GP evaluated similar to that of mAb100 (FIG. 2).

In Vitro Neutralization

Figure 3:
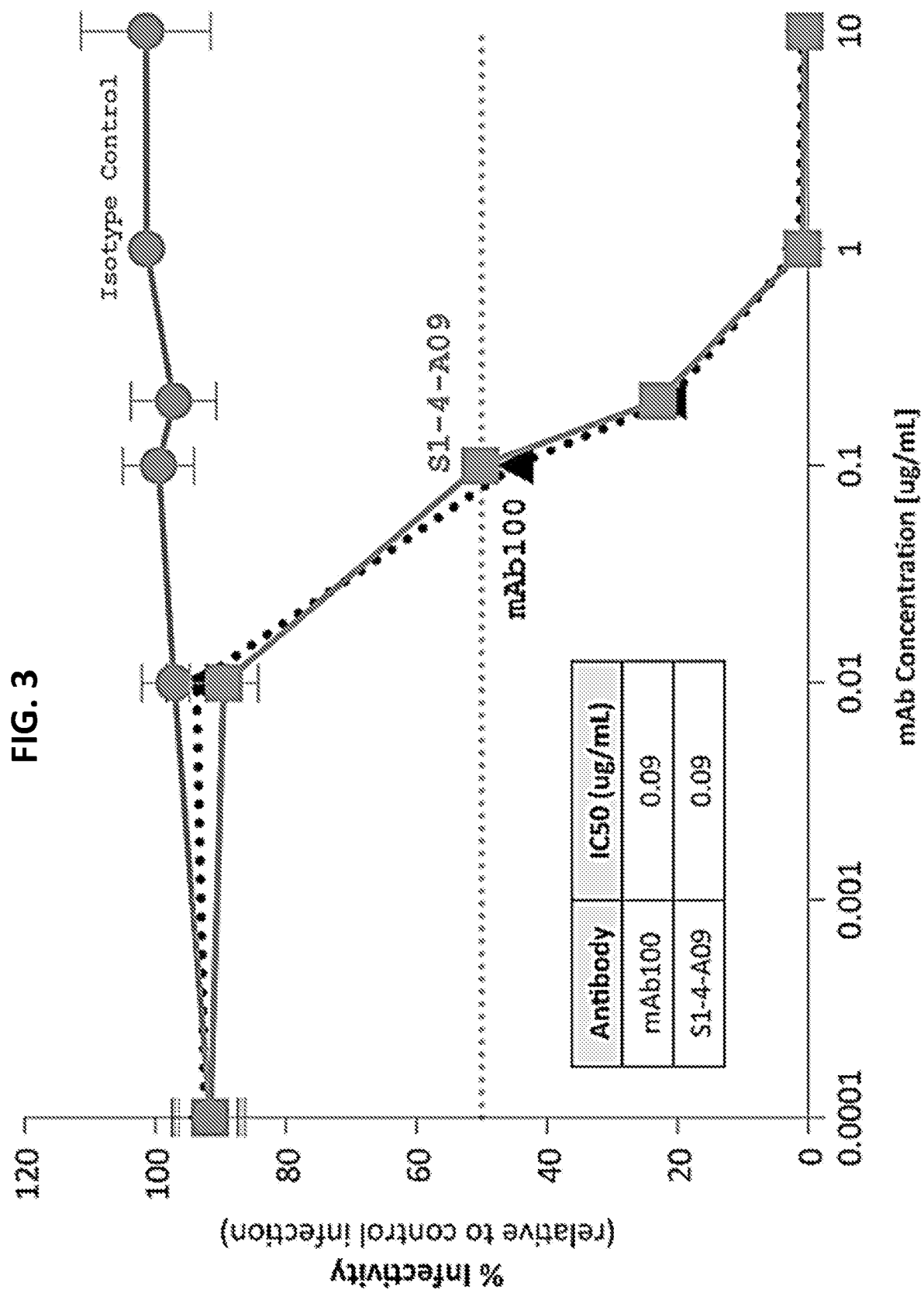
FIG. 3. In vitro neutralization of Zaire ebolavirus GP-pseudotyped lentiviral vectors by S1-4-A09. mAb100 and an isotype control were included in the assay for comparison. The $IC_{50}$ for mAb100 and S1-4-A09 as calculated from the neutralization curve using a four-parameter logistic curve fit is shown in the inset table. Error bars shown represent the standard deviation of triplicate well values.
Figure 4A:
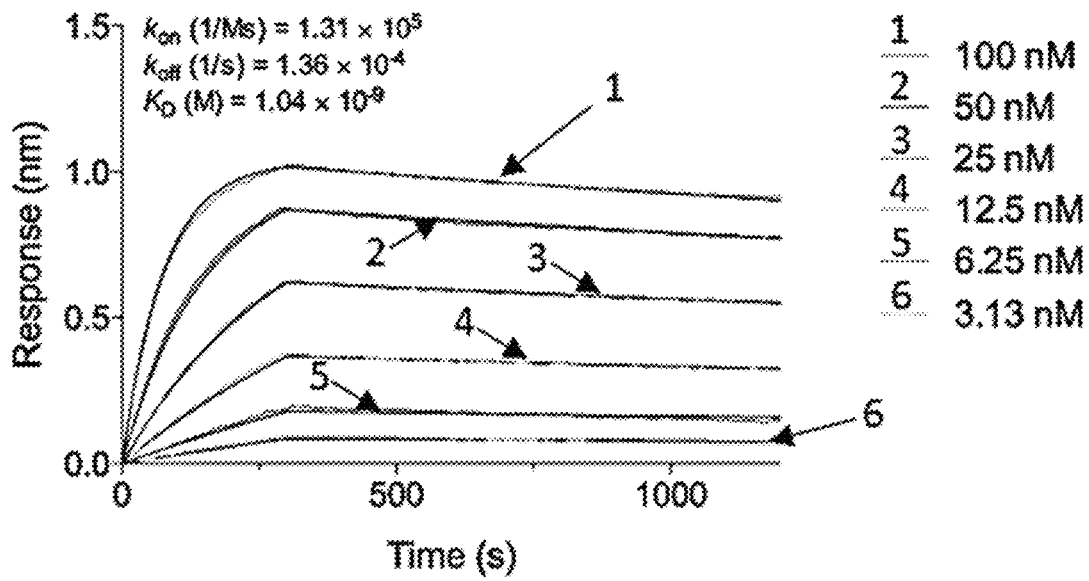
FIGS. 4A-4D. Kinetics of S1-4-A09 Fab binding to GP and GP variants. S1-4-A09 Fab binding to mucin-domain-deleted Zaire ebolavirus GP (ΔMuc), Zaire ebolavirus secreted GP (sGP), and cleaved Zaire ebolavirus GP (THL) at pH 7.4 and 5.3 were measured by biolayer interferometry. $k_{on}$, $k_{off}$, and $K_D$ values were calculated based on a global, nonlinear, least squares, 1:1 binding model curve fit with the assumption of fully reversible binding.
Figure 4B:
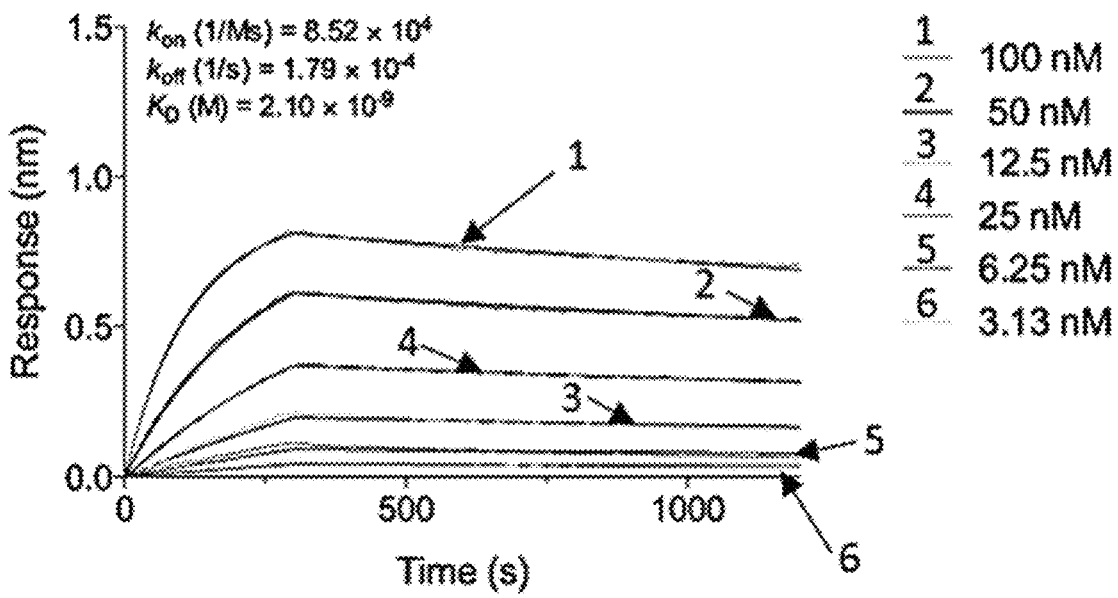
Figure 4C:
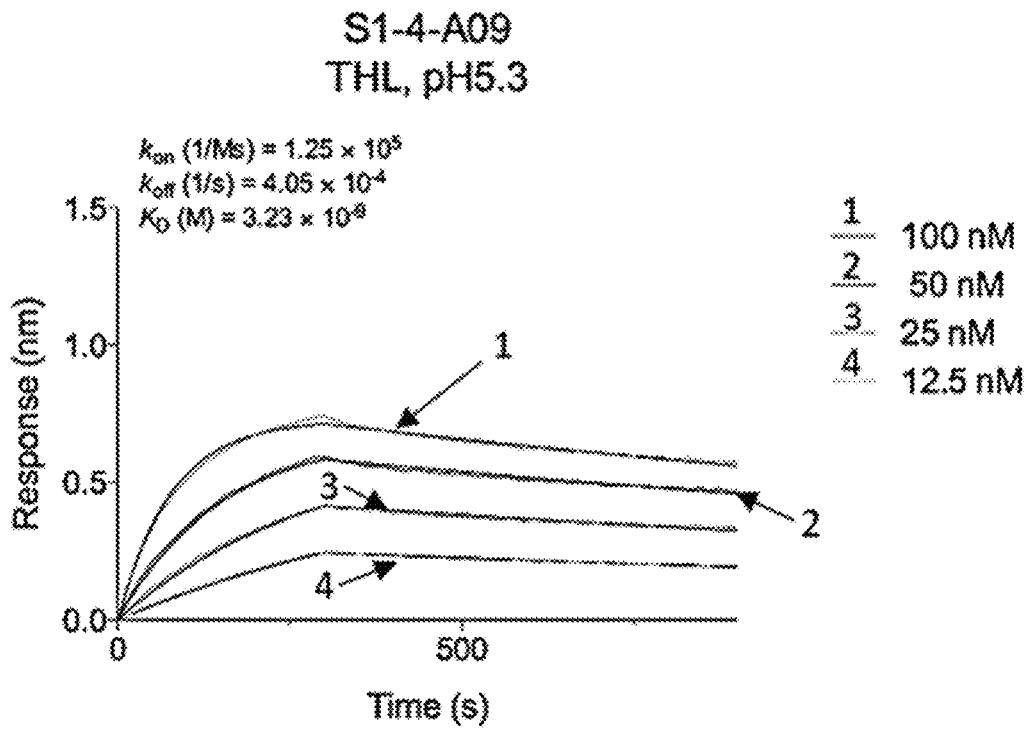
Figure 4D:
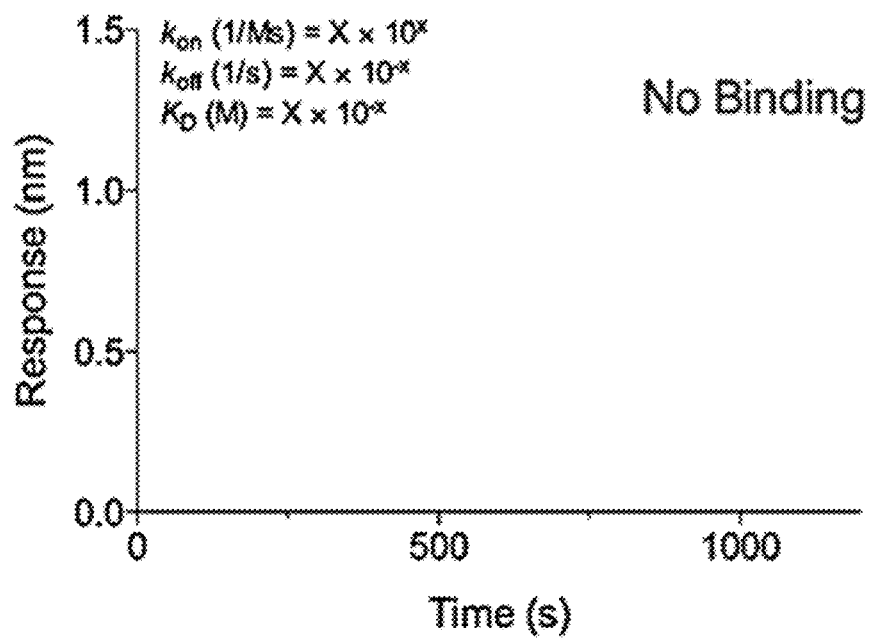

S1-4-A09 was evaluated for its ability to neutralize *Zaire ebolavirus* GP-pseudotyped lentiviral vectors. Antibodies were pre-incubated with the lentiviral vectors prior to their addition to 293T cells in a 96-well plate format. Percent inhibition is calculated relative to infection in the absence of mAb. S1-4-A09 has an $IC_{50}$ of approximately 0.1 µg/mL and shows complete neutralization at 1 µg/mL (FIG. 3).

Kinetics of Binding to Alternate Forms of *Zaire ebolavirus*

Fab generated from S1-4-A09 was evaluated for binding to the mucin-domain-deleted form of *Zaire ebolavirus* GP at pH 7.4 and 5.3, to *Zaire ebolavirus* sGP at pH 7.4, and to cleaved *Zaire ebolavirus* GP (THL) at pH 5.3 by biolayer interferometry (FIGS. 4A-4D). S1-4-A09 Fab shows binding to mucin-domain-deleted *Zaire ebolavirus* GP at pH 7.4 and pH 5.3 with affinity constants ($K_D$) of 1.04 nM and 2.10 nM respectively, and binding to *Zaire ebolavirus* $GP_{THL}$ at pH 5.3 with a $K_D$ of 3.23 nM. As seen in the ELISA data (FIG. 2) with mAb, S1-4-A09 Fab shows no binding to *Zaire ebolavirus* sGP.

Protection of GP from Thermolysin Cleavage

During cellular entry of *Zaire ebolavirus*, the surface trimeric glycoprotein (GP) undergoes an essential cleavage by cysteine proteases called cathepsins (cathepsin L and cathepsin B). This cleavage exposes the receptor binding domain and primes the virus for fusion with the endosomal membrane. This cleavage event can be mimicked in vitro using a bacterial enzyme called thermolysin. Accordingly, S1-4-A09 was evaluated for protection of purified *Zaire ebolavirus* GP from digestion by thermolysin (a surrogate for Cathepsin B) in an in vitro protease protection assay.

Figure 5:
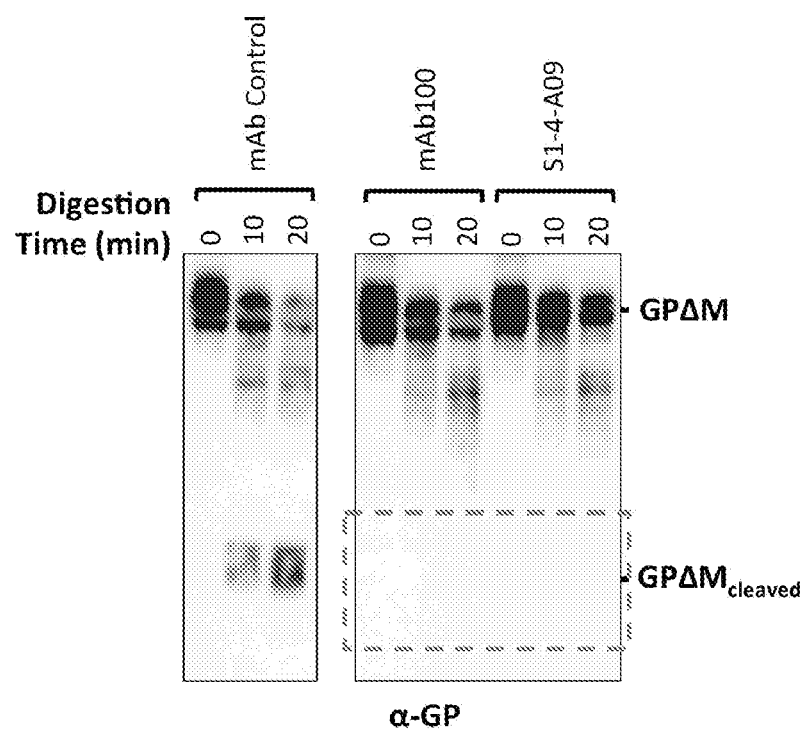
FIG. 5. Immunoblot analysis of antibody-antigen complexes incubated with thermolysin. Mucin-domain-deleted GP (GPΔM) was incubated with mAb100, S1-4-A09, or a mAb control (an Ebola GP-directed mAb known to not inhibit cleavage) for 30 min at room temperature before incubation with thermolysin. The starting antigen is indicated on the blot by "GPΔM" and the cleavage product is indicated by "GPΔM$_{cleaved}$." The dashed box indicates the region of the blot where signal from cleavage product is absent, indicating protection from thermolysin.

Briefly, S1-4-A09 was pre-incubated with mucin-domain-deleted *Zaire ebolavirus* GP for 30 min at room temperature. Samples were then incubated with 0.02 mg/mL of thermolysin and samples were removed at 0 min, 10 min, and 20 min post-enzyme addition. The removed samples were combined with a stop solution, boiled for 10 min and analyzed by immunoblot. S1-4-A09 protected purified mucin-domain-deleted *Zaire ebolavirus* GP from cleavage by thermolysin (FIG. 5).

Epitope Mapping

Gross mapping to determine the mAb epitope on *Zaire ebolavirus* GP was performed by competition measured using biolayer interferometry with other mAbs who have known epitopes. Binding site was also assessed by generating class averages from single-particle transmission electron micrographs of negative-stained samples.

Competition Group Analysis

By assessing how S1-4-A09 competes with previously characterized mAbs, gross epitope can be determined. Competition class was determined using biolayer interferometry. Briefly, biosensors were loaded with purified mucin-domain-deleted *Zaire ebolavirus* GP. The competitor mAb (the mAb determining the class or gross epitope) is then allowed to bind to the antigen and the degree of binding is recorded. Then the analyte mAb is allowed to bind and the degree of binding is recorded. Percent inhibition of the binding of the analyte is calculated as follows:

$$\%\text{Inhibition} = 100 \left( 1 - \frac{\text{signal of analyte binding in the presence of competitor}}{\text{signal of analyte binding in the absence of competitor}} \right)$$

The assay puts S1-4-A09 in the same competition class as mAb100 and KZ52, which are antibodies which bind at the base of *Zaire ebolavirus* GP, suggesting the S1-4-A09 epitope is in a similar location (FIG. 6).

Transmission Electron Microscopy

Figure 7:
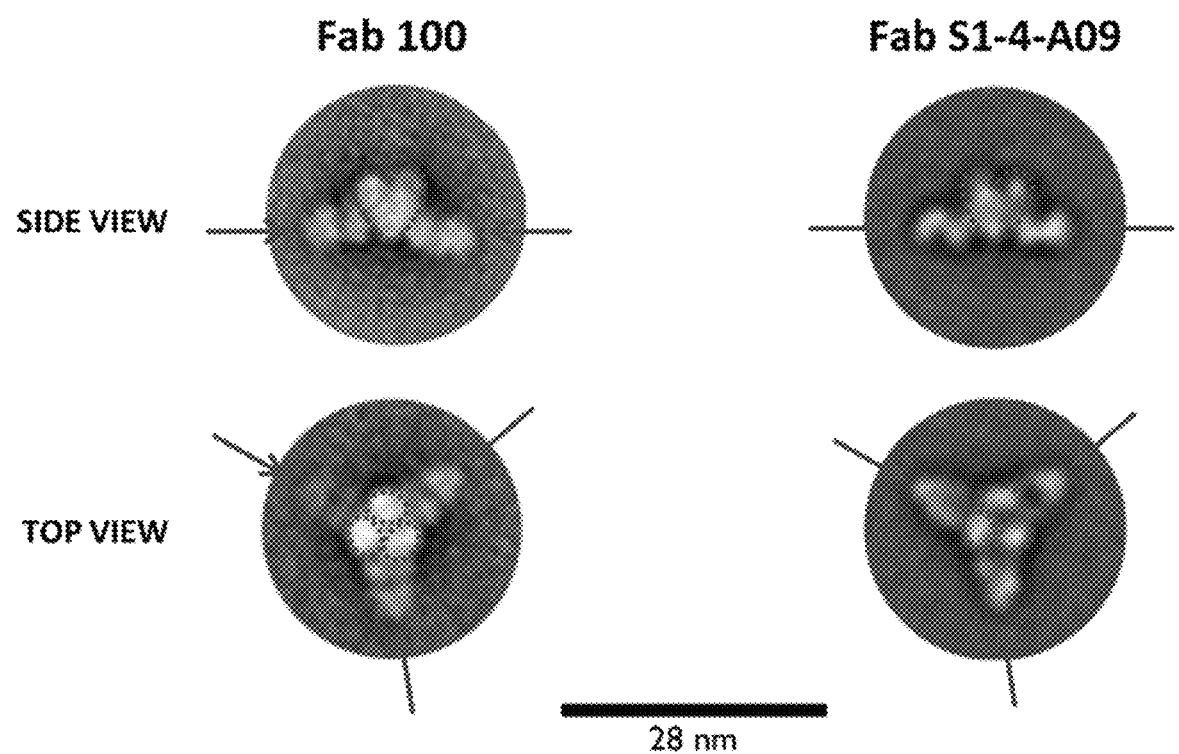
FIG. 7. Exemplary class averages of particles chosen from negative-stain transmission electron micrographs of S1-4-A09 Fab complexed with mucin-domain-deleted GP. Density from GP is outlined in dotted lines. Fab density is indicated by arrows.

Mucin-domain-deleted *Zaire ebolavirus* GP was incubated with molar excess Fab generated from S1-4-A09 to form complexes that were assessed by negative-stain transmission electron microscopy. Class averages were generated from single particle image analysis. Within the set of class averages, classes were identified that showed the binding of Fab to *Zaire ebolavirus* GP in a manner similar to that seen for Fab generated from mAb100 indicating that the binding site on *Zaire ebolavirus* GP is likely to be very similar (FIG. 7).

Manufacturing and Biophysical Risk Assessment of S1-4-A09

S1-4-A09 was evaluated by manufacturing and biophysical risk assessment (MBRA) to determine if the purified mAb had acceptable characteristics for advancement into product development. As shown in Tables 2A and 2B, S1-4-A09 had favorable outcomes for all the parameters assessed.

TABLE 2A

Manufacturing and Biophysical Risk Assessment Assays

| Assay | Assay Description |
|---|---|
| Pro A | Determination of Protein A Titer by ultra-performance liquid chromatography (UPLC) |
| SEC | Determination of high molecular weight species by size exclusion chromatography |
| SEC (Freeze-Thaw 5x) | Determination of high molecular weight species by size exclusion chromatography of sample that has undergone five freeze-thaw cycles. |
| SEC-MALS | Determination of absolute molecular mass by size exclusion chromatography followed by multi-angle light scattering |
| GXII (R/NR) | Determination of purity by R/NR gel electrophoresis. |
| cIEF | Determination of purity by capillary isoelectric focusing. |
| Appearance | Visual examination of the sample |
| UV-VIS (A280, OD350) | Determination of absorbance of the sample by UV-VIS spectroscopy |
| DSC | Determination of melting temperature by differential scanning calorimetry |
| CD | Determination of secondary structure by circular dichroism |
| DLS | Determination of population size and heterogeneity by dynamic light scattering |
| DLS Melt | Determination of colloidal thermal transition by dynamic light scattering thermal ramping |
| PEG | Determination of solubility by PEG exclusion assay |
| ICD | Determination of pH stability by isothermal chemical denaturation |

TABLE 2B

Manufacturing and Biophysical Risk Assessment Summary of Assay Outcomes for S1-4-A09. The assay outcomes for S1-4-A09 (rightmost column) meet, and pass, the pre-set target values for the assays.

| Assay | Attribute | Target Values (VRC01) | S1-4-A09 |
|---|---|---|---|
| Pro A | Chromatographic Profile | Report Result | 2.36 mg/mL |
| SEC | % High Molecular Weight Species (HMW) | Total HMW <5% Monomer >95% | Total HMW: 2.7% Monomer: 97.3% |
| SEC (Freeze-Thaw 5x) | Freeze Stress | No significant change | Total HMW: 2.5% Monomer: 97.5% No Significant Change |
| SEC-MALS | Absolute Molar Mass | Expected Size | HMW 1: 10930 kDa HMW 2: 608 kDa Monomer: 146 kDa |
| GXII (R/NR) | Size/Fragmentation | Reduced (R): Purity >95% Non-Reduced (NR): Report Result | R: 98.2% NR: 98.7% |
| cIEF | Charge Heterogeneity | Report Result | Two Populations: 6 peaks, pI range: 6.13, 8.45-8.88 Acidic population observed |
| Appearance | Appearance | Clear, colorless; no visible particles | Clear, colorless; no visible particles |
| UV-VIS (A280, OD350) | Conc./optical density | Report Result OD350 <0.05 | A280: 0.77 OD350: 0.008 |
| DSC | Thermal Transition Temperature | $T_m1 \geq 70°$ C. | $T_m1$: 75.5° C. |
| CD | Secondary Structure | Primary Minimum at ~218 nm | Primary Min. ~217 nm; Min. at ~230 nm |
| DLS | Pop. Size and heterogeneity | ≥95% material is primary population (~5-6 nm) | 100% material is primary population (5-6.5 nm) |
| DLS Melt | Colloidal/Structural Thermal Transition | $T_{onset} \geq 64°$ C. | $T_{onset} = 64°$ C. |
| PEG | Solubility as a function of pH | % $PEG_{midpt} \geq 9$ at one or more conditions tested | % $PEG_{midpt} \geq 10$ (all conditions tested) |
| ICD | Stability as a function of pH | $C1/2 \geq 5.5$ at one or more conditions tested | $C_{1/2} \geq 5.5$ (pH ≥5.8) |

Autoreactivity Assessment of S1-4-A09

Figure 8:
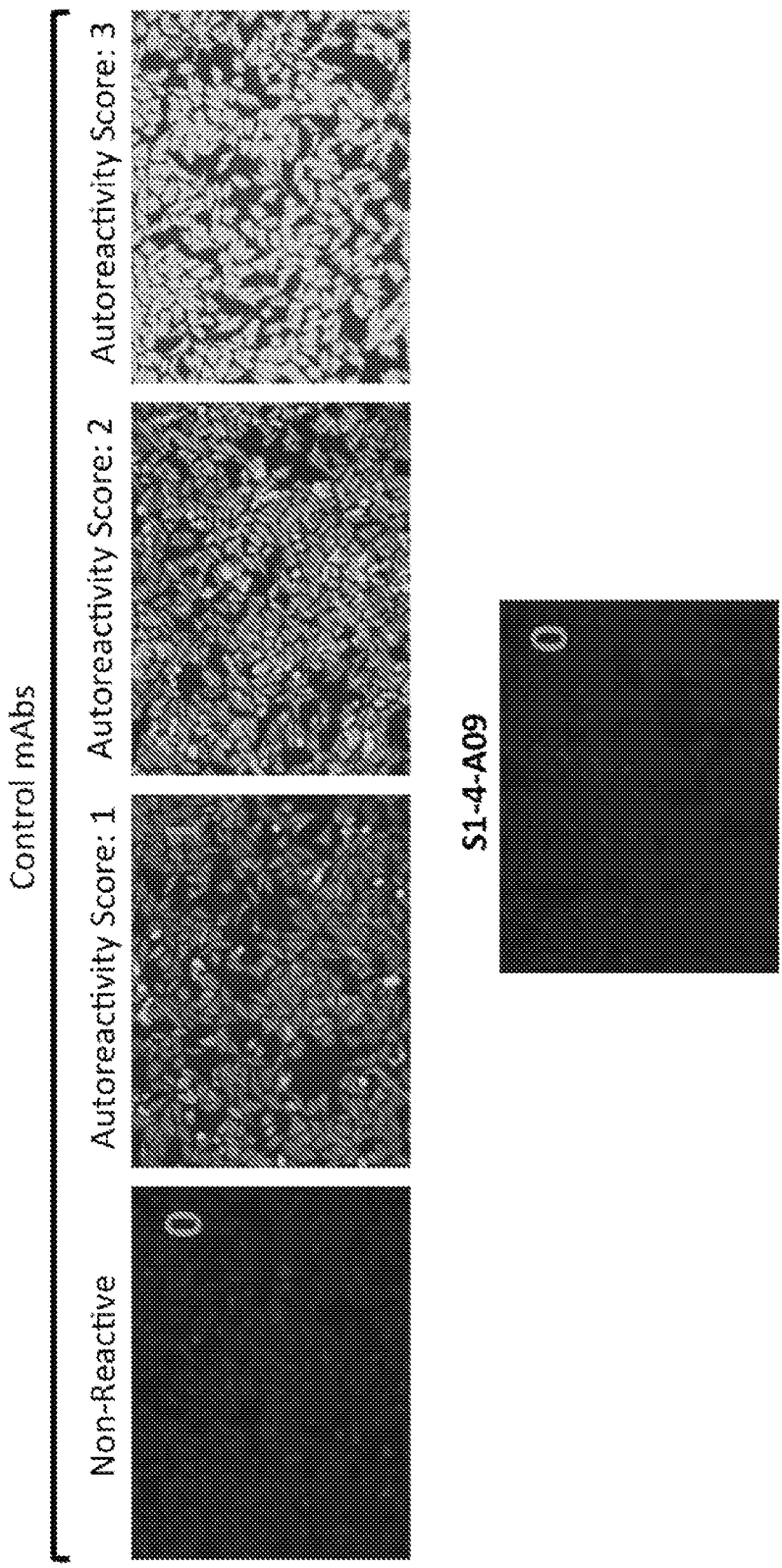
FIG. 8. Antinuclear antibody staining analysis of S1-4-A09 autoreactivity. Staining analysis was done in HEp-2 cells. The top four panels are representative fields of view from an assay with antibodies that have increasing degrees of autoreactivity. The bottom panel is a representative field of view from an assay with S1-4-A09. The autoreactivity score is indicated by the number in the upper right corner of each image.

Potential autoreactivity of S1-4-A09 was evaluated using two assays: an antinuclear antibody staining analysis in HEp-2 cells and an anti-cardiolipin ELISA. Antinuclear antibody staining in HEp-2 cells is evaluated by scoring autoreactivity on a scale from 0 to 3. Scores greater than or equal to 1 are considered autoreactive. S1-4-A09 scored as non-reactive (a score of 0) in duplicate ANA HEp-2 assays (FIG. 8).

The anti-cardiolipin ELISA was run using the Inova Diagnostics QUANTA Lite ACA IgG III kit. S1-4-A09 was evaluated with a 3-fold serial dilution from 100 µg/mL to 1.2 µg/mL. The measured absorbance is converted to a GPL score and the GPL score at the 33 µg/mL dilution is used to evaluate reactivity. A GPL score less than 20 is considered non-reactive, between 20 and 80 inclusive is a low positive, and greater than 80 is a high positive. As shown in Table 3, S1-4-A09 scored as non-reactive.

TABLE 3

Anti-cardiolipin ELISA for S1-4-A09. Absorbance, GPL units, and reactivity interpretation at the 33 µg/mL dilution point are listed for three control antibodies and S1-4-A09.

| mAb | Absorbance | GPL units | Reactivity |
| --- | --- | --- | --- |
| Negative control mAb | 0.04 | −3.45 | Non-reactive |
| Low reactive control mAb | 0.36 | 25.35 | Low positive |
| High reactive control mAb | 1.91 | 163.07 | High positive |
| S1-4-A09 | 0.15 | 6.73 | Non-reactive |

In Vivo Efficacy Against Lethal *Zaire ebolavirus* Challenge of Macaques

The macaque model of *Zaire ebolavirus* infection is the standard for assessing vaccines and antivirals against EVD caused by this species of ebolavirus. Macaques are challenged by the intramuscular route (IM) with a target dose of 1000 PFU early-passage *Zaire ebolavirus*. This virus dose is uniformly lethal in naïve macaques and death occurs between 6 and 12 days after virus challenge. Challenges are performed at USAMRIID, where >50 historical controls have been infected. The use of historical controls in challenge studies allows statistically significant determination of treatment efficacy using small treatment groups of 3-4 macaques per group and a single untreated control subject.

Administration of S1-4-A09 Alone

S1-4-A09 was administered to macaques in three intravenous (IV) injections at 24-hour intervals at a dosage of 50 mg/kg/dose beginning 24 hours after lethal challenge (1000 PFU) with *Zaire ebolavirus* (FIG. 9). Two out of the three animals in the group administered S1-4-A09 alone survived *Zaire ebolavirus* challenge to at least 28 days post-infection.

Administration of S1-4-A09 in Combination with mAb114

Figure 10:
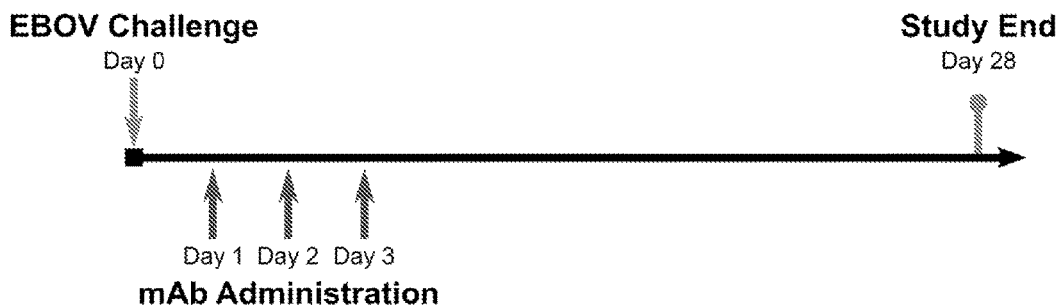
FIG. 10. In vivo neutralization of Zaire ebolavirus infection by combination therapy with S1-4-A09 IgG and mAb114 IgG. Top, schematic of Zaire ebolavirus challenge and S1-4-A09-mAb114 antibody mixture dosing timeline for in vivo efficacy studies. Middle, dosages of S1-4-A09 and mAb114 antibody mixtures administered intravenously to macaques for in vivo neutralization studies. Bottom, Kaplan-Meier curves for survival in the in vivo efficacy study for S1-4-A09 in combination with mAb114. The 50:50 114/A09 curve represents the group where animals received three doses of S1-4-A09 with mAb114 in a 50% to 50% ratio (A09:114) at a total antibody dosage of 50 mg/kg/dose. The 92:8 11/4A09 curve represents the group where animals received three doses of S1-4-A09 with mAb114 in an 8% to 92% ratio (A09:114) at a total antibody dosage of 50 mg/kg/dose. Animals of the control group were not administered any antibody.
Figure 10:
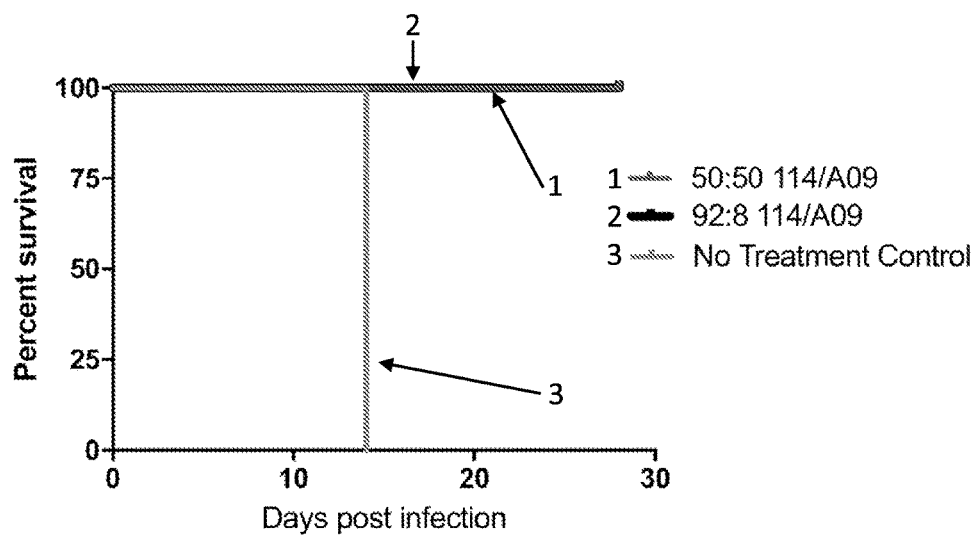

S1-4-A09-mAb114 antibody mixtures were administered to macaques in three intravenous (IV) injections at 24-hour intervals at a dosage of 50 mg/kg/dose beginning 24 hours after lethal challenge (1000 PFU) with *Zaire ebolavirus* (FIG. 10). Two different ratios of mAb114 to S1-4-A09 were tested: 1) 92% mAb114:8% S1-4-A09; 2) 50% mAb114: 50% S1-4-A09 (FIG. 10). Three out of the three animals in each of the groups administered S1-4-A09-mAb114 mixtures survived *Zaire ebolavirus* challenge to at least 28 days post-infection.

Example 2

*Ebolavirus* GP Specific Monoclonal Antibody S1-4-A09 A61P

This example illustrates the identification and characterization of the S1-4-A09 A61P antibody, which specifically binds to *Zaire ebolavirus* GP and can neutralize *Zaire ebolavirus*.

N-Linked Glycan Sequon Mutant of S1-4-A09

Figure 11:
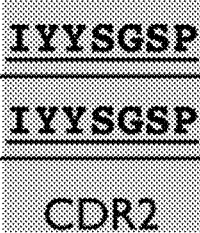
FIG. 11. Alignment of the S1-4-A09, S-14-A09 A61P, mAb100, and mAb100 unmutated common ancestor (UCA) heavy chain sequences, with the N-linked glycan sequon and A61P mutation annotated. Residues 70-88 (IMGT numbering) from the heavy chains of the mAb100 UCA (SEQ ID NO: 31), mAb100 (corresponding to residues 51-69 of SEQ ID NO: 23), S1-4-A09 (corresponding to residues 51-69 of SEQ ID NO: 1) and S1-4-A09 A61P (corresponding to residues 51-69 of SEQ ID NO: 3) are shown. The CDR2 of the heavy chain is underlined and highlighted by the highlighted box. The N-linked glycan sequons are shown by small open boxes. The A61P point mutation is indicated with an arrow.

The presence of the sequon Asn-X-Thr where X is an amino acid that is not proline in the antibody variable domain is considered a potential manufacturing liability due to the potential for heterogeneous N-linked glycosylation occurring at this site during production. Both S1-4-A09 and the related mAb100 have sequons present C-terminal to the HCDR2. In order to abolish the sequon in S1-4-A09, residue A61 (Kabat positioning) was mutated to proline (FIG. 11). Proline was chosen as this is the amino acid present at this position in the unmutated common ancestor (UCA) of mAb100.

ELISA Binding of S1-4-A09 A61P to *Zaire ebolavirus* GP

Figure 12:
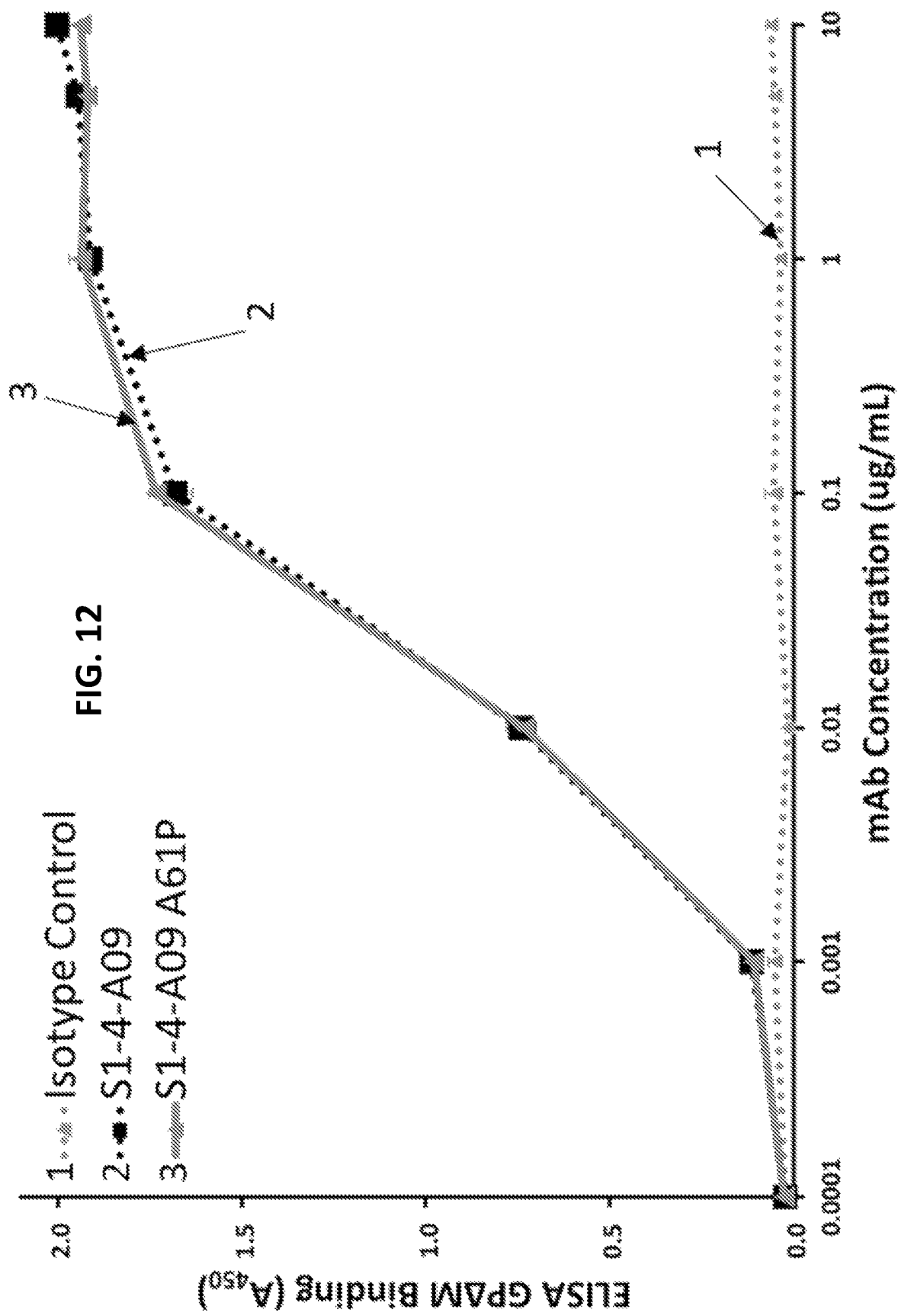
FIG. 12. Binding of S1-4-A09 A61P to Zaire ebolavirus mucin-domain-deleted GP (GPΔM) as assayed by ELISA. Binding curves for the isotype control, S1-4-A09, and S1-4-A09 A61P are shown. Error bars shown represent the standard error of the mean of triplicate wells for each dilution point.

ELISA assays were performed using plates coated with bicarbonate buffer containing purified mucin-domain-deleted GP (GPΔM) expressed from Expi293 cells (Invitrogen). S1-4-A09 A61P binding was evaluated in comparison to S1-4-A09 and an isotype control. S1-4-A09 A61P shows binding to GPΔM very similar to that of S1-4-A09 (FIG. 12).

In Vitro Neutralization by S1-4-A09 A61P

Figure 13:
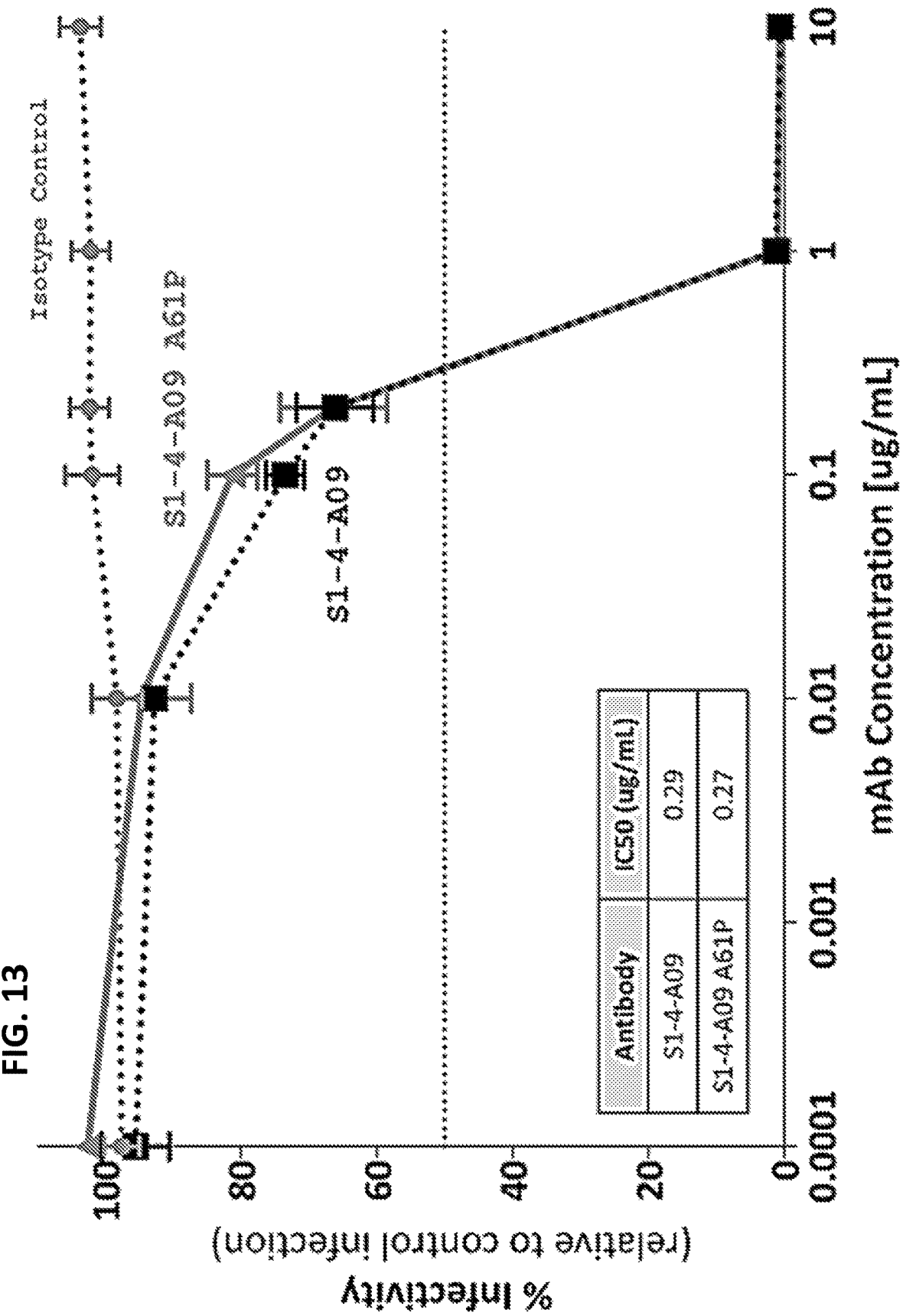
FIG. 13. In vitro neutralization of Zaire ebolavirus GP-pseudotyped lentiviral vectors by S1-4-A09 A61P. S1-4-A09 and an isotype control were included in the assay for comparison. The $IC_{50}$ for S1-4-A09 and S1-4-A09 A61P as calculated from the neutralization curve using a four-parameter logistic curve fit is shown in the inset table. Error bars shown represent the standard deviation of triplicate well values.

S1-4-A09 A61P was evaluated for its ability to neutralize *Zaire ebolavirus* GP-pseudotyped lentiviral vectors. mAbs were pre-incubated with the lentiviral vectors prior to their addition to 293T cells in a 96-well plate format. Percent inhibition is calculated relative to infection in the absence of mAb. S1-4-A09 A61P has an $IC_{50}$ of approximately 0.3 µg/mL and shows complete neutralization at 1 µg/mL, similarly to S1-4-A09 in the same assay (FIG. 13).

Protection by S1-4-A09 A61P of GP from Thermolysin Cleavage

Figure 14:
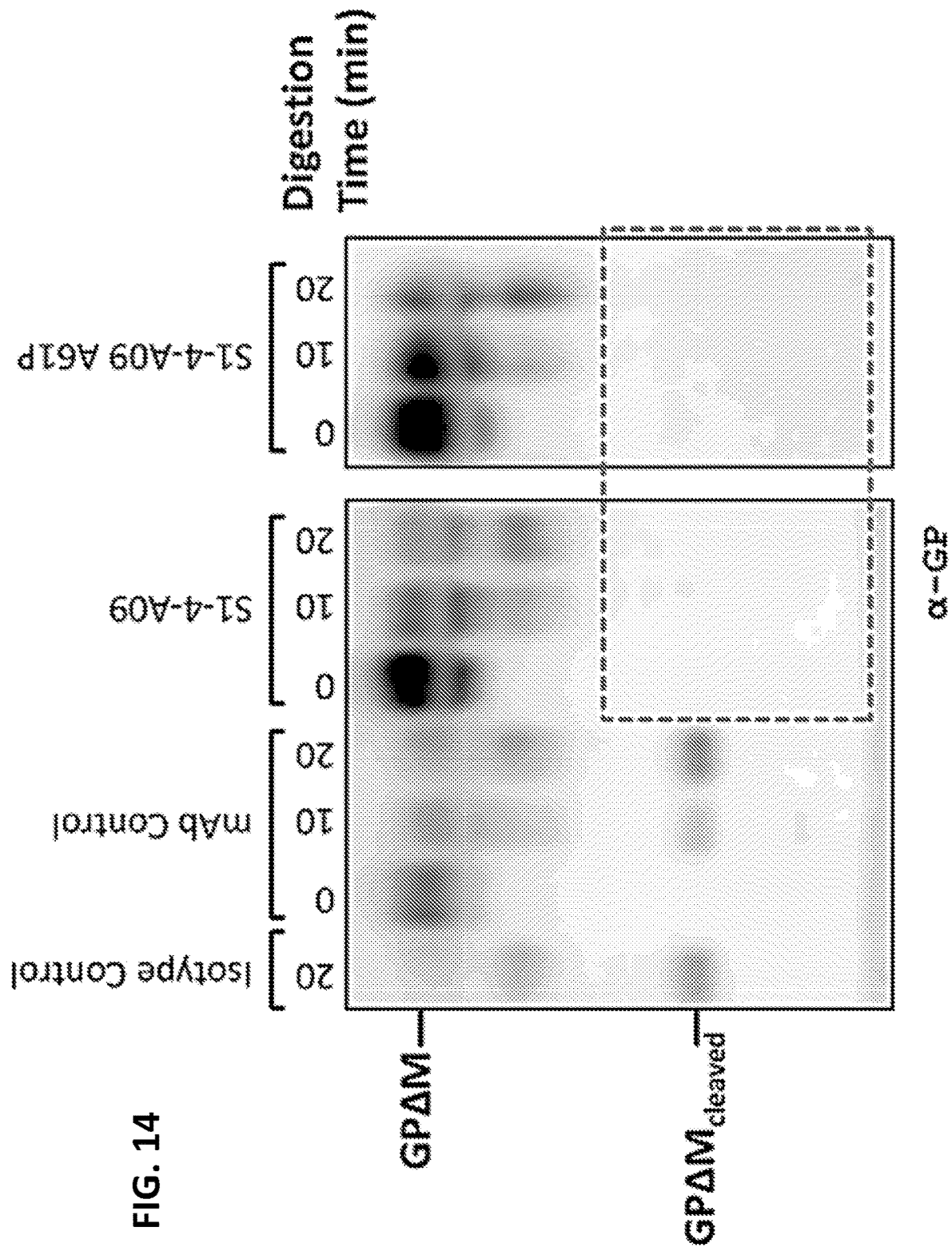
FIG. 14. Immunoblot analysis of antibody-antigen complexes incubated with thermolysin. Mucin-domain-deleted GP (GPΔM) was incubated with S1-4-A09, S1-4-A09 A61P, a mAb control (an Ebola GP-directed mAb known to not inhibit cleavage), and an isotype control (a mAb not directed towards Ebola GP) for 30 min at room temperature before incubation with thermolysin. The starting antigen is indicated on the blot by "GPΔM" and the cleavage product is indicated by "GPΔM$_{cleaved}$." The dashed box indicates the region of the blot where signal from cleavage product is absent, indicating protection from thermolysin.

S1-4-A09 A61P was pre-incubated with mucin-domain-deleted GP for 30 min at room temperature. Samples were then incubated with 0.02 mg/mL of thermolysin and samples were removed at 0 min, 10 min, and 20 min post-enzyme addition. The removed samples were combined with a stop solution, boiled for 10 min and analyzed by immunoblot. S1-4-A09 A61P protected purified mucin-domain-deleted GP from cleavage by thermolysin (FIG. 14).

S1-4-A09 Kinetics of Binding to *Zaire ebolavirus* GP

S1-4-A09 A61P was evaluated for binding to the mucin-domain-deleted form of *Zaire ebolavirus* GP at pH 7.4 by biolayer interferometry (Table 4). S1-4-A09 A61P shows binding to mucin-domain-deleted *Zaire ebolavirus* GP at pH 7.4 with an apparent affinity constant ($K_D$) of approximately 0.1 nM.

TABLE 4

Kinetics of S1-4-A09 A61P mAb Binding to
Zaire ebolavirus GP. Binding of S1-4-A09 and S1-
4-A09 A61P mAb to mucin-domain-deleted
Zaire ebolavirus GP (ΔMuc) at pH 7.4 was measured by
biolayer interferometry. $k_{on}$, $k_{off}$, and $K_D$ values
were calculated based on a global, nonlinear, least squares,
1:2 bivalent binding model curve fit with the
assumption of fully reversible binding.

|  | $K_D$ (M) | $K_{on}$ (M$^{-1}$s$^{-1}$) | $K_{off}$ (s$^{-1}$) |
|---|---|---|---|
| mAb100 | $6.28 \times 10^{-11}$ | $1.43 \times 10^5$ | $8.91 \times 10^{-6}$ |
| S1-4-A09 | $1.27 \times 10^{-10}$ | $1.66 \times 10^5$ | $2.09 \times 10^{-5}$ |
| S1-4-A09 A61P | $9.86 \times 10^{-11}$ | $1.55 \times 10^5$ | $1.51 \times 10^{-5}$ |

Example 3

Antibodies Specific to *Zaire ebolavirus* GP for Detecting *Zaire ebolavirus* in a Sample or a Subject This example describes an exemplary use of a monoclonal antibody that specifically binds to *Zaire ebolavirus* GP for the detection of *Zaire ebolavirus* in a sample or a subject. This example further describes the use of these antibodies to confirm the diagnosis of *Zaire ebolavirus* infection in a subject.

A biological sample, such as a blood sample, is obtained from the patient diagnosed with, undergoing screening for, or suspected of having, a *Zaire ebolavirus* infection. A blood sample can be taken from a patient who is not infected and used as a control; alternatively, a standard result can also be used as a control. An ELISA is performed to detect the presence of *Zaire ebolavirus* in the blood sample. Proteins present in the blood samples (the patient sample and control sample) are immobilized on a solid support, such as a 96-well plate, according to standard methods (see, for example, Robinson et al., Lancet, 362(9396):1612-1616, 2003, incorporated herein by reference). Following immobilization, antibody that specifically binds to *Zaire ebolavirus* GP and are directly labeled with a fluorescent marker are applied to the protein-immobilized plate. The plate is washed in an appropriate buffer, such as PBS, to remove any unbound antibody and to minimize non-specific binding of antibody. Fluorescence can be detected using a fluorometric plate reader according to standard methods. An increase in fluorescence intensity of the patient sample, relative to the control sample, indicates the *Zaire ebolavirus* GP antibody specifically bound proteins from the blood sample, thus detecting the presence of *Zaire ebolavirus* protein in the sample. Detection of *Zaire ebolavirus* protein in the patient sample indicates the patient has *Zaire ebolavirus* infection, or confirms diagnosis of *Zaire ebolavirus* in the subject.

Example 4

Monoclonal Antibodies Specific for *Zaire ebolavirus* GP for the Treatment of *Zaire ebolavirus*

This example describes a particular method that can be used to treat *Zaire ebolavirus* infection in a human subject by administration of one or more antibodies or antigen binding fragments that specifically bind to *Zaire ebolavirus* GP and neutralize *Zaire ebolavirus*. Although particular methods, dosages, and modes of administrations are provided, one skilled in the art will appreciate that variations can be made without substantially affecting the treatment.

Screening Subjects

In particular examples, the subject is first screened to determine if they have a *Zaire ebolavirus* infection. Examples of methods that can be used to screen for *Zaire ebolavirus* infection include evaluating the patient for EVD (e.g., hemorrhagic fever), determining prior exposure to Zaire-ebolavirus-infected subjects or *Zaire ebolavirus* materials (e.g., bodily fluids from a Zaire-ebolavirus-infected patient), and/or measuring the levels of one or more *Zaire ebolavirus* proteins or nucleic acids in a biological sample from the subject (e.g., assaying for *Zaire ebolavirus* sGP in a blood sample from the subject).

In some examples, *Zaire ebolavirus* testing consists of initial screening with an ELISA to detect antibodies to a *Zaire ebolavirus* protein, such as *Zaire ebolavirus* GP. Specimens with a reactive ELISA result are retested in duplicate. If the result of the duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered *Zaire ebolavirus*-positive and indicative of *Zaire ebolavirus* infection. In additional examples, nucleic acid testing (e.g., viral RNA amplification method) can also help diagnosis in certain situations.

The detection of *Zaire ebolavirus* protein in a subject's blood is indicative that the subject is infected with *Zaire ebolavirus* and is a candidate for receiving the therapeutic compositions disclosed herein. However, pre-screening is not required prior to administration of the therapeutic compositions disclosed herein.

Administration of Therapeutic Compositions

Following subject selection, a therapeutically effective amount of an ebolavirus GP-specific mAb described herein (e.g., S1-4-A09 or S1-4-A09 A61P) or a combination of such mAbs is administered to the subject (such as an adult human either at risk for contracting *Zaire ebolavirus* or known to be infected with *Zaire ebolavirus*). Additional agents, such as anti-viral agents, can also be administered to the subject simultaneously or prior to or following administration of the disclosed mAb. Typically, the antibody is administered intravenously.

The amount of the antibody administered to prevent, reduce, inhibit, and/or treat *Zaire ebolavirus* or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., EVD) in a subject without causing a substantial cytotoxic effect in the subject. An effective amount can be readily determined by one skilled in the art, for example using routine trials establishing dose-response curves. As such, these compositions may be formulated with an inert diluent or with a pharmaceutically acceptable carrier.

In one specific example, a subject known to have a *Zaire ebolavirus* infection is administered 50 mg/kg of a disclosed antibody (or combination thereof) every day for 3 days following initial diagnosis of *Zaire ebolavirus* infection. In another example, the antibodies are administered continuously.

Assessment

Following the administration of one or more therapies, subjects with *Zaire ebolavirus* can be monitored for a reduction in *Zaire ebolavirus* levels (such as through viral titer or ebolavirus GP levels in serum), or reductions in one or more clinical symptoms associated with *Zaire ebolavirus* infection. Subjects can be monitored using any method known in the art. For example, biological samples from the subject, including blood, can be obtained and alterations in *Zaire ebolavirus* levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 50% reduction in *Zaire ebolavirus* infection (e.g., as measured by *Zaire ebolavirus* GP level or viral titer in serum), *Zaire ebolavirus* replication, or combination thereof.

It will be apparent that the precise details of the embodiments described may be varied or modified without departing from the spirit of the described embodiments. We claim all such modifications and variations that fall within the scope and spirit of the claims below.

The invention claimed is:

1. An isolated monoclonal antibody, comprising:
a heavy chain variable region ($V_H$) comprising a heavy chain complementarity determining region (HCDR)1, a HCDR2, and a HCDR3 of the $V_H$ set forth as SEQ ID NO: 1;
a light chain variable region ($V_L$) comprising a light chain complementarity determining region (LCDR)1, a LCDR2, and a LCDR3 of the $V_L$ set forth as SEQ ID NO: 2; and
wherein the monoclonal antibody specifically binds to an ebolavirus glycoprotein (GP) and neutralizes an ebolavirus.

2. The antibody of claim 1, wherein the HCDR1, the HCDR2, the HCDR3, the LCDR1, the LCDR2, and the LCDR3 comprise the amino acids sequences set forth as SEQ ID NOs: 7-12, respectively.

3. The antibody of claim 1, wherein the $V_H$ does not contain an N-linked glycan sequon beginning at any of Kabat residues 58-60.

4. The antibody of claim 1, wherein the $V_H$ does not contain an N-linked glycan sequon in a framework region 3 of the antibody.

5. The antibody of claim 1, comprising one or more amino acid substitutions to remove an N-linked glycan sequon beginning at Kabat position 60.

6. The antibody of claim 5, wherein the $V_H$ comprises an A61P substitution to remove the N-linked glycan sequon.

7. The antibody of claim 1, wherein the $V_H$ comprises an amino acid sequence at least 90% identical to SEQ ID NO: 1 or SEQ ID NO: 3.

8. The antibody of claim 1, wherein the $V_L$ comprises an amino acid sequence at least 90% identical to SEQ ID NO: 2.

9. The antibody of claim 1, comprising human framework regions.

10. The antibody of claim 1, wherein the $V_H$ comprises the amino acid sequence set forth as SEQ ID NO: 3.

11. The antibody of claim 1, wherein the $V_H$ comprises the amino acid sequence set forth as SEQ ID NO: 1.

12. The antibody of claim 1, wherein the $V_L$ comprises the amino acid sequence set forth as SEQ ID NO: 2.

13. The antibody of claim 1, wherein the $V_H$ and the $V_L$ comprise the amino acid sequences set forth as SEQ ID NOs: 1 and 2, respectively, or SEQ ID NOs: 3 and 2, respectively.

14. The antibody of claim 1, wherein the antibody comprises a human constant domain.

15. The antibody of claim 1, wherein the antibody is a human antibody.

16. The antibody of claim 1, wherein the antibody is an IgG.

17. The antibody of claim 16, wherein the antibody is an $IgG_1$.

18. The antibody of claim 1, comprising a recombinant constant domain comprising a modification that increases the half-life of the antibody.

19. The antibody of claim 18, wherein the modification increases binding to the neonatal Fc receptor.

20. The antibody of claim 1, comprising heavy and light chains comprising the amino acid sequences set forth as SEQ ID NOs: 4 and 5, respectively, or SEQ ID NOs: 6 and 5, respectively.

21. An isolated antigen binding fragment of the antibody of claim 1, wherein the antigen binding fragment comprises the $V_H$ and the $V_L$ of the antibody, specifically binds to the ebolavirus GP and neutralizes an ebolavirus.

22. The antigen binding fragment of claim 21, wherein the antigen binding fragment is a Fv, Fab, $F(ab')_2$, scFV or a $scFV_2$ fragment.

23. The antibody of claim 1, conjugated to an effector molecule or a detectable marker.

24. The antibody claim 1, wherein the antibody specifically binds to *Zaire ebolavirus* GP and neutralizes *Zaire ebolavirus*.

25. An isolated nucleic acid molecule encoding the $V_H$, the $V_L$, or the $V_H$ and the $V_L$ of the antibody of claim 1.

26. The nucleic acid molecule of claim 25, wherein the nucleic acid sequence of the $V_H$ is set forth as SEQ ID NO: 13 or SEQ ID NO: 15, and the nucleic acid sequence of the $V_L$ is set forth as SEQ ID NO: 14.

27. The nucleic acid molecule of claim 25, comprising a cDNA or RNA encoding the antibody or antigen binding fragment.

28. The nucleic acid molecule of claim 25, operably linked to a promoter.

29. An expression vector comprising the nucleic acid molecule of claim 25.

30. A pharmaceutical composition for use in inhibiting an ebolavirus infection, comprising:
the antibody of claim 1; and
a pharmaceutically acceptable carrier.

31. A method of producing an antibody or antigen binding fragment that specifically binds to ebolavirus GP, comprising:
expressing one or more nucleic acid molecules encoding the antibody of claim 1 in a host cell; and
purifying the antibody or antigen binding fragment.

32. A method of detecting the presence of an ebolavirus in a biological sample from a subject, comprising:
contacting the biological sample with an effective amount of the antibody of claim 1 under conditions sufficient to form an immune complex; and
detecting the presence of the immune complex on the biological sample, wherein the presence of the immune complex on the biological sample indicates the presence of the ebolavirus in the sample.

33. The method of claim 32, wherein detecting the presence of the immune complex in the biological sample indicates that the subject has an ebolavirus infection.

34. A method of inhibiting an ebolavirus infection in a subject, comprising administering an effective amount of the antibody of claim 1 to the subject, wherein the subject has or is at risk of an ebolavirus infection.

35. The method of claim 34, further comprising administering to the subject one or more additional antibodies or antigen binding fragments that specifically bind to the ebolavirus GP and neutralize the ebolavirus, or one or more nucleic acid molecules encoding the additional antibodies or antigen binding fragments.

36. The method of claim 34, wherein the ebolavirus is *Zaire ebolavirus*.

* * * * *

SEQUENCE LISTING

```
<160> NUMBER OF SEQ ID NOS: 31

<210> SEQ ID NO 1
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ile Leu Ser Ser Phe
            20                  25                  30

Tyr Trp Asn Trp Ile Arg Gln Pro Pro Gly Lys Gly Leu Glu Trp Ile
        35                  40                  45

Gly Asn Ile Tyr Tyr Ser Gly Ser Pro Asn Tyr Asn Ala Ser Phe Gln
    50                  55                  60

Ser Arg Val Ala Ile Ser Val Asp Thr Ser Lys Asn Gln Ile Ser Leu
65                  70                  75                  80

Asn Leu Lys Ser Val Thr Ala Ala Asp Thr Ala Met Tyr Tyr Cys Val
                85                  90                  95

Arg Ala Ser Arg Ala Tyr Leu Trp Gly Ser Tyr Arg Pro Thr Ala Leu
            100                 105                 110

Asp Leu Trp Gly Gln Gly Ser Leu Val Thr Val Ser Ser
        115                 120                 125

<210> SEQ ID NO 2
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 2

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Asp Lys Tyr Thr
            20                  25                  30

Ser Trp Phe Gln Gln Arg Pro Gly Gln Ser Pro Leu Leu Val Ile Tyr
        35                  40                  45

Gln Asp Asn Lys Arg Pro Ser Gly Leu Pro Ala Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Leu Cys Gln Val Trp Asp Ser Gly Ala Val Phe
                85                  90                  95
```

```
Gly Gly Gly Thr Lys Leu Thr Val Leu
            100                 105

<210> SEQ ID NO 3
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ile Leu Ser Ser Phe
            20                  25                  30

Tyr Trp Asn Trp Ile Arg Gln Pro Pro Gly Lys Gly Leu Glu Trp Ile
        35                  40                  45

Gly Asn Ile Tyr Tyr Ser Gly Ser Pro Asn Tyr Asn Pro Ser Phe Gln
    50                  55                  60

Ser Arg Val Ala Ile Ser Val Asp Thr Ser Lys Asn Gln Ile Ser Leu
65                  70                  75                  80

Asn Leu Lys Ser Val Thr Ala Ala Asp Thr Ala Met Tyr Tyr Cys Val
                85                  90                  95

Arg Ala Ser Arg Ala Tyr Leu Trp Gly Ser Tyr Arg Pro Thr Ala Leu
            100                 105                 110

Asp Leu Trp Gly Gln Gly Ser Leu Val Thr Val Ser Ser
        115                 120                 125

<210> SEQ ID NO 4
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 4

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ile Leu Ser Ser Phe
            20                  25                  30

Tyr Trp Asn Trp Ile Arg Gln Pro Pro Gly Lys Gly Leu Glu Trp Ile
        35                  40                  45

Gly Asn Ile Tyr Tyr Ser Gly Ser Pro Asn Tyr Asn Ala Ser Phe Gln
    50                  55                  60

Ser Arg Val Ala Ile Ser Val Asp Thr Ser Lys Asn Gln Ile Ser Leu
65                  70                  75                  80

Asn Leu Lys Ser Val Thr Ala Ala Asp Thr Ala Met Tyr Tyr Cys Val
                85                  90                  95

Arg Ala Ser Arg Ala Tyr Leu Trp Gly Ser Tyr Arg Pro Thr Ala Leu
            100                 105                 110

Asp Leu Trp Gly Gln Gly Ser Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175
```

-continued

Thr Phe Pro Ala Val Leu Gln Ser Ser Gly Leu Tyr Ser Leu Ser Ser
                180                 185                 190

Val Val Thr Val Pro Ser Ser Leu Gly Thr Gln Thr Tyr Ile Cys
            195                 200                 205

Asn Val Asn His Lys Pro Ser Asn Thr Lys Val Asp Lys Lys Val Glu
    210                 215                 220

Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln Tyr
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 5
<211> LENGTH: 211
<212> TYPE: PRT
<213> ORGANISM: Artificial Sequence
<220> FEATURE:
<223> OTHER INFORMATION: Synthetic polypeptide

<400> SEQUENCE: 5

Ser Tyr Glu Leu Thr Gln Pro Pro Ser Val Ser Val Ser Pro Gly Gln
1               5                   10                  15

Thr Ala Thr Ile Thr Cys Ser Gly Asp Lys Leu Gly Asp Lys Tyr Thr
            20                  25                  30

Ser Trp Phe Gln Gln Arg Pro Gly Gln Ser Pro Leu Leu Val Ile Tyr
        35                  40                  45

Gln Asp Asn Lys Arg Pro Ser Gly Leu Pro Ala Arg Phe Ser Gly Ser
    50                  55                  60

Asn Ser Gly Asn Thr Ala Thr Leu Thr Ile Ser Gly Thr Gln Ala Met
65                  70                  75                  80

```
Asp Glu Ala Asp Tyr Leu Cys Gln Val Trp Asp Ser Gly Ala Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
    130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
                165                 170                 175

Leu Ser Leu Thr Pro Glu Gln Trp Lys Ser His Arg Ser Tyr Ser Cys
            180                 185                 190

Gln Val Thr His Glu Gly Ser Thr Val Glu Lys Thr Val Ala Pro Thr
        195                 200                 205

Glu Cys Ser
    210

<210> SEQ ID NO 6
<211> LENGTH: 455
<212> TYPE: PRT
<213> ORGANISM: Artificial Sequence
<220> FEATURE:
<223> OTHER INFORMATION: Synthetic polypeptide

<400> SEQUENCE: 6

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ile Leu Ser Ser Phe
            20                  25                  30

Tyr Trp Asn Trp Ile Arg Gln Pro Pro Gly Lys Gly Leu Glu Trp Ile
        35                  40                  45

Gly Asn Ile Tyr Tyr Ser Gly Ser Pro Asn Tyr Asn Pro Ser Phe Gln
    50                  55                  60

Ser Arg Val Ala Ile Ser Val Asp Thr Ser Lys Asn Gln Ile Ser Leu
65                  70                  75                  80

Asn Leu Lys Ser Val Thr Ala Ala Asp Thr Ala Met Tyr Tyr Cys Val
                85                  90                  95

Arg Ala Ser Arg Ala Tyr Leu Trp Gly Ser Tyr Arg Pro Thr Ala Leu
            100                 105                 110

Asp Leu Trp Gly Gln Gly Ser Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Ser Leu Gly Thr Gln Thr Tyr Ile Cys
        195                 200                 205

Asn Val Asn His Lys Pro Ser Asn Thr Lys Val Asp Lys Lys Val Glu
    210                 215                 220
```

```
Pro Lys Ser Cys Asp Lys Thr His Thr Cys Pro Pro Cys Pro Ala Pro
225                 230                 235                 240

Glu Leu Leu Gly Gly Pro Ser Val Phe Leu Phe Pro Pro Lys Pro Lys
            245                 250                 255

Asp Thr Leu Met Ile Ser Arg Thr Pro Glu Val Thr Cys Val Val Val
        260                 265                 270

Asp Val Ser His Glu Asp Pro Glu Val Lys Phe Asn Trp Tyr Val Asp
    275                 280                 285

Gly Val Glu Val His Asn Ala Lys Thr Lys Pro Arg Glu Glu Gln Tyr
290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Ala Leu
                325                 330                 335

Pro Ala Pro Ile Glu Lys Thr Ile Ser Lys Ala Lys Gly Gln Pro Arg
            340                 345                 350

Glu Pro Gln Val Tyr Thr Leu Pro Pro Ser Arg Asp Glu Leu Thr Lys
        355                 360                 365

Asn Gln Val Ser Leu Thr Cys Leu Val Lys Gly Phe Tyr Pro Ser Asp
370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Lys Leu Thr Val Asp Lys Ser Arg Trp Gln Gln Gly Asn Val Phe Ser
            420                 425                 430

Cys Ser Val Met His Glu Ala Leu His Asn His Tyr Thr Gln Lys Ser
        435                 440                 445

Leu Ser Leu Ser Pro Gly Lys
    450                 455

<210> SEQ ID NO 7
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 7

Gly Gly Ile Leu Ser Ser Phe Tyr
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 8

Ile Tyr Tyr Ser Gly Ser Pro
1               5

<210> SEQ ID NO 9
<211> LENGTH: 19
<212> TYPE: PRT
<213> ORGANISM: Artificial Sequence
<220> FEATURE:
<223> OTHER INFORMATION: Synthetic polypeptide
```

<400> SEQUENCE: 9

Val Arg Ala Ser Arg Ala Tyr Leu Trp Gly Ser Tyr Arg Pro Thr Ala
1               5                   10                  15
Leu Asp Leu

<210> SEQ ID NO 10
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 10

Lys Leu Gly Asp Lys Tyr
1               5

<210> SEQ ID NO 11
<211> LENGTH: 3
<212> TYPE: PRT
<213> ORGANISM: Artificial Sequence
<220> FEATURE:
<223> OTHER INFORMATION: Synthetic polypeptide

<400> SEQUENCE: 11

Gln Asp Asn
1

<210> SEQ ID NO 12
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 12

Gln Val Trp Asp Ser Gly Ala Val
1               5

<210> SEQ ID NO 13
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 13
atgggatggt catgtatcat ccttttttcta gtagcaactg caaccggtgt acattctcag    60
gtgcagctgc aggagtcggg accaggactg gtgaagcctt cggagaccct gtccctcacc   120
tgcgttgtct ctggtggcat cctcagtagt ttttactgga actggatccg gcagccccca   180
ggaaagggac tggagtggat tggaaacatc tattacagtg ggagccccaa ctataatgcc   240
tccttccaga gtcgagtcgc catttcggtg gacacgtcca agaaccagat ctccctgaac   300
ctcaagtctg tgaccgctgc ggacacggcc atgtattact gtgtgagagc ctcccgcgct   360
tacctttggg ggagttatcg tccaacggct cttgacctct ggggccaggg atccctggtc   420
accgtctcct ca                                                       432

<210> SEQ ID NO 14
<211> LENGTH: 372
<212> TYPE: DNA
<213> ORGANISM: Artificial Sequence
<220> FEATURE:

<223> OTHER INFORMATION: Synthetic polynucleotide

<400> SEQUENCE: 14

| | | |
|---|---|---|
| atgggatggt catgtatcat ccttttttcta gtagcaactg caaccggtgt ccatgcttcc | 60 |
| tatgagctga ctcagccacc ctcagtgtcc gtgtccccag acagacagc caccatcacg | 120 |
| tgctctggag ataaattggg tgataaatat acttcctggt ccagcagag gccaggccag | 180 |
| tcccctctac tggtcatcta tcaggataat aagcggccct cagggctccc tgcgcgattt | 240 |
| tctggctcca actctgggaa cacagccact ctgaccatca gcggcaccca ggctatggat | 300 |
| gaggctgact atttgtgtca ggtgtgggac agcggtgcgg tgttcggcgg agggaccaag | 360 |
| ctgaccgtcc ta | 372 |

<210> SEQ ID NO 15
<211> LENGTH: 432
<212> TYPE: DNA
<213> ORGANISM: Artificial Sequence
<220> FEATURE:
<223> OTHER INFORMATION: Synthetic polynucleotide

<400> SEQUENCE: 15

| | |
|---|---|
| atgggatggt catgtatcat ccttttttcta gtagcaactg caaccggtgt acattctcag | 60 |
| gtgcagctgc aggagtcggg accaggactg gtgaagcctt cggagaccct gtccctcacc | 120 |
| tgcgttgtct ctggtggcat cctcagtagt ttttactgga actggatccg gcagccccca | 180 |
| ggaaagggac tggagtggat tggaaacatc tattacagtg ggagccccaa ctataatccc | 240 |
| tccttccaga gtcgagtcgc catttcggtg gacacgtcca agaaccagat ctccctgaac | 300 |
| ctcaagtctg tgaccgctgc ggacacggcc atgtattact gtgtgagagc ctcccgcgct | 360 |
| tacctttggg ggagttatcg tccaacggct cttgacctct ggggccaggg atccctggtc | 420 |
| accgtctcct ca | 432 |

<210> SEQ ID NO 16
<211> LENGTH: 1425
<212> TYPE: DNA
<213> ORGANISM: Artificial Sequence
<220> FEATURE:
<223> OTHER INFORMATION: Synthetic nucleic acid

<400> SEQUENCE: 16

| | |
|---|---|
| atgggatggt catgtatcat ccttttttcta gtagcaactg caaccggtgt acattctcag | 60 |
| gtgcagctgc aggagtcggg accaggactg gtgaagcctt cggagaccct gtccctcacc | 120 |
| tgcgttgtct ctggtggcat cctcagtagt ttttactgga actggatccg gcagccccca | 180 |
| ggaaagggac tggagtggat tggaaacatc tattacagtg ggagccccaa ctataatgcc | 240 |
| tccttccaga gtcgagtcgc catttcggtg gacacgtcca agaaccagat ctccctgaac | 300 |
| ctcaagtctg tgaccgctgc ggacacggcc atgtattact gtgtgagagc ctcccgcgct | 360 |
| tacctttggg ggagttatcg tccaacggct cttgacctct ggggccaggg atccctggtc | 420 |
| accgtctcct cagcgtcgac caagggccca tcggtcttcc ccctggcacc ctcctccaag | 480 |
| agcacctctg ggggcacagc ggccctgggc tgcctggtca aggactactt ccccgaaccc | 540 |
| gtgacggtgt cgtggaactc aggcgccctg accagcggcg tgcacacctt cccggctgtc | 600 |
| ctacagtcct caggactcta ctccctcagc agcgtggtga ccgtgccctc agcagcttg | 660 |
| ggcacccaga cctacatctg caacgtgaat cacaagccca gcaacaccaa ggtggacaag | 720 |
| aaagttgagc ccaaatcttg tgacaaaact cacacatgcc caccgtgccc agcacctgaa | 780 |

```
ctcctgggggg  gaccgtcagt  cttcctcttc  cccccaaaac  ccaaggacac  cctcatgatc      840
tcccggaccc  ctgaggtcac  atgcgtggtg  gtggacgtga  gccacgaaga  ccctgaggtc      900
aagttcaact  ggtacgtgga  cggcgtggag  gtgcataatg  ccaagacaaa  gccgcgggag      960
gagcagtaca  acagcacgta  ccgtgtggtc  agcgtcctca  ccgtcctgca  ccaggactgg     1020
ctgaatggca  aggagtacaa  gtgcaaggtc  tccaacaaag  ccctcccagc  ccccatcgag     1080
aaaaccatct  ccaaagccaa  agggcagccc  cgagaaccac  aggtgtacac  cctgccccca     1140
tcccgggatg  agctgaccaa  gaaccaggtc  agcctgacct  gcctggtcaa  aggcttctat     1200
cccagcgaca  tcgccgtgga  gtgggagagc  aatgggcagc  cggagaacaa  ctacaagacc     1260
acgcctcccg  tgctggactc  cgacggctcc  ttcttcctct  acagcaagct  caccgtggac     1320
aagagcaggt  ggcagcaggg  gaacgtcttc  tcatgctccg  tgatgcatga  ggctctgcac     1380
aaccactaca  cgcagaagag  cctctccctg  tctccgggta  aatga                     1425
```

<210> SEQ ID NO 17
<211> LENGTH: 693
<212> TYPE: DNA
<213> ORGANISM: Artificial Sequence
<220> FEATURE:
<223> OTHER INFORMATION: Synthetic nucleic acid

<400> SEQUENCE: 17

```
atgggatggt  catgtatcat  cctttttcta  gtagcaactg  caaccggtgt  ccatgcttcc       60
tatgagctga  ctcagccacc  ctcagtgtcc  gtgtccccag  gacagacagc  caccatcacg      120
tgctctggag  ataaattggg  tgataaatat  acttcctggt  tccagcagag  gccaggccag      180
tcccctctac  tggtcatcta  tcaggataat  aagcggccct  cagggctccc  tgcgcgattt      240
tctggctcca  actctgggaa  cacagccact  ctgaccatca  gcggcaccca  ggctatggat      300
gaggctgact  atttgtgtca  ggtgtgggac  agcggtgcgg  tgttcggcgg  agggaccaag      360
ctgaccgtcc  taggtcagcc  caaggctgcc  ccctcggtca  ctctgttccc  accctcgagt      420
gaggagcttc  aagccaacaa  ggccacactg  gtgtgtctca  taagtgactt  ctacccggga      480
gccgtgacag  tggcctggaa  ggcagatagc  agccccgtca  aggcgggagt  ggagaccacc      540
acaccctcca  aacaaagcaa  caacaagtac  gcggccagca  gctacctgag  cctgacgcct      600
gagcagtgga  agtcccacag  aagctacagc  tgccaggtca  cgcatgaagg  gagcaccgtg      660
gagaagacag  tggcccctac  agaatgttca  tag                                    693
```

<210> SEQ ID NO 18
<211> LENGTH: 1425
<212> TYPE: DNA
<213> ORGANISM: Artificial Sequence
<220> FEATURE:
<223> OTHER INFORMATION: Synthetic nucleic acid

<400> SEQUENCE: 18

```
atgggatggt  catgtatcat  cctttttcta  gtagcaactg  caaccggtgt  acattctcag       60
gtgcagctgc  aggagtcggg  accaggactg  gtgaagcctt  cggagaccct  gtccctcacc      120
tgcgttgtct  ctggtggcat  cctcagtagt  ttttactgga  actggatccg  gcagccccca      180
ggaaagggac  tggagtggat  tggaaacatc  tattacagtg  ggagccccaa  ctataatccc      240
tccttccaga  gtcgagtcgc  catttcggtg  gacacgtcca  agaaccagat  ctccctgaac      300
ctcaagtctg  tgaccgctgc  ggacacggcc  atgtattact  gtgtgagagc  ctcccgcgct      360
```

```
taccctttggg ggagttatcg tccaacggct cttgacctct ggggccaggg atccctggtc    420
accgtctcct cagcgtcgac caagggccca tcggtcttcc ccctggcacc ctcctccaag    480
agcacctctg ggggcacagc ggccctgggc tgcctggtca aggactactt ccccgaaccc    540
gtgacggtgt cgtggaactc aggcgccctg accagcggcg tgcacacctt ccggctgtc     600 ctacagtcct caggactcta ctccctcagc agcgtggtga ccgtgccctc agcagcttg     660 ggcacccaga cctacatctg caacgtgaat cacaagccca gcaacaccaa ggtggacaag    720
aaagttgagc ccaaatcttg tgacaaaact cacacatgcc caccgtgccc agcacctgaa    780
ctcctggggg gaccgtcagt cttcctcttc cccccaaaac ccaaggacac cctcatgatc    840
tcccggaccc ctgaggtcac atgcgtggtg gtggacgtga gccacgaaga ccctgaggtc    900
aagttcaact ggtacgtgga cggcgtggag gtgcataatg ccaagacaaa gccgcgggag    960
gagcagtaca acagcacgta ccgtgtggtc agcgtcctca ccgtcctgca ccaggactgg   1020
ctgaatggca aggagtacaa gtgcaaggtc tccaacaaag ccctcccagc ccccatcgag   1080
aaaaccatct ccaaagccaa agggcagccc cgagaaccac aggtgtacac cctgccccca   1140
tcccgggatg agctgaccaa gaaccaggtc agcctgacct gcctggtcaa aggcttctat   1200
cccagcgaca tcgccgtgga gtgggagagc aatgggcagc cggagaacaa ctacaagacc   1260
acgcctcccg tgctggactc cgacggctcc ttcttcctct acagcaagct caccgtggac   1320
aagagcaggt ggcagcaggg gaacgtcttc tcatgctccg tgatgcatga ggctctgcac   1380
aaccactaca cgcagaagag cctctccctg tctccgggta aatga                   1425

<210> SEQ ID NO 19
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 19

Met Gly Trp Ser Cys Ile Ile Leu Phe Leu Val Ala Thr Ala Thr Gly
1               5                   10                  15

Val His Ser

<210> SEQ ID NO 20
<211> LENGTH: 19
<212> TYPE: PRT
<213> ORGANISM: Artificial Sequence
<220> FEATURE:
<223> OTHER INFORMATION: Synthetic polypeptide

<400> SEQUENCE: 20

Met Gly Trp Ser Cys Ile Ile Leu Phe Leu Val Ala Thr Ala Thr Gly
1               5                   10                  15

Val His Ala

<210> SEQ ID NO 21
<211> LENGTH: 119
<212> TYPE: PRT
<213> ORGANISM: Artificial Sequence
<220> FEATURE:
<223> OTHER INFORMATION: Synthetic polypeptide

<400> SEQUENCE: 21

Glu Val Gln Leu Val Glu Ser Gly Gly Gly Leu Ile Gln Pro Gly Gly
1               5                   10                  15
```

```
Ser Leu Arg Leu Ser Cys Ala Ala Ser Gly Phe Ala Leu Arg Met Tyr
            20                  25                  30

Asp Met His Trp Val Arg Gln Thr Ile Asp Lys Arg Leu Glu Trp Val
        35                  40                  45

Ser Ala Val Gly Pro Ser Gly Asp Thr Tyr Tyr Ala Asp Ser Val Lys
 50                  55                  60

Gly Arg Phe Ala Val Ser Arg Glu Asn Ala Lys Asn Ser Leu Ser Leu
 65                  70                  75                  80

Gln Met Asn Ser Leu Thr Ala Gly Asp Thr Ala Ile Tyr Tyr Cys Val
                85                  90                  95

Arg Ser Asp Arg Gly Val Ala Gly Leu Phe Asp Ser Trp Gly Gln Gly
                100                 105                 110

Ile Leu Val Thr Val Ser Ser
            115
```

```
<210> SEQ ID NO 22
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 22

Asp Ile Gln Met Thr Gln Ser Pro Ser Ser Leu Ser Ala Ser Val Gly
 1               5                  10                  15

Asp Arg Ile Thr Ile Thr Cys Arg Ala Ser Gln Ala Phe Asp Asn Tyr
            20                  25                  30

Val Ala Trp Tyr Gln Gln Arg Pro Gly Lys Val Pro Lys Leu Leu Ile
        35                  40                  45

Ser Ala Ala Ser Ala Leu His Ala Gly Val Pro Ser Arg Phe Ser Gly
 50                  55                  60

Ser Gly Ser Gly Thr His Phe Thr Leu Thr Ile Ser Ser Leu Gln Pro
 65                  70                  75                  80

Glu Asp Val Ala Thr Tyr Tyr Cys Gln Asn Tyr Asn Ser Ala Pro Leu
                85                  90                  95

Thr Phe Gly Gly Gly Thr Lys Val Glu Ile Lys
                100                 105
```

```
<210> SEQ ID NO 23
<211> LENGTH: 125
<212> TYPE: PRT
<213> ORGANISM: Artificial Sequence
<220> FEATURE:
<223> OTHER INFORMATION: Synthetic polypeptide

<400> SEQUENCE: 23

Gln Val Gln Leu Gln Glu Ser Gly Pro Gly Leu Val Lys Pro Ser Asp
 1               5                  10                  15

Thr Leu Ser Leu Thr Cys Thr Val Ser Gly Gly Ser Leu Ser Ser Phe
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Pro Asn Tyr Ser Pro Ser Leu Glu
 50                  55                  60

Ser Arg Val Thr Met Ser Val Asp Thr Thr Arg Asn Gln Ile Ser Leu
 65                  70                  75                  80

Lys Leu Asp Ser Val Thr Ala Ala Asp Thr Ala Val Tyr Tyr Cys Val
                85                  90                  95
```

```
Arg Ala Ser Arg Ser Tyr Tyr Trp Gly Ser Tyr Arg Pro Thr Ala Phe
                100                 105                 110
Asp Ser Trp Gly Gln Gly Thr Leu Val Thr Val Ser Ser
            115                 120                 125

<210> SEQ ID NO 24
<211> LENGTH: 105
<212> TYPE: PRT
<213> ORGANISM: Artificial Sequence
<220> FEATURE:
<223> OTHER INFORMATION: Synthetic polypeptide

<400> SEQUENCE: 24

Ser Tyr Glu Leu Thr Gln Pro Leu Ser Val Ser Val Ser Pro Gly Gln
1               5                   10                  15
Thr Ala Ile Phe Thr Cys Ser Gly Asp Asn Leu Gly Asp Lys Tyr Val
            20                  25                  30
Cys Trp Phe Gln Gln Arg Pro Gly Gln Ser Pro Met Leu Leu Ile Tyr
        35                  40                  45
Gln Asp Asn Lys Arg Pro Ser Gly Ile Pro Glu Arg Phe Ser Gly Ser
    50                  55                  60
Asn Ser Gly Asn Thr Ala Thr Leu Thr Ile Ser Gly Thr Gln Ser Thr
65                  70                  75                  80
Asp Glu Ala Asp Tyr Tyr Cys Gln Thr Trp Asp Ser Thr Val Val Phe
                85                  90                  95
Gly Gly Gly Thr Lys Leu Thr Val Leu
            100                 105

<210> SEQ ID NO 25
<211> LENGTH: 676
<212> TYPE: PRT
<213> ORGANISM: Bundibugyo ebolavirus

<400> SEQUENCE: 25

Met Val Thr Ser Gly Ile Leu Gln Leu Pro Arg Glu Arg Phe Arg Lys
1               5                   10                  15
Thr Ser Phe Phe Val Trp Val Ile Ile Leu Phe His Lys Val Phe Pro
            20                  25                  30
Ile Pro Leu Gly Val Val His Asn Asn Thr Leu Gln Val Ser Asp Ile
        35                  40                  45
Asp Lys Leu Val Cys Arg Asp Lys Leu Ser Ser Thr Ser Gln Leu Lys
    50                  55                  60
Ser Val Gly Leu Asn Leu Glu Gly Asn Gly Val Ala Thr Asp Val Pro
65                  70                  75                  80
Thr Ala Thr Lys Arg Trp Gly Phe Arg Ala Gly Val Pro Pro Lys Val
                85                  90                  95
Val Asn Tyr Glu Ala Gly Glu Trp Ala Glu Asn Cys Tyr Asn Leu Asp
            100                 105                 110
Ile Lys Lys Ala Asp Gly Ser Glu Cys Leu Pro Glu Ala Pro Glu Gly
        115                 120                 125
Val Arg Gly Phe Pro Arg Cys Arg Tyr Val His Lys Val Ser Gly Thr
    130                 135                 140
Gly Pro Cys Pro Glu Gly Tyr Ala Phe His Lys Glu Gly Ala Phe Phe
145                 150                 155                 160
Leu Tyr Asp Arg Leu Ala Ser Thr Ile Ile Tyr Arg Ser Thr Thr Phe
                165                 170                 175
```

```
Ser Glu Gly Val Val Ala Phe Leu Ile Leu Pro Glu Thr Lys Lys Asp
            180                 185                 190

Phe Phe Gln Ser Pro Pro Leu His Glu Pro Ala Asn Met Thr Thr Asp
        195                 200                 205

Pro Ser Ser Tyr Tyr His Thr Val Thr Leu Asn Tyr Val Ala Asp Asn
        210                 215                 220

Phe Gly Thr Asn Met Thr Asn Phe Leu Phe Gln Val Asp His Leu Thr
225                 230                 235                 240

Tyr Val Gln Leu Glu Pro Arg Phe Thr Pro Gln Phe Leu Val Gln Leu
                245                 250                 255

Asn Glu Thr Ile Tyr Thr Asn Gly Arg Arg Ser Asn Thr Thr Gly Thr
                260                 265                 270

Leu Ile Trp Lys Val Asn Pro Thr Val Asp Thr Gly Val Gly Glu Trp
            275                 280                 285

Ala Phe Trp Glu Asn Lys Lys Asn Phe Thr Lys Thr Leu Ser Ser Glu
290                 295                 300

Glu Leu Ser Val Ile Phe Val Pro Arg Ala Gln Asp Pro Gly Ser Asn
305                 310                 315                 320

Gln Lys Thr Lys Val Thr Pro Thr Ser Phe Ala Asn Asn Gln Thr Ser
                325                 330                 335

Lys Asn His Glu Asp Leu Val Pro Glu Asp Pro Ala Ser Val Val Gln
            340                 345                 350

Val Arg Asp Leu Gln Arg Glu Asn Thr Val Pro Thr Pro Pro Pro Asp
            355                 360                 365

Thr Val Pro Thr Thr Leu Ile Pro Asp Thr Met Glu Glu Gln Thr Thr
370                 375                 380

Ser His Tyr Glu Pro Pro Asn Ile Ser Arg Asn His Gln Glu Arg Asn
385                 390                 395                 400

Asn Thr Ala His Pro Glu Thr Leu Ala Asn Asn Pro Pro Asp Asn Thr
                405                 410                 415

Thr Pro Ser Thr Pro Pro Gln Asp Gly Glu Arg Thr Ser Ser His Thr
            420                 425                 430

Thr Pro Ser Pro Arg Pro Val Pro Thr Ser Thr Ile His Pro Thr Thr
            435                 440                 445

Arg Glu Thr His Ile Pro Thr Thr Met Thr Thr Ser His Asp Thr Asp
450                 455                 460

Ser Asn Arg Pro Asn Pro Ile Asp Ile Ser Glu Ser Thr Glu Pro Gly
465                 470                 475                 480

Pro Leu Thr Asn Thr Thr Arg Gly Ala Ala Asn Leu Leu Thr Gly Ser
                485                 490                 495

Arg Arg Thr Arg Arg Glu Ile Thr Leu Arg Thr Gln Ala Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
530                 535                 540

Glu Gly Ile Met His Asn Gln Asn Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
```

```
                    595                 600                 605
Cys Ile Glu Pro His Asp Trp Thr Lys Asn Ile Thr Asp Lys Ile Asp
    610                 615                 620
Gln Ile Ile His Asp Phe Ile Asp Lys Pro Leu Pro Asp Gln Thr Asp
625                 630                 635                 640
Asn Asp Asn Trp Trp Thr Gly Trp Arg Gln Trp Val Pro Ala Gly Ile
                645                 650                 655
Gly Ile Thr Gly Val Ile Ile Ala Val Ile Ala Leu Leu Cys Ile Cys
                660                 665                 670
Lys Phe Leu Leu
        675

<210> SEQ ID NO 26
<211> LENGTH: 676
<212> TYPE: PRT
<213> ORGANISM: Sudan ebolavirus

<400> SEQUENCE: 26

Met Glu Gly Leu Ser Leu Leu Gln Leu Pro Arg Asp Lys Phe Arg Lys
1               5                   10                  15
Ser Ser Phe Phe Val Trp Val Ile Ile Leu Phe Gln Lys Ala Phe Ser
                20                  25                  30
Met Pro Leu Gly Val Val Thr Asn Ser Thr Leu Glu Val Thr Glu Ile
            35                  40                  45
Asp Gln Leu Val Cys Lys Asp His Leu Ala Ser Thr Asp Gln Leu Lys
        50                  55                  60
Ser Val Gly Leu Asn Leu Glu Gly Ser Gly Val Ser Thr Asp Ile Pro
65                  70                  75                  80
Ser Ala Thr Lys Arg Trp Gly Phe Arg Ser Gly Val Pro Pro Lys Val
                85                  90                  95
Phe Ser Tyr Glu Ala Gly Glu Trp Ala Glu Asn Cys Tyr Asn Leu Glu
                100                 105                 110
Ile Lys Lys Pro Asp Gly Ser Glu Cys Leu Pro Pro Pro Asp Gly
            115                 120                 125
Val Arg Gly Phe Pro Arg Cys Arg Tyr Val His Lys Ala Gln Gly Thr
        130                 135                 140
Gly Pro Cys Pro Gly Asp Tyr Ala Phe His Lys Asp Gly Ala Phe Phe
145                 150                 155                 160
Leu Tyr Asp Arg Leu Ala Ser Thr Val Ile Tyr Arg Gly Val Asn Phe
                165                 170                 175
Ala Glu Gly Val Ile Ala Phe Leu Ile Leu Ala Lys Pro Lys Glu Thr
                180                 185                 190
Phe Leu Gln Ser Pro Pro Ile Arg Glu Ala Val Asn Tyr Thr Glu Asn
            195                 200                 205
Thr Ser Ser Tyr Tyr Ala Thr Ser Tyr Leu Glu Tyr Glu Ile Glu Asn
        210                 215                 220
Phe Gly Ala Gln His Ser Thr Thr Leu Phe Lys Ile Asn Asn Asn Thr
225                 230                 235                 240
Phe Val Leu Leu Asp Arg Pro His Thr Pro Gln Phe Leu Phe Gln Leu
                245                 250                 255
Asn Asp Thr Ile His Leu His Gln Gln Leu Ser Asn Thr Thr Gly Lys
                260                 265                 270
Leu Ile Trp Thr Leu Asp Ala Asn Ile Asn Ala Asp Ile Gly Glu Trp
            275                 280                 285
```

Ala Phe Trp Glu Asn Lys Lys Asn Leu Ser Glu Gln Leu Arg Gly Glu
            290                 295                 300

Glu Leu Ser Phe Glu Thr Leu Ser Leu Asn Glu Thr Glu Asp Asp Asp
305                 310                 315                 320

Ala Thr Ser Ser Arg Thr Thr Lys Gly Arg Ile Ser Asp Arg Ala Thr
                325                 330                 335

Arg Lys Tyr Ser Asp Leu Val Pro Lys Asp Ser Pro Gly Met Val Ser
            340                 345                 350

Leu His Val Pro Glu Gly Glu Thr Leu Pro Ser Gln Asn Ser Thr
        355                 360                 365

Glu Gly Arg Arg Val Asp Val Asn Thr Gln Glu Thr Ile Thr Glu Thr
370                 375                 380

Thr Ala Thr Ile Ile Gly Thr Asn Gly Asn Asn Met Gln Ile Ser Thr
385                 390                 395                 400

Ile Gly Thr Gly Leu Ser Ser Ser Gln Ile Leu Ser Ser Ser Pro Thr
                405                 410                 415

Met Ala Pro Ser Pro Glu Thr Gln Thr Ser Thr Thr Tyr Thr Pro Lys
            420                 425                 430

Leu Pro Val Met Thr Thr Glu Glu Ser Thr Thr Pro Arg Asn Ser
        435                 440                 445

Pro Gly Ser Thr Thr Glu Ala Pro Thr Leu Thr Thr Pro Glu Asn Ile
450                 455                 460

Thr Thr Ala Val Lys Thr Val Leu Pro Gln Glu Ser Thr Ser Asn Gly
465                 470                 475                 480

Leu Ile Thr Ser Thr Val Thr Gly Ile Leu Gly Ser Leu Gly Leu Arg
                485                 490                 495

Lys Arg Ser Arg Arg Gln Val Asn Thr Arg Ala Thr Gly Lys Cys Asn
            500                 505                 510

Pro Asn Leu His Tyr Trp Thr Ala Gln Glu Gln His Asn Ala Ala Gly
        515                 520                 525

Ile Ala Trp Ile Pro Tyr Phe Gly Pro Gly Ala Glu Gly Ile Tyr Thr
530                 535                 540

Glu Gly Leu Met His Asn Gln Asn Ala Leu Val Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Tyr Thr Ile Leu Asn Arg Lys Ala Ile Asp Phe
            580                 585                 590

Leu Leu Arg Arg Trp Gly Gly Thr Cys Arg Ile Leu Gly Pro Asp Cys
        595                 600                 605

Cys Ile Glu Pro His Asp Trp Thr Lys Asn Ile Thr Asp Lys Ile Asn
610                 615                 620

Gln Ile Ile His Asp Phe Ile Asp Asn Pro Leu Pro Asn Gln Asp Asn
625                 630                 635                 640

Asp Asp Asn Trp Trp Thr Gly Trp Arg Gln Trp Ile Pro Ala Gly Ile
                645                 650                 655

Gly Ile Thr Gly Ile Ile Ile Ala Ile Ile Ala Leu Leu Cys Val Cys
            660                 665                 670

Lys Leu Leu Cys
        675

<210> SEQ ID NO 27
<211> LENGTH: 676
<212> TYPE: PRT

<213> ORGANISM: Zaire ebolavirus

<400> SEQUENCE: 27

```
Met Gly Val Thr Gly Ile Leu Gln Leu Pro Arg Asp Arg Phe Lys Lys
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
    50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
    130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
    210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Asn Leu Thr Arg Lys Ile Arg Ser Glu
    290                 295                 300

Glu Leu Ser Phe Thr Ala Val Ser Asn Arg Ala Lys Asn Ile Ser Gly
305                 310                 315                 320

Gln Ser Pro Ala Arg Thr Ser Ser Asp Pro Gly Thr Asn Thr Thr Thr
                325                 330                 335

Glu Asp His Lys Ile Met Ala Ser Glu Asn Ser Ser Ala Met Val Gln
            340                 345                 350

Val His Ser Gln Gly Arg Glu Ala Ala Val Ser His Leu Thr Thr Leu
        355                 360                 365

Ala Thr Ile Ser Thr Ser Pro Gln Pro Pro Thr Thr Lys Pro Gly Pro
    370                 375                 380

Asp Asn Ser Thr His Asn Thr Pro Val Tyr Lys Leu Asp Ile Ser Glu
385                 390                 395                 400
```

Ala Thr Gln Ala Glu Gln His His Arg Arg Thr Asp Asn Asp Ser Thr
                405                 410                 415

Thr Ser Asp Thr Pro Pro Ala Met Thr Ala Ala Gly Pro Pro Lys Ala
            420                 425                 430

Glu Asn Thr Asn Thr Ser Lys Gly Thr Asp Leu Pro Asp Pro Ala Thr
            435                 440                 445

Thr Thr Ser Pro Gln Asn His Ser Glu Thr Ala Gly Asn Asn Asn Thr
        450                 455                 460

His His Gln Asp Thr Gly Glu Glu Ser Ala Ser Gly Lys Leu Gly
465                 470                 475                 480

Leu Ile Thr Asn Thr Ile Ala Gly Val Ala Gly Leu Ile Thr Gly Gly
                485                 490                 495

Arg Arg Thr Arg Arg Glu Ala Ile Val Asn Ala Gln Pro Lys Cys Asn
            500                 505                 510

Pro Asn Leu His Tyr Trp Thr Thr Gln Asp Glu Gly Ala Ala Ile Gly
            515                 520                 525

Leu Ala Trp Ile Pro Tyr Phe Gly Pro Ala Ala Glu Gly Ile Tyr Thr
        530                 535                 540

Glu Gly Leu Met His Asn Gln Asp Gly Leu Ile Cys Gly Leu Arg Gln
545                 550                 555                 560

Leu Ala Asn Glu Thr Thr Gln Ala Leu Gln Leu Phe Leu Arg Ala Thr
                565                 570                 575

Thr Glu Leu Arg Thr Phe Ser Ile Leu Asn Arg Lys Ala Ile Asp Phe
            580                 585                 590

Leu Leu Gln Arg Trp Gly Gly Thr Cys His Ile Leu Gly Pro Asp Cys
        595                 600                 605

Cys Ile Glu Pro His Asp Trp Thr Lys Asn Ile Thr Asp Lys Ile Asp
610                 615                 620

Gln Ile Ile His Asp Phe Val Asp Lys Thr Leu Pro Asp Gln Gly Asp
625                 630                 635                 640

Asn Asp Asn Trp Trp Thr Gly Trp Arg Gln Trp Ile Pro Ala Gly Ile
                645                 650                 655

Gly Val Thr Gly Val Ile Ile Ala Val Ile Ala Leu Phe Cys Ile Cys
            660                 665                 670

Lys Phe Val Phe
        675

<210> SEQ ID NO 28
<211> LENGTH: 677
<212> TYPE: PRT
<213> ORGANISM: Reston ebolavirus

<400> SEQUENCE: 28

Met Gly Ser Gly Tyr Gln Leu Leu Gln Leu Pro Arg Glu Arg Phe Arg
1               5                   10                  15

Lys Thr Ser Phe Leu Val Trp Val Ile Ile Leu Phe Gln Arg Ala Ile
            20                  25                  30

Ser Met Pro Leu Gly Ile Val Thr Asn Ser Thr Leu Lys Ala Thr Glu
        35                  40                  45

Ile Asp Gln Leu Val Cys Arg Asp Lys Leu Ser Ser Thr Ser Gln Leu
    50                  55                  60

Lys Ser Val Gly Leu Asn Leu Glu Gly Asn Gly Ile Ala Thr Asp Val
65                  70                  75                  80

Pro Ser Ala Thr Lys Arg Trp Gly Phe Arg Ser Gly Val Pro Pro Lys
                85                  90                  95

```
Val Val Ser Tyr Glu Ala Gly Glu Trp Ala Glu Asn Cys Tyr Asn Leu
            100                 105                 110
Glu Ile Lys Lys Ser Asp Gly Ser Glu Cys Leu Pro Leu Pro Pro Asp
            115                 120                 125
Gly Val Arg Gly Phe Pro Arg Cys Arg Tyr Val His Lys Val Gln Gly
        130                 135                 140
Thr Gly Pro Cys Pro Gly Asp Leu Ala Phe His Lys Asn Gly Ala Phe
145                 150                 155                 160
Phe Leu Tyr Asp Arg Leu Ala Ser Thr Val Ile Tyr Arg Gly Thr Thr
                165                 170                 175
Phe Thr Glu Gly Val Val Ala Phe Leu Ile Leu Ser Glu Pro Lys Lys
            180                 185                 190
His Phe Trp Lys Ala Thr Pro Ala His Glu Pro Val Asn Thr Thr Asp
            195                 200                 205
Asp Ser Thr Ser Tyr Tyr Met Thr Leu Thr Leu Ser Tyr Glu Met Ser
        210                 215                 220
Asn Phe Gly Gly Lys Glu Ser Asn Thr Leu Phe Lys Val Asp Asn His
225                 230                 235                 240
Thr Tyr Val Gln Leu Asp Arg Pro His Thr Pro Gln Phe Leu Val Gln
                245                 250                 255
Leu Asn Glu Thr Leu Arg Arg Asn Asn Arg Leu Ser Asn Ser Thr Gly
            260                 265                 270
Arg Leu Thr Trp Thr Leu Asp Pro Lys Ile Glu Pro Asp Val Gly Glu
        275                 280                 285
Trp Ala Phe Trp Glu Thr Lys Lys Asn Phe Ser Gln Gln Leu His Gly
        290                 295                 300
Glu Asn Leu His Phe Gln Ile Leu Ser Thr His Thr Asn Asn Ser Ser
305                 310                 315                 320
Asp Gln Ser Pro Ala Gly Thr Val Gln Gly Lys Ile Ser Tyr His Pro
                325                 330                 335
Pro Thr Asn Asn Ser Glu Leu Val Pro Thr Asp Ser Pro Pro Val Val
            340                 345                 350
Ser Val Leu Thr Ala Gly Arg Thr Glu Glu Met Ser Thr Gln Gly Leu
        355                 360                 365
Thr Asn Gly Glu Thr Ile Thr Gly Phe Thr Ala Asn Pro Met Thr Thr
        370                 375                 380
Thr Ile Ala Pro Ser Pro Thr Met Thr Ser Glu Val Asp Asn Asn Val
385                 390                 395                 400
Pro Ser Glu Gln Pro Asn Asn Thr Ala Ser Ile Glu Asp Ser Pro Pro
                405                 410                 415
Ser Ala Ser Asn Glu Thr Ile Asp His Ser Glu Met Asn Pro Ile Gln
            420                 425                 430
Gly Ser Asn Asn Ser Ala Gln Ser Pro Gln Thr Lys Thr Thr Pro Ala
        435                 440                 445
Pro Thr Ala Ser Pro Met Thr Gln Asp Pro Gln Glu Thr Ala Asn Ser
        450                 455                 460
Ser Lys Leu Gly Thr Ser Pro Gly Ser Ala Ala Glu Pro Ser Gln Pro
465                 470                 475                 480
Gly Phe Thr Ile Asn Thr Val Ser Lys Val Ala Asp Ser Leu Ser Pro
                485                 490                 495
Thr Arg Lys Gln Lys Arg Ser Val Arg Gln Asn Thr Ala Asn Lys Cys
            500                 505                 510
```

```
Asn Pro Asp Leu His Tyr Trp Thr Ala Val Asp Glu Gly Ala Ala Val
            515                 520                 525

Gly Leu Ala Trp Ile Pro Tyr Phe Gly Pro Ala Ala Glu Gly Ile Tyr
530                 535                 540

Ile Glu Gly Val Met His Asn Gln Asn Gly Leu Ile Cys Gly Leu Arg
545                 550                 555                 560

Gln Leu Ala Asn Glu Thr Thr Gln Ala Leu Gln Leu Phe Leu Arg Ala
                565                 570                 575

Thr Thr Glu Leu Arg Thr Tyr Ser Leu Leu Asn Arg Lys Ala Ile Asp
            580                 585                 590

Phe Leu Leu Gln Arg Trp Gly Gly Thr Cys Arg Ile Leu Gly Pro Ser
        595                 600                 605

Cys Cys Ile Glu Pro His Asp Trp Thr Lys Asn Ile Thr Asp Glu Ile
    610                 615                 620

Asn Gln Ile Lys His Asp Phe Ile Asp Asn Pro Leu Pro Asp His Gly
625                 630                 635                 640

Asp Asp Leu Asn Leu Trp Thr Gly Trp Arg Gln Trp Ile Pro Ala Gly
                645                 650                 655

Ile Gly Ile Ile Gly Val Ile Ile Ala Ile Ile Ala Leu Leu Cys Ile
            660                 665                 670

Cys Lys Ile Leu Cys
        675

<210> SEQ ID NO 29
<211> LENGTH: 676
<212> TYPE: PRT
<213> ORGANISM: Tai Forest ebolavirus

<400> SEQUENCE: 29

Met Gly Ala Ser Gly Ile Leu Gln Leu Pro Arg Glu Arg Phe Arg Lys
1               5                   10                  15

Thr Ser Phe Phe Val Trp Val Ile Ile Leu Phe His Lys Val Phe Ser
            20                  25                  30

Ile Pro Leu Gly Val Val His Asn Asn Thr Leu Gln Val Ser Asp Ile
        35                  40                  45

Asp Lys Phe Val Cys Arg Asp Lys Leu Ser Ser Thr Ser Gln Leu Lys
    50                  55                  60

Ser Val Gly Leu Asn Leu Glu Gly Asn Gly Val Ala Thr Asp Val Pro
65                  70                  75                  80

Thr Ala Thr Lys Arg Trp Gly Phe Arg Ala Gly Val Pro Pro Lys Val
                85                  90                  95

Val Asn Cys Glu Ala Gly Glu Trp Ala Glu Asn Cys Tyr Asn Leu Ala
            100                 105                 110

Ile Lys Lys Val Asp Gly Ser Glu Cys Leu Pro Glu Ala Pro Glu Gly
        115                 120                 125

Val Arg Asp Phe Pro Arg Cys Arg Tyr Val His Lys Val Ser Gly Thr
    130                 135                 140

Gly Pro Cys Pro Gly Gly Leu Ala Phe His Lys Glu Gly Ala Phe Phe
145                 150                 155                 160

Leu Tyr Asp Arg Leu Ala Ser Thr Ile Ile Tyr Arg Gly Thr Thr Phe
                165                 170                 175

Ala Glu Gly Val Ile Ala Phe Leu Ile Leu Pro Lys Ala Arg Lys Asp
            180                 185                 190

Phe Phe Gln Ser Pro Pro Leu His Glu Pro Ala Asn Met Thr Thr Asp
        195                 200                 205
```

```
Pro Ser Ser Tyr Tyr His Thr Thr Ile Asn Tyr Val Asp Asn
    210             215             220
Phe Gly Thr Asn Thr Thr Glu Phe Leu Phe Gln Val Asp His Leu Thr
225             230             235             240
Tyr Val Gln Leu Glu Ala Arg Phe Thr Pro Gln Phe Leu Val Leu Leu
            245             250             255
Asn Glu Thr Ile Tyr Ser Asp Asn Arg Arg Ser Asn Thr Thr Gly Lys
        260             265             270
Leu Ile Trp Lys Ile Asn Pro Thr Val Asp Thr Ser Met Gly Glu Trp
        275             280             285
Ala Phe Trp Glu Asn Lys Lys Asn Phe Thr Lys Thr Leu Ser Ser Glu
290             295             300
Glu Leu Ser Phe Val Pro Val Pro Glu Thr Gln Asn Gln Val Leu Asp
305             310             315             320
Thr Thr Ala Thr Val Ser Pro Pro Ile Ser Ala His Asn His Ala Ala
            325             330             335
Glu Asp His Lys Glu Leu Val Ser Glu Asp Ser Thr Pro Val Val Gln
        340             345             350
Met Gln Asn Ile Lys Gly Lys Asp Thr Met Pro Thr Thr Val Thr Gly
        355             360             365
Val Pro Thr Thr Thr Pro Ser Pro Phe Pro Ile Asn Ala Arg Asn Thr
370             375             380
Asp His Thr Lys Ser Phe Ile Gly Leu Glu Gly Pro Gln Glu Asp His
385             390             395             400
Ser Thr Thr Gln Pro Ala Lys Thr Thr Ser Gln Pro Thr Asn Ser Thr
            405             410             415
Glu Ser Thr Thr Leu Asn Pro Thr Ser Glu Pro Ser Ser Arg Gly Thr
        420             425             430
Gly Pro Ser Ser Pro Thr Val Pro Asn Thr Thr Glu Ser His Ala Glu
        435             440             445
Leu Gly Lys Thr Thr Pro Thr Thr Leu Pro Glu Gln His Thr Ala Ala
    450             455             460
Ser Ala Ile Pro Arg Ala Val His Pro Asp Glu Leu Ser Gly Pro Gly
465             470             475             480
Phe Leu Thr Asn Thr Ile Arg Gly Val Thr Asn Leu Leu Thr Gly Ser
            485             490             495
Arg Arg Lys Arg Arg Asp Val Thr Pro Asn Thr Gln Pro Lys Cys Asn
        500             505             510
Pro Asn Leu His Tyr Trp Thr Ala Leu Asp Glu Gly Ala Ala Ile Gly
        515             520             525
Leu Ala Trp Ile Pro Tyr Phe Gly Pro Ala Ala Glu Gly Ile Tyr Thr
    530             535             540
Glu Gly Ile Met Glu Asn Gln Asn Gly Leu Ile Cys Gly Leu Arg Gln
545             550             555             560
Leu Ala Asn Glu Thr Thr Gln Ala Leu Gln Leu Phe Leu Arg Ala Thr
            565             570             575
Thr Glu Leu Arg Thr Phe Ser Ile Leu Asn Arg Lys Ala Ile Asp Phe
        580             585             590
Leu Leu Gln Arg Trp Gly Gly Thr Cys His Ile Leu Gly Pro Asp Cys
        595             600             605
Cys Ile Glu Pro Gln Asp Trp Thr Lys Asn Ile Thr Asp Lys Ile Asp
    610             615             620
```

```
Gln Ile Ile His Asp Phe Val Asp Asn Asn Leu Pro Asn Gln Asn Asp
625                 630                 635                 640

Gly Ser Asn Trp Trp Thr Gly Trp Lys Gln Trp Val Pro Ala Gly Ile
            645                 650                 655

Gly Ile Thr Gly Val Ile Ile Ala Ile Ile Ala Leu Leu Cys Ile Cys
        660                 665                 670

Lys Phe Met Leu
        675

<210> SEQ ID NO 30
<211> LENGTH: 364
<212> TYPE: PRT
<213> ORGANISM: Zaire ebolavirus

<400> SEQUENCE: 30

Met Gly Val Thr Gly Ile Leu Gln Leu Pro Arg Asp Arg Phe Lys Arg
1               5                   10                  15

Thr Ser Phe Phe Leu Trp Val Ile Ile Leu Phe Gln Arg Thr Phe Ser
            20                  25                  30

Ile Pro Leu Gly Val Ile His Asn Ser Thr Leu Gln Val Ser Asp Val
        35                  40                  45

Asp Lys Leu Val Cys Arg Asp Lys Leu Ser Ser Thr Asn Gln Leu Arg
50                  55                  60

Ser Val Gly Leu Asn Leu Glu Gly Asn Gly Val Ala Thr Asp Val Pro
65                  70                  75                  80

Ser Ala Thr Lys Arg Trp Gly Phe Arg Ser Gly Val Pro Pro Lys Val
                85                  90                  95

Val Asn Tyr Glu Ala Gly Glu Trp Ala Glu Asn Cys Tyr Asn Leu Glu
            100                 105                 110

Ile Lys Lys Pro Asp Gly Ser Glu Cys Leu Pro Ala Ala Pro Asp Gly
        115                 120                 125

Ile Arg Gly Phe Pro Arg Cys Arg Tyr Val His Lys Val Ser Gly Thr
130                 135                 140

Gly Pro Cys Ala Gly Asp Phe Ala Phe His Lys Glu Gly Ala Phe Phe
145                 150                 155                 160

Leu Tyr Asp Arg Leu Ala Ser Thr Val Ile Tyr Arg Gly Thr Thr Phe
                165                 170                 175

Ala Glu Gly Val Val Ala Phe Leu Ile Leu Pro Gln Ala Lys Lys Asp
            180                 185                 190

Phe Phe Ser Ser His Pro Leu Arg Glu Pro Val Asn Ala Thr Glu Asp
        195                 200                 205

Pro Ser Ser Gly Tyr Tyr Ser Thr Thr Ile Arg Tyr Gln Ala Thr Gly
210                 215                 220

Phe Gly Thr Asn Glu Thr Glu Tyr Leu Phe Glu Val Asp Asn Leu Thr
225                 230                 235                 240

Tyr Val Gln Leu Glu Ser Arg Phe Thr Pro Gln Phe Leu Leu Gln Leu
                245                 250                 255

Asn Glu Thr Ile Tyr Thr Ser Gly Lys Arg Ser Asn Thr Thr Gly Lys
            260                 265                 270

Leu Ile Trp Lys Val Asn Pro Glu Ile Asp Thr Thr Ile Gly Glu Trp
        275                 280                 285

Ala Phe Trp Glu Thr Lys Lys Thr Ser Leu Glu Lys Phe Ala Val Lys
290                 295                 300

Ser Cys Leu Ser Gln Leu Tyr Gln Thr Glu Pro Lys Thr Ser Val Val
305                 310                 315                 320
```

```
Arg Val Arg Arg Glu Leu Leu Pro Thr Gln Gly Pro Thr Gln Gln Leu
            325                 330                 335

Lys Thr Thr Lys Ser Trp Leu Gln Lys Ile Pro Leu Gln Trp Phe Lys
            340                 345                 350

Cys Thr Val Lys Glu Gly Lys Leu Gln Cys Arg Ile
            355                 360

<210> SEQ ID NO 31
<211> LENGTH: 19
<212> TYPE: PRT
<213> ORGANISM: Artificial Sequence
<220> FEATURE:
<223> OTHER INFORMATION: Synthetic peptide

<400> SEQUENCE: 31

Ile Tyr Tyr Ser Gly Ser Thr Asn Tyr Asn Pro Ser Leu Lys Ser Arg
1               5                   10                  15

Val Thr Ile
```